United States Patent
Han et al.

(10) Patent No.: US 12,385,163 B2
(45) Date of Patent: Aug. 12, 2025

(54) ROTARY FIBROUS MATERIAL APPLICATION TO MEDICAL DEVICES

(71) Applicant: Edwards Lifesciences Corporation, Irvine, CA (US)

(72) Inventors: Jingjia Han, Irvine, CA (US); Hao Shang, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 691 days.

(21) Appl. No.: 17/649,304

(22) Filed: Jan. 28, 2022

(65) Prior Publication Data

US 2022/0154370 A1  May 19, 2022

Related U.S. Application Data

(63) Continuation of application No. PCT/US2020/044412, filed on Jul. 31, 2020.
(Continued)

(51) Int. Cl.
*D01D 5/18* (2006.01)
*A61F 2/24* (2006.01)
(Continued)

(52) U.S. Cl.
CPC ............. *D01D 5/18* (2013.01); *A61F 2/2415* (2013.01); *A61F 2/2418* (2013.01);
(Continued)

(58) Field of Classification Search
None
See application file for complete search history.

(56) References Cited

U.S. PATENT DOCUMENTS 3,143,742 A   8/1964 Cromie
3,320,972 A   5/1967 High et al.
(Continued)

FOREIGN PATENT DOCUMENTS

EP   0125393 A1   11/1984
EP   0143246 A2   6/1985
(Continued)

OTHER PUBLICATIONS

Van Lieshout, M. I., et al. "Electrospinning versus knitting: two scaffolds for tissue engineering of the aortic valve." Journal of Biomaterials Science, Polymer Edition 17.1-2 (2006): 77-89. (Year: 2006).*

(Continued)

*Primary Examiner* — Benjamin A Schiffman
(74) *Attorney, Agent, or Firm* — Chang & Hale LLP

(57) ABSTRACT

A method of applying fibrous material to a medical device component involves coupling a medical device component a holder device, rotating a reservoir device containing a liquid polymeric solution to expel at least a portion of the liquid polymeric solution from an orifice of the reservoir device, the expelled at least a portion of the liquid polymeric solution forming one or more strands of fibrous material in a deposition plane, and rotating the holder device at least partially within the deposition plane to apply at least a first portion of the one or more strands of fibrous material to one or more surfaces of the medical device component, thereby forming a fibrous covering on the one or more surfaces of the medical device component.

20 Claims, 25 Drawing Sheets

Related U.S. Application Data

(60) Provisional application No. 62/882,352, filed on Aug. 2, 2019.

(51) Int. Cl.
  *D01D 5/00* (2006.01)
  *D01D 7/00* (2006.01)

(52) U.S. Cl.
  CPC ......... *A61F 2/2463* (2013.01); *D01D 5/0084* (2013.01); *D01D 7/00* (2013.01); *A61F 2210/0076* (2013.01); *A61F 2230/0054* (2013.01); *A61F 2250/0039* (2013.01); *D10B 2509/06* (2013.01)

(56) References Cited

U.S. PATENT DOCUMENTS

| | | |
|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,323,525 A * | 4/1982 | Bornat ..................... A61F 2/06 264/441 |
| 4,340,091 A * | 7/1982 | Skelton .................... A61F 2/06 87/8 |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,475,972 A * | 10/1984 | Wong .................... B29C 53/587 156/175 |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A * | 3/1988 | Rousseau ............... A61F 2/2412 623/2.19 |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |

(56) References Cited

U.S. PATENT DOCUMENTS

| | | |
|---|---|---|
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,309,413 B1 * | 10/2001 | Dereume .................. A61F 2/91 623/1.13 |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,409,674 B1 | 6/2002 | Brockway et al. |
| 6,425,916 B1 | 7/2002 | Garrison et al. |
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 * | 7/2006 | Majercak .................. A61F 2/2418 623/1.3 |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,351,256 B2 * | 4/2008 | Hojeibane ............... A61F 2/2475 623/1.24 |
| RE40,377 E | 6/2008 | Williamson, IV et al. |
| 7,416,530 B2 | 8/2008 | Turner et al. |
| 7,422,603 B2 | 9/2008 | Lane |
| 7,485,141 B2 * | 2/2009 | Majercak .................. A61F 2/2412 623/1.44 |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,758,632 B2 * | 7/2010 | Hojeibane .............. A61F 2/2412 623/1.13 |
| 7,916,013 B2 | 3/2011 | Stevenson |
| 7,998,151 B2 | 8/2011 | St. Goar et al. |
| 8,066,650 B2 | 11/2011 | Lee et al. |
| 8,192,981 B2 * | 6/2012 | Hoerstrup .............. C12M 21/08 435/395 |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,399,243 B2 * | 3/2013 | Bouten .................. C12N 5/069 435/284.1 |
| 8,401,659 B2 | 3/2013 | Von Arx et al. |
| 8,529,474 B2 | 9/2013 | Gupta et al. |
| 8,617,237 B2 * | 12/2013 | Hoerstrup .............. A61F 2/2418 623/2.14 |
| 8,622,936 B2 | 1/2014 | Schenberger et al. |
| 8,636,793 B2 * | 1/2014 | Hoerstrup .............. A61L 31/148 623/2.14 |
| 9,056,006 B2 * | 6/2015 | Edelman ................ A61F 2/2415 |
| 9,101,264 B2 | 8/2015 | Acquista |
| 9,101,281 B2 | 8/2015 | Reinert et al. |
| 9,410,267 B2 * | 8/2016 | Parker .................... D04H 3/016 |
| 9,669,141 B2 * | 6/2017 | Parker .................. A61M 60/896 |
| 9,693,862 B2 | 7/2017 | Campbell et al. |
| 9,738,046 B2 * | 8/2017 | Parker ................ B29D 99/0078 |
| 10,213,297 B2 * | 2/2019 | Sanders ................. C12M 29/04 |
| 10,232,564 B2 * | 3/2019 | Pelled .............. B29C 66/53245 |
| 10,265,059 B2 * | 4/2019 | Rowe .................... A61F 2/2427 |
| 10,292,814 B2 * | 5/2019 | Weber .................... A61F 2/2412 |
| 10,456,245 B2 * | 10/2019 | Nguyen .................. A61L 31/10 |
| 10,519,569 B2 * | 12/2019 | Parker ........................ D01F 9/00 |
| 10,932,903 B2 * | 3/2021 | Levi ...................... A61F 2/2418 |
| 11,517,428 B2 * | 12/2022 | Shang .................... A61F 2/2418 |
| 12,064,341 B2 * | 8/2024 | Hoang .................. A61F 2/2418 |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0093080 A1 * | 5/2004 | Helmus .................. A61L 27/54 623/2.41 |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |

(56) References Cited

U.S. PATENT DOCUMENTS

| | | |
|---|---|---|
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0246584 A1* | 11/2006 | Covelli ............... A61L 27/3604 623/2.13 |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0038352 A1* | 2/2008 | Simpson ............... A61L 27/34 424/93.1 |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0281434 A1* | 11/2008 | Schmidt ............... C12N 5/0697 623/23.72 |
| 2008/0319543 A1 | 12/2008 | Lane |
| 2009/0036903 A1 | 2/2009 | Ino et al. |
| 2009/0192591 A1 | 7/2009 | Ryan et al. |
| 2009/0192599 A1 | 7/2009 | Lane et al. |
| 2009/0209982 A1* | 8/2009 | Hoerstrup ............... A61L 27/18 606/151 |
| 2010/0049313 A1 | 2/2010 | Alon et al. |
| 2010/0145438 A1 | 6/2010 | Barone |
| 2010/0256723 A1 | 10/2010 | Murray |
| 2012/0123284 A1 | 5/2012 | Kheradvar |
| 2012/0296382 A1 | 11/2012 | Shuros et al. |
| 2013/0144379 A1 | 6/2013 | Najafi et al. |
| 2013/0312638 A1* | 11/2013 | Parker ............... A61B 17/00234 264/211.1 |
| 2014/0128964 A1 | 5/2014 | Delaloye |
| 2014/0188221 A1 | 7/2014 | Chung et al. |
| 2014/0260097 A1* | 9/2014 | Avery ............... A61F 2/9524 72/367.1 |
| 2014/0364707 A1 | 12/2014 | Kintz et al. |
| 2015/0045635 A1 | 2/2015 | Tankiewicz et al. |
| 2016/0045316 A1 | 2/2016 | Braido et al. |
| 2016/0317305 A1* | 11/2016 | Pelled ............... A61F 2/2412 |
| 2016/0331528 A1* | 11/2016 | Parker ............... A61F 2/2412 |
| 2017/0325976 A1* | 11/2017 | Nguyen ............... A61L 31/10 |
| 2019/0321170 A1 | 10/2019 | Green et al. |
| 2022/0233310 A1* | 7/2022 | Neumann ......... A61M 25/0045 |
| 2023/0158204 A1* | 5/2023 | Tkatchouk ........... C09D 5/1637 424/423 |
| 2023/0248512 A1* | 8/2023 | Tod ............... A61F 2/2415 623/2.15 |
| 2024/0081988 A1* | 3/2024 | Desai ............... D01F 6/92 |
| 2024/0138975 A1* | 5/2024 | Nawalakhe ............ A61F 2/2418 |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |

OTHER PUBLICATIONS

Capulli, Andrew K., et al. "JetValve: Rapid manufacturing of biohybrid scaffolds for biomimetic heart valve replacement." Biomaterials 133 (Apr. 18, 2017): 229-241. (Year: 2017).*

(56) References Cited

OTHER PUBLICATIONS

Motta, Sarah E., et al. "On-demand heart valve manufacturing using focused rotary jet spinning." Matter 6.6 (Jun. 7, 2023): 1860-1879. (Year: 2023).*

* cited by examiner

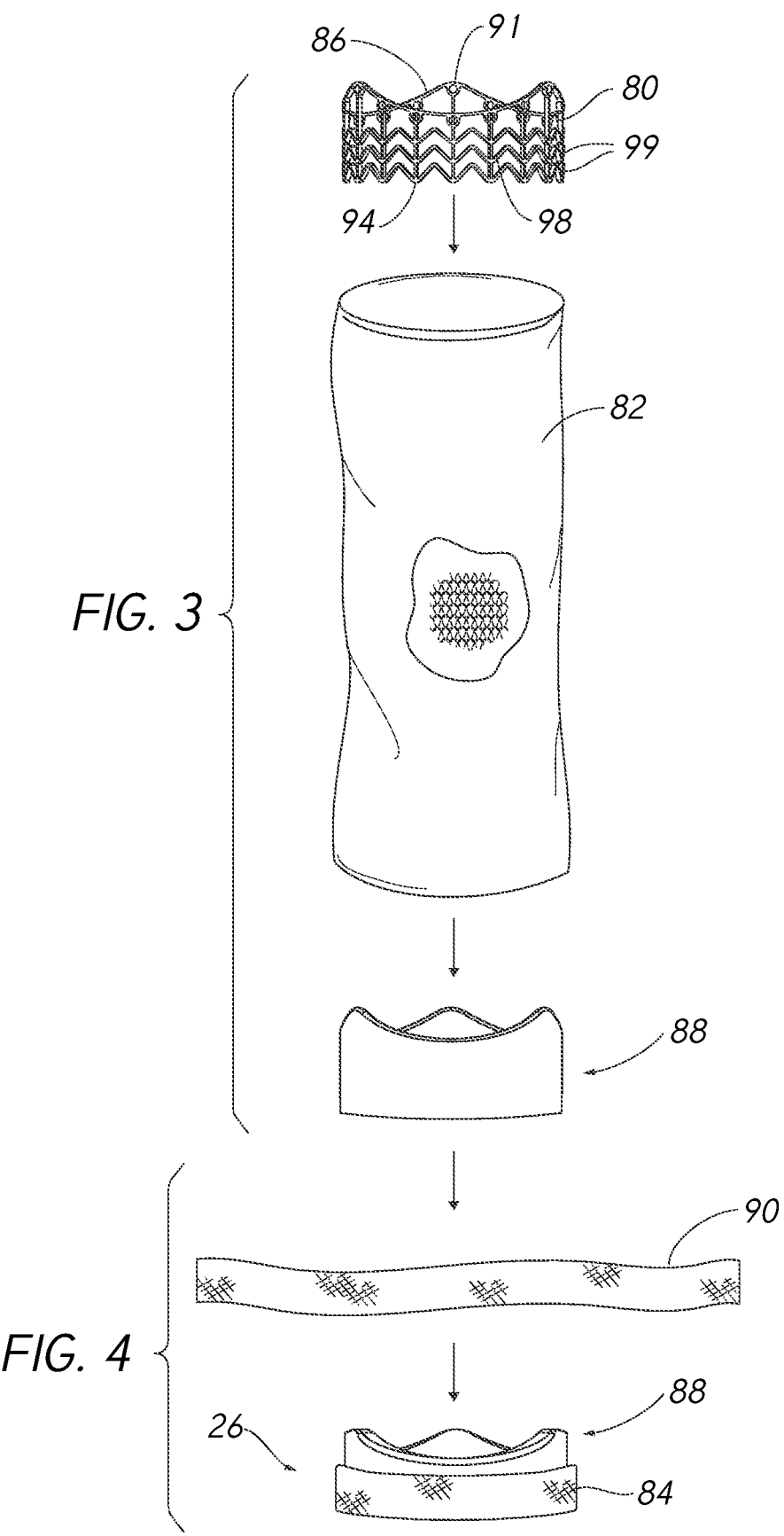

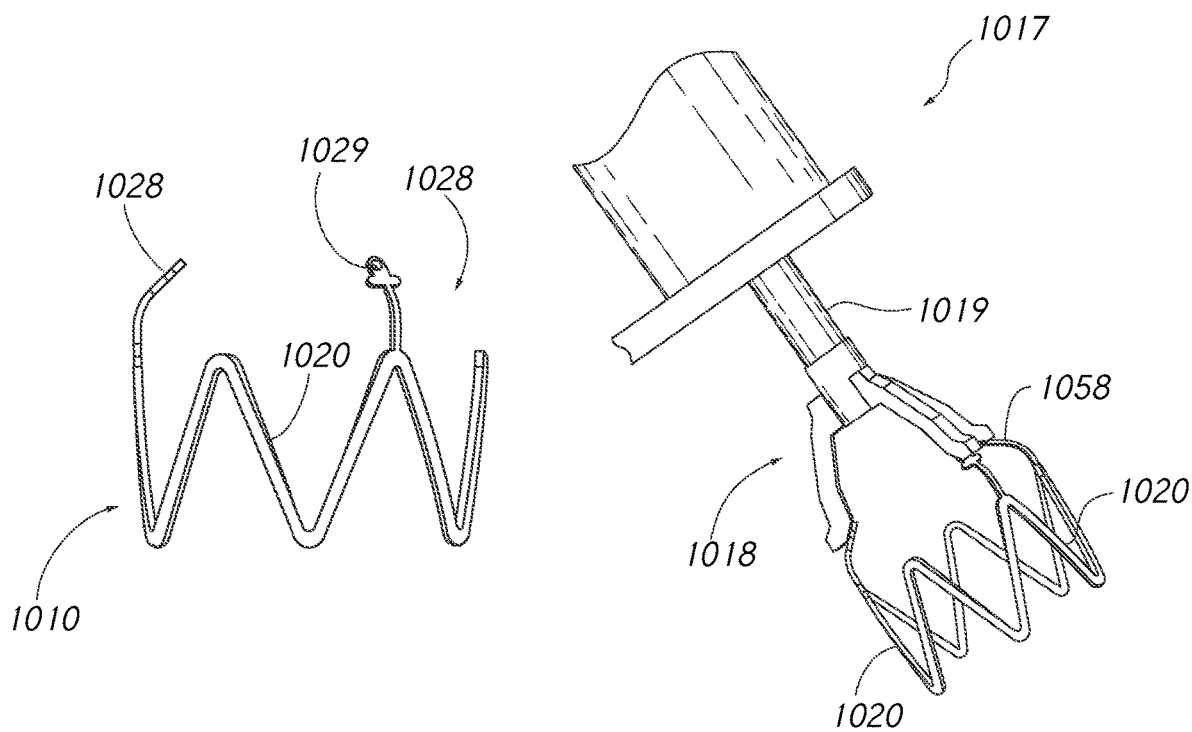
FIG. 32
FIG. 33
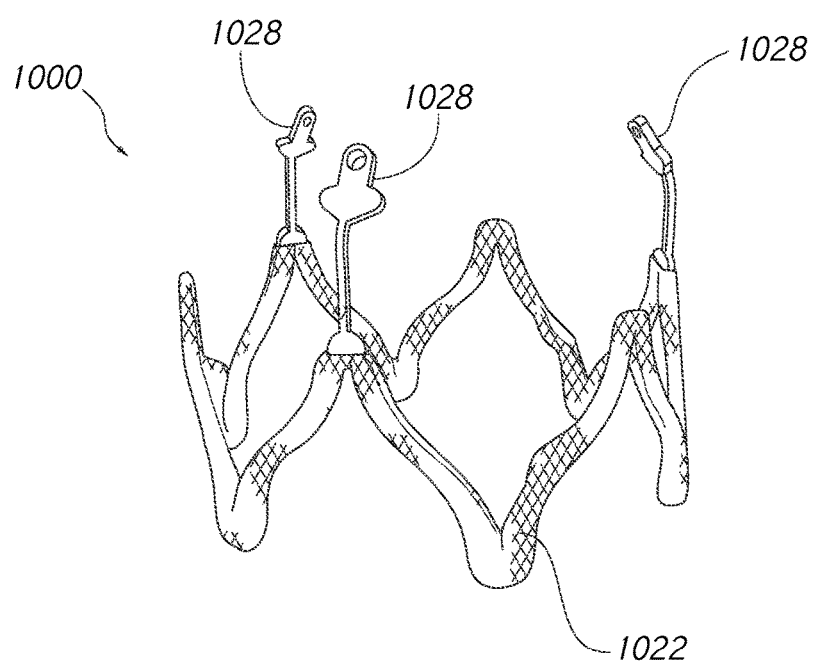
FIG. 34

ROTARY FIBROUS MATERIAL APPLICATION TO MEDICAL DEVICES

RELATED APPLICATION

This application is a continuation of International Patent Application No. PCT/US2020/044412, filed on Jul. 31, 2020, which claims the benefit of U.S. Patent Application No. 62/882,352, filed on Aug. 2, 2019, the entire disclosures all of which are incorporated by reference for all purposes.

BACKGROUND

Field

The present disclosure generally relates to the field of medical implant devices.

Description of Related Art

Various medical devices include component(s) having cloth or other fibrous features. Manufacturing of such devices according to various application processes can be cumbersome. Furthermore, material characteristics of such cloths/fibrous features can affect the efficacy of associated medical devices.

SUMMARY

Described herein are methods and devices that facilitate application of fibrous material and/or features to medical devices. In some implementations, the present disclosure relates to a method of applying fibrous material to a medical device component. The method comprises coupling a medical device component a holder device, rotating a reservoir device containing a liquid polymeric solution to expel at least a portion of the liquid polymeric solution from an orifice of the reservoir device, the expelled at least a portion of the liquid polymeric solution forming one or more strands of fibrous material in a deposition plane, and rotating the holder device at least partially within the deposition plane to apply at least a first portion of the one or more strands of fibrous material to one or more surfaces of the medical device component, thereby forming a fibrous covering on the one or more surfaces of the medical device component.

In some embodiments, the holder device is a component of a collection assembly further comprising a rotary motor and a mandrel that is mechanically coupled to the holder device and the rotary motor. For example, the method may further comprise translating the collection assembly along a vertical axis while expelling the at least a portion of the liquid polymeric solution.

The holder device can advantageously have an at least partially cylindrical spacer form. For example, the method may further comprise applying at least a second portion of the one or more strands of fibrous material to a surface of the holder device, thereby forming a surplus fibrous covering portion on the surface of the holder device. The method may further comprise decoupling the medical device component from the holder device and folding the surplus fibrous covering portion over at least one edge of the medical device component to cover at least a portion of an inside surface of the medical device component. As an alternative to folding the surplus material, the mandrel can be coated first, with the stent subsequently mounted, after which the outer skirt can be coated. Once complete, the sandwiched stent and fibrous material can be withdrawn from the holder. In some implementations, a laser (e.g., $CO_2$ laser) can be used to cut out/off any excess fibrous material.

In some implementations, wherein the holder device comprises a plurality of arms configured to be coupled to the medical device component. For example, coupling the medical device component to the holder device can comprise suturing the medical device component to the plurality of arms of the holder device. In some implementations, rotating the reservoir device and the holder device is performed at least in part using control circuitry communicatively coupled to a collection assembly associated with the holder device and a deposition assembly associated with the reservoir device.

In some implementations, the medical device component comprises a stent of a transcatheter prosthetic heart valve implant device, the holder device comprises an at least partially cylindrical spacer form, and coupling the medical device component to the holder involves disposing the stent about the spacer form. For example, the stent can have a non-uniform longitudinal diameter. In some implementations, the medical device component comprises a frame of a surgical prosthetic heart valve implant device, the holder device comprises a plurality of arms, and coupling the medical device component to the holder involves coupling the frame to the plurality of arms. For example, the frame can comprise a wireform defining a plurality of commissure posts and an anchoring skirt coupled to a sealing ring portion of the surgical prosthetic heart valve implant device.

The method can further comprise applying at least a second portion of the one or more strands of fibrous material to the anchoring skirt to form a skirt covering, wherein the skirt covering is coarser than the fibrous covering. For example, in some embodiments, the frame comprises a body portion and an anchor feature portion and applying the at least a first portion of the one or more strands of fibrous material to the one or more surfaces of the medical device component involves covering at least a portion of the anchor feature portion of the frame with fibrous material. Covering the at least a portion of the anchor feature portion may be performed when the anchor feature portion is in a straightened-out configuration.

In some embodiments, the medical device component comprises a valve leaflet spacer device. For example, rotating the holder device may be performed with the valve leaflet spacer device configured in an at least partially straightened-out configuration, wherein the method further comprises transitioning the valve leaflet spacer device from the at least partially straightened-out configuration to a folded configuration after said forming the fibrous covering on the one or more surfaces of the medical device component.

In some implementations, the present disclosure relates to a method of applying fibrous material to a medical device component. The method comprises coupling a holder device to a rotatable mandrel, the holder device comprising a spacer form, rotating a reservoir device containing a liquid polymeric solution to expel at least a portion of the liquid polymeric solution from an orifice of the reservoir device, the expelled at least a portion of the liquid polymeric solution forming one or more strands of fibrous material in a deposition plane, rotating the holder device at least partially within the deposition plane to apply at least a first portion of the one or more strands of fibrous material to a surface of the holder device, thereby forming a fibrous covering on the surface of the holder device, and disposing a medical device component on the holder device over the fibrous covering.

The method may further comprise applying a layer of fibrous material from the reservoir over at least a portion of an outer surface of the medical device component and withdrawing the medical device component together with the fibrous covering and the layer of fibrous material from the holder device. As an alternative to folding the surplus material, the mandrel can be coated first, with the stent subsequently mounted, after which the outer skirt can be coated. Once complete, the sandwiched stent and fibrous material can be withdrawn from the holder. In some implementations, a laser (e.g., $CO_2$ laser) can be used to cut out/off any excess fibrous material. The method may further comprise folding a portion of the fibrous covering over an outer surface of the medical device component. In some embodiments, the spacer form is cylindrical.

For purposes of summarizing the disclosure, certain aspects, advantages and novel features are described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIGS. 3 and 4 shown another example assembly of an at least partially cloth-covered prosthetic heart valve implant device in accordance with one or more embodiments.

FIG. 32 shows an example type of docking device that can be covered at least in part by fibrous material using rotary jet spinning solutions in accordance with one or more embodiments.

FIG. 33 shows a docking device frame disposed on a holder in accordance with one or more embodiments.

FIG. 34 shows a docking device having fibrous material applied to portions thereof using rotary jet spinning in accordance with one or more embodiments.

Figure 1:
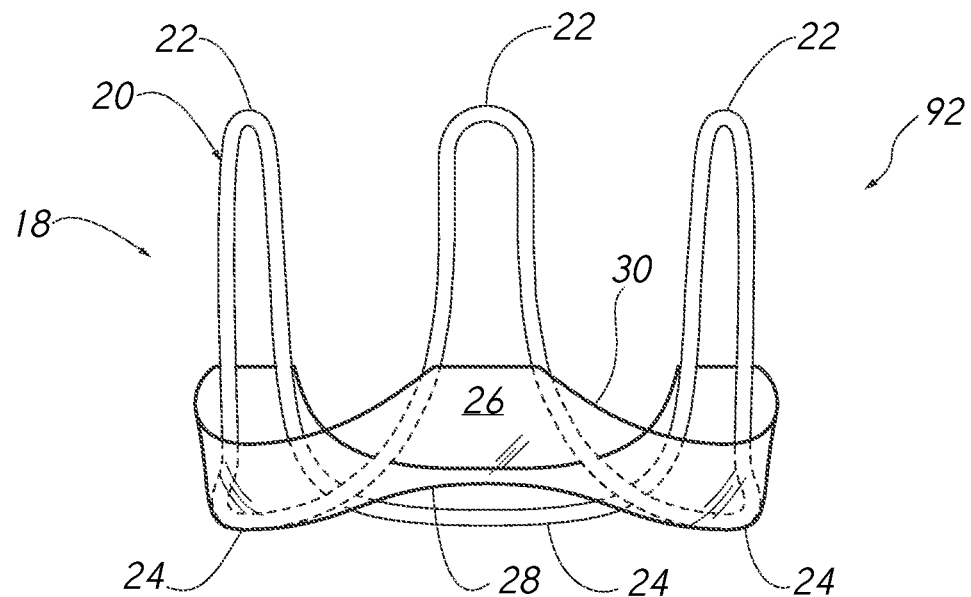
FIG. 1 shows a frame for a support stent for a surgical heart valve in accordance with one or more embodiments.

To further clarify various aspects of embodiments of the present disclosure, a more particular description of certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments of the present disclosure will be described and explained with additional specificity and detail through the use of the accompanying drawings.

DETAILED DESCRIPTION

Embodiments of the technology disclosed herein are directed toward methods for methods and devices that facilitate application of fibrous material/features to medical devices. More particularly, various embodiments of the technology disclosed herein relate to methods for applying rotary-jet-spun fibrous material to one or more surfaces of a medical device, such as a wireform frame or stent.

Various medical devices include components that are advantageously covered at least in part by cloth or other fibrous material. The terms "fiber" and "fibrous material" are used herein according to their broad and ordinary meanings and may refer to any type of natural or synthetic substance or material that is significantly longer than it is wide, including any elongate or relatively fine, slender, and/or threadlike piece, filament, cord, yarn, plie, strand, line, string, or portion thereof. Furthermore, "fiber" or "fibrous material" may refer to a single filament or collectively to a plurality of filaments. Examples of fibrous material in accordance with embodiments of the present disclosure include any type of cloth, fabric, or textile. While certain description below refers to "cloth" and/or "cloth-covered" features, it should be understood that such description is applicable to any type of fibrous material, including any type of cloth, fabric, textile, or interlocking-fiber material or form.

Examples of medical device components that may be covered or otherwise associated with cloth or other fibrous material include certain stents, which may generally comprise a conduit form configured to be placed in a body to create or maintain a passageway within the body, or to provide a relatively stable anchoring structure for supporting one or more other devices or anatomy. At least partially cloth-covered stents can be used for a variety of purposes, such as for expansion of certain vessels, including blood vessels, ducts, or other conduits, whether vascular, coronary, biliary, or other type. In the context of a prosthetic heart valve devices, a stent can serve as a structural component for anchoring the prosthetic heart valve to the tissue of a heart valve annulus. Such a stent can have varying shapes and/or diameters.

It should be understood that prosthetic heart valve implants, as well as many other types of prosthetic implant devices and other types of devices, can include various cloth-covered components and/or portions. For example, a sealing portion of a medical implant device, such as a prosthetic heart valve skirt component/portion, can be sutured to a frame thereof to help prevent blood from leaking around the outer edges or circumference of the device.

In some implementations, cloth coverings for medical device components can be secured using sutures. For example, in some implementations, a human operator may handle, and execute sutures on, implant device components to secure a cloth thereto. However, execution of sutures by a human operator may be relatively difficult and/or cumbersome in certain situations. For example, where small stitches are to be made with relatively high precision, the complexity and/or associated operator burden may result in injury/strain and/or undesirably-low product quality. Furthermore, medical implant devices, such as certain heart valve implant devices, may require upward of a thousand sutures, or more, which can involve substantially labor-intensive and error-susceptible suturing procedures. Therefore, reducing the collaborative human involvement in application of fibrous material to medical device components can be desirable to improve quality and efficiency, and/or to reduce operator strain.

Certain embodiments disclosed herein provide for application of fibrous material to medical implant device component(s) using rotary jet spinning devices, systems, processes, and mechanisms. The various embodiments relating to rotary jet fabric application are applicable to medical implant devices and heart valves having any type of structural configuration or pattern. Examples of medical implant devices and heart valve structures that may be applicable to certain embodiments presented herein are disclosed in International Patent Publication No. WO 2015/070249, the entire contents of which is hereby expressly incorporated by reference for all purposes.

Some example medical implant devices incorporating cloth coverings comprise prosthetic heart valve implants incorporating cloth-covered bands and/or wireframes, which may provide sealing, structural support, and/or anchoring functionality. FIG. 1 shows a frame 92 for a support stent for a surgical heart valve according to some embodiments. The frame 92 can include multiple cusps curved toward an axial inflow end alternating with multiple commissures 22 projecting toward an axial outflow end, the support stent 92 defining an undulating outflow edge. The support stent 92 can comprise a wireform 20 having three upstanding commissures 22 alternating with three cusps 24 which generally circumscribe a circumference. A stiffening band 26 may be disposed within or without the wireform 20. The inflow edge of the band 26 can at least partially conform to the cusps 24 of the wireform 20 and may be curved in the outflow direction in between in the region of the wireform commissures 22. In certain embodiments, the support stent 92 provides the supporting structure of a one-way surgical prosthetic heart valve, as disclosed in greater detail in connection with some embodiments described below.

Figure 2:
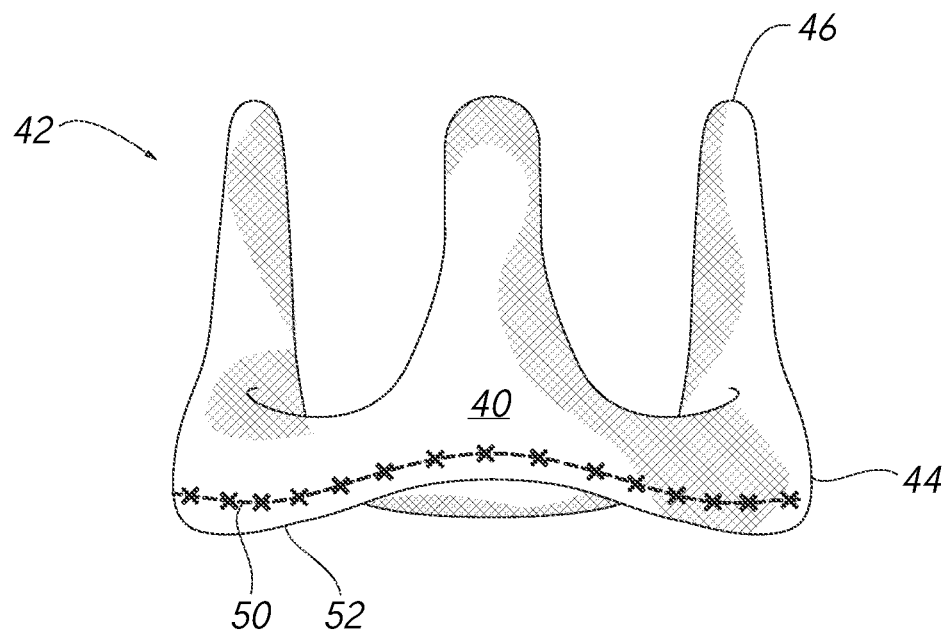
FIG. 2 illustrates the frame of FIG. 1 covered at least partially with fabric in accordance with one or more embodiments.

FIG. 2 illustrates the frame 92 of FIG. 1 covered with fabric 40, wherein the fabric 40 may be sutured in one or more portions to secure the fabric 40 as a covering for the frame 92. The fabric-covered support stent 42 may be generally tubular and may include multiple cusps 44 curved toward the axial inflow end alternating with multiple commissures 46 projecting toward the axial outflow end. The support stent 42 may comprise an undulating outflow edge about which the fabric 40 is secured or held. In certain embodiments, a seam 50 may be sutured adjacent the inflow edge 52 that secures the fabric 40 about the support stent. The seam 50 is shown slightly axially above the inflow edge 52 for clarity, although it may be located directly at the inflow edge or even inside the support stent. In one embodiment, one or more seams may be located in other positions on the fabric. The support stent 42 and/or one or more other components of the associated implant device can also have leaflets and/or other materials sutured thereto, as described in detail below.

FIGS. 3 and 4 show an exploded view of another example assembly of an at least partially cloth-covered prosthetic heart valve implant device, which is presented to provide additional context relating to incorporation of cloth/fabric coverings in medical implant devices. In particular, the example of FIGS. 3 and 4 may generally relate to a valve implant device having an associated fabric-covered anchoring skirt 26. For example, a self-expanding stent or balloon-expanding stent may be used as part of a prosthetic heart valve having a single-stage implantation in which a surgeon secures a hybrid heart valve having an anchoring skirt and valve member to a heart valve annulus as one unit or piece. Some related solutions especially for aortic valve replacement are provided in U.S. Pat. No. 8,641,757, the disclosure of which is incorporated herein by reference in its entirety for all purposes. In some implementations, an implantation process associated with the assembly of FIGS. 3 and 4 may require as few as three sutures, unlike more time-consuming processes requiring placement of a dozen or more sutures and tying knots for each of a plurality of components/portions of the assembly.

The valve implant assembly of FIGS. 3 and 4 may incorporate a valve frame, which may be similar in one or more respects to the frame shown in FIGS. 1 and 2 and described above. The anchoring skirt 26 may include an inner plastically-expandable stent covered with a fabric, for example, a polymeric fabric. The anchoring skirt 26 may comprise an inner stent frame 80, a fabric covering 82, and a band-like lower sealing flange 84. The inner stent frame 80 may comprise a tubular plastically-expandable member having an undulating or scalloped upper end 86 that matches the contours of an inflow portion of the heart valve.

In some implementations, the fabric 82 may be sewn to the stent frame 80. For example, the tubular section of fabric 82 may be drawn taut around the stent frame 80, inside and/or outside, and sewn thereto to form an intermediate, cloth-covered frame 88. After surrounding the stent frame 80 with the fabric 82, a series of longitudinal sutures can be implemented to secure the two components together. Furthermore, a series of stitches may be implemented along the undulating upper end 86 of the stent frame 80 to complete the fabric enclosure.

Generally, the cloth/fabric 82 attached to the stent 80 can serve to reduce friction between the stent and the relevant body orifice, to secure the prosthetic heart valve in the orifice location, to fill gaps through which fluid could pass through, and/or to provide a location for tissue in-growth. Applying and sewing the cloth 82, however, can be a relatively time-consuming and laborious process.

In addition to the cloth/fabric components illustrated in FIGS. 1-4, medical device implant devices can include various other cloth-covered and/or sutured components and/or portions. Application of fibrous material to medical device component(s) by a human operator can be relatively difficult and/or cumbersome in certain implementations. For example, where small stitches are to be made with relatively high precision, the complexity and/or associated operator burden may result in injury and/or undesirably low quality of products. Furthermore, certain heart valve implant devices may require upward of a thousand sutures, which can involve substantially labor-intensive and error-susceptible suturing procedures. Therefore, simplification of the application of cloth/fabric to medical device implants can potentially improve quality and/or reduce operator involvement, such as requiring less handling to position and/or hold cloth/fabric portions in place for suturing.

Figure 5:
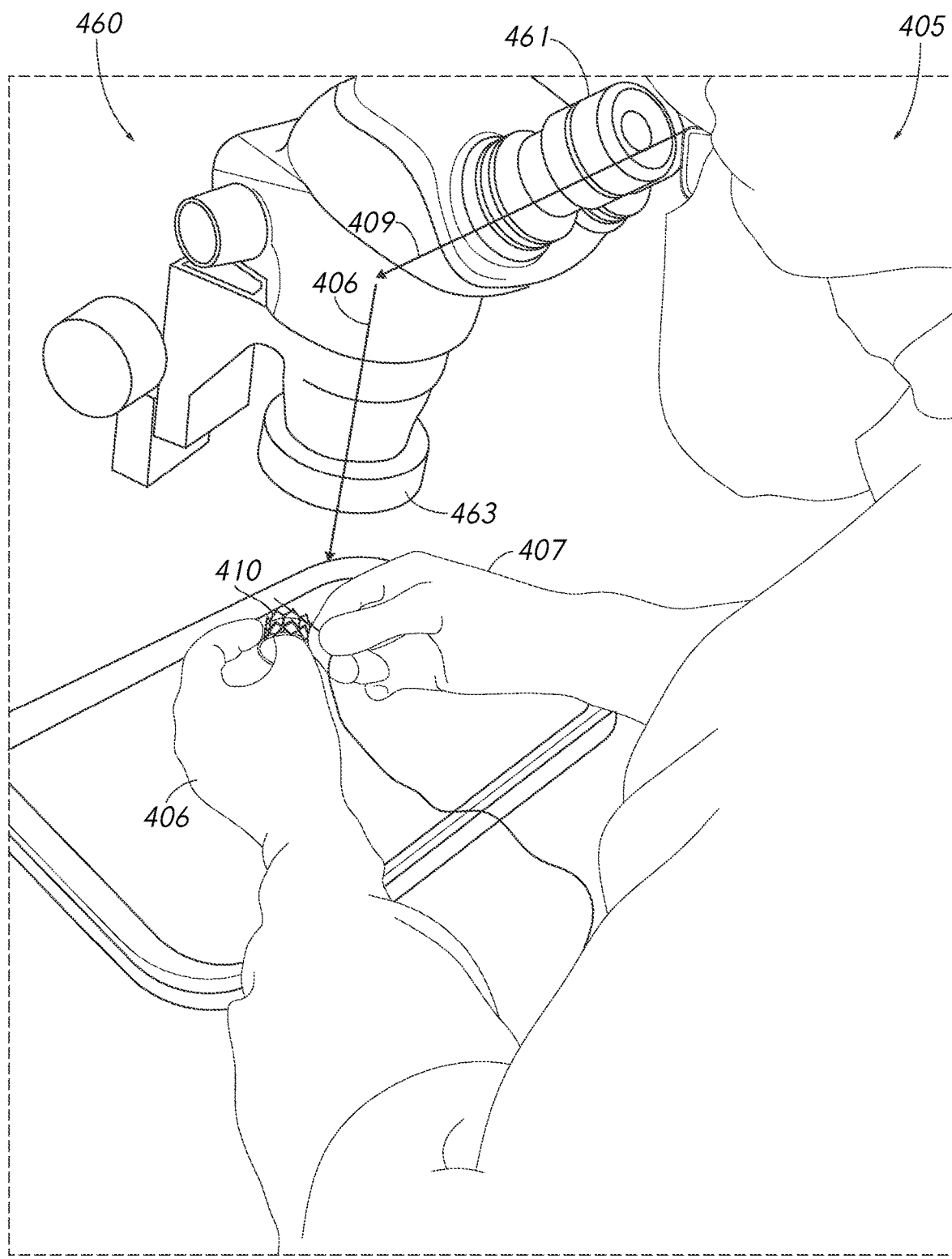
FIG. 5 illustrates an operator performing operations on a prosthetic human implant device in accordance with one or more embodiments.

Generally, application of cloth to medical implant devices may be performed in various ways. For example, certain handheld processes for applying and suturing fibrous material to prosthetic human implant devices may be implemented in which an operator utilizes both hands for holding, securing, and/or suturing the cloth/fabric portions of the implant device. As an example, FIG. 5 illustrates an operator 405 performing operations on a prosthetic human implant device 410. In some implementations, an operator 405 may hold and/or suture an outer wireframe of a device 410 to an inner skirt or cloth, as described above. In the example of FIG. 5, the implant device 410 may be a transcatheter heart valve device or other implant device.

As illustrated in the diagram of FIG. 5, in some processes, an operator 405 may need to utilize both of his or her hands for attaching fibrous material/cloth to a medical implant device. For example, a first hand 406 may be used to hold and/or secure the cloth/fabric to the implant device 410 in the desired position, whereas a second hand 407 may be used to manually operate a suturing needle or the like. Furthermore, for the operator 405 to effectively execute the relevant fabric-application operations, it may be necessary or desirable for the view of the implant device 410 to be magnified or otherwise enhanced in some manner. For example, as shown, the operator 405 may further utilize a magnification system 460, such as a microscope, which may comprise an eyepiece component 461 as well as one or more lenses and/or refractive elements 463. In certain embodiments, the magnification system 460 may be designed such that the operator 405 may have a line of sight 409 at a first angle, wherein the magnification system 460 is configured to at least partially reflect light therein at a downward angle 408 to provide a depth of field at a targeted distance from the refractive elements 463. By holding the implant device 410, or target portion thereof, within the depth of field of the magnification system 460, the operator 405 may be able to observe an enhanced view of the implant device 410 or target portion thereof, which may be desirable or necessary to execute the precise fabric application and/or suturing operations.

Figure 6:
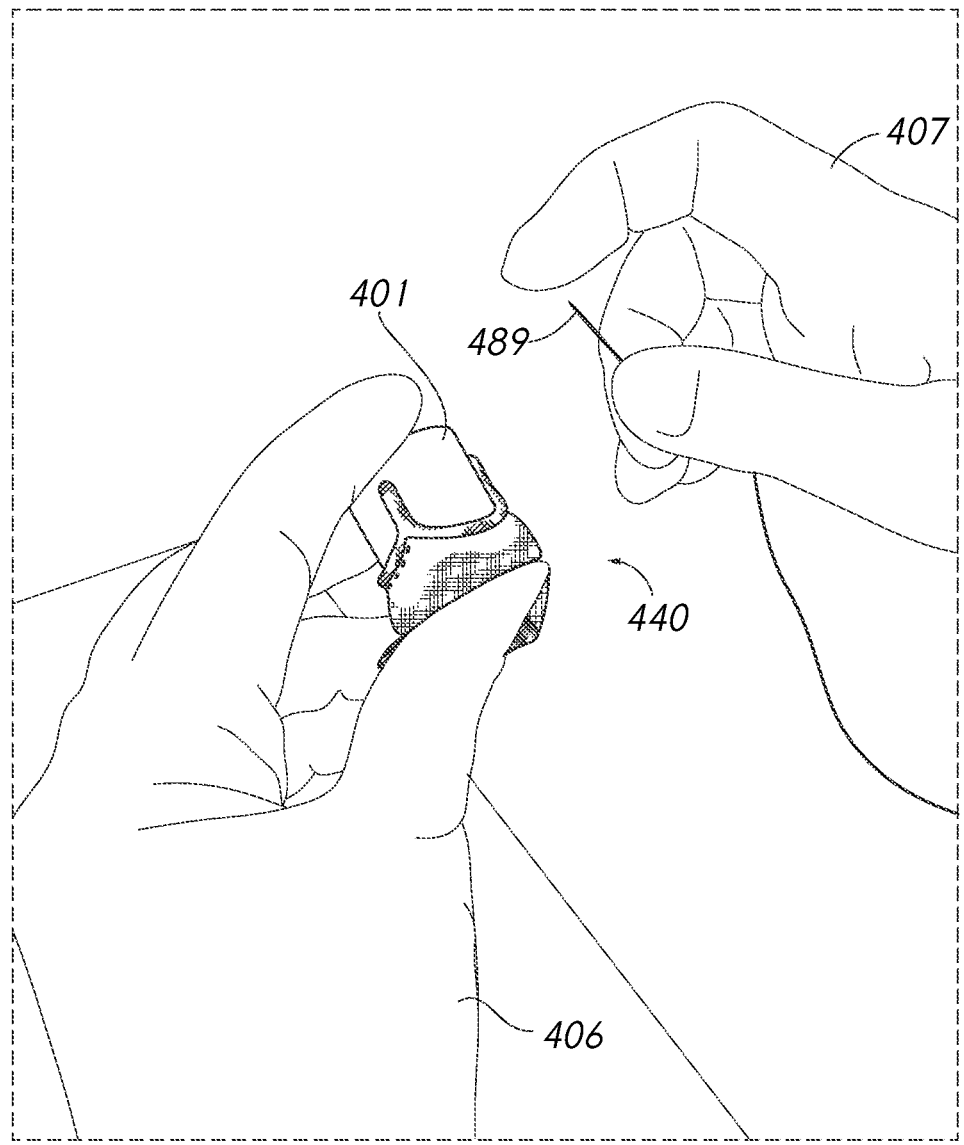
FIG. 6 illustrates a close-up view of a prosthetic implant device having a cloth/fabric component placed thereon and sutured using manual holding and suturing in accordance with one or more embodiments.

FIG. 6 illustrates a close-up view of a prosthetic implant device 440 having a cloth/fabric component placed thereon and sutured using manual holding and suturing, as described above. As shown, for handheld suturing solutions, a first hand 406 may be required to hold the cloth/fabric component in place on the implant device 440, while a second hand 507 may be required to manipulate the suturing needle 409, or the like. According to certain processes, the operator may be required to hold one or more hands in a substantially constant position over prolonged periods of time to maintain the cloth/fabric portion in the desired position while suturing is performed, which may require the operator to squeeze, push, pull, or otherwise exert manual force on one or more portions of the implant device 510, thereby causing strain on muscles, joints, or the like, of the operator's hands and/or other anatomy. The implant device 440 may be supported on a holder 401 in some implementations. In some implementations, handheld holders and tools may require operators to hold the holder or tool with one hand, thereby limiting the ability of the operator to use such holding hand to adjust the cloth/fabric component(s) for tensioning and/or realignment.

In some implementations, the present disclosure relates to systems, devices, and methods of applying fibrous material to surfaces of a medical implant device, such as a stent or the like, in a way that reduces labor time and production costs. Embodiments disclosed herein satisfy this need and other needs.

In some implementations, fibrous material may be applied to a medical implant device using an electrospinning process. For example, with respect to certain prosthetic heart valve implant devices, fibrous material may be applied to a metal stent structure, wherein the applied fibrous material may serve to reduce friction between the stent and certain anatomy (e.g., vessel/orifice) at the implantation site, to secure the implant device at the implantation site, to fill gaps through which fluid may pass, and/or to provide a surface for tissue in-growth.

Polymeric fibers, such as nanofibers, may have desirable utility for medical implant device coverings due to their high surface-to-mass ratio, high porosity, tissue in-growth properties, and because they can be easily wound into different shapes. Electrospinning represents one method for producing such nanofibers. Electrospinning processes generally employ high voltages to create an electric field between a droplet of polymer solution at the tip of a needle and a collector plate, as described in detail below. One electrode of the voltage source is placed into the solution and the other is connected to the collector. This creates an electrostatic force. As the voltage is increased, the electric field intensifies causing a force to build up on the pendant drop of polymer solution at the tip of the needle. This force acts in a direction opposing the surface tension of the drop. The increasing electrostatic force causes the drop to elongate forming a conical shape. When the electrostatic force overcomes the surface tension of the drop, a charged, continuous jet of solution is ejected from the cone. The jet of solution accelerates towards the collector, whipping and bending wildly. As the solution moves away from the needle and toward the collector, the jet rapidly thins and dries as the solvent evaporates. On the surface of the grounded collector, a nonwoven mat of randomly oriented solid nanofibers is deposited.

For certain cloth-application processes, as described in detail above, applying and suturing the cloth can be a time-consuming and laborious process. Electrospinning application of fibrous material represents one example of an alternative method of applying a fabric or fibrous material (e.g., polymeric fibrous material) to surfaces of a stent or other medical implant device component in a way that can reduce labor time and production costs. By way of illustration, electrospun polymeric material may be applied to a medical device implant (e.g., metal stent) while the implant and a supporting mandrel/holder are rotated by a rotary tool. Over time, the electrospinning process produces a layer of polymeric threads or fibers covering the outside of the target surface. Certain methods, devices, and systems relating to electrospinning concepts that may be applicable to embodiments of the present disclosure are disclosed in U.S. Publication No. 2017/0325976, the disclosure of which is hereby incorporated by reference in its entirety for all purposes.

Figure 7:
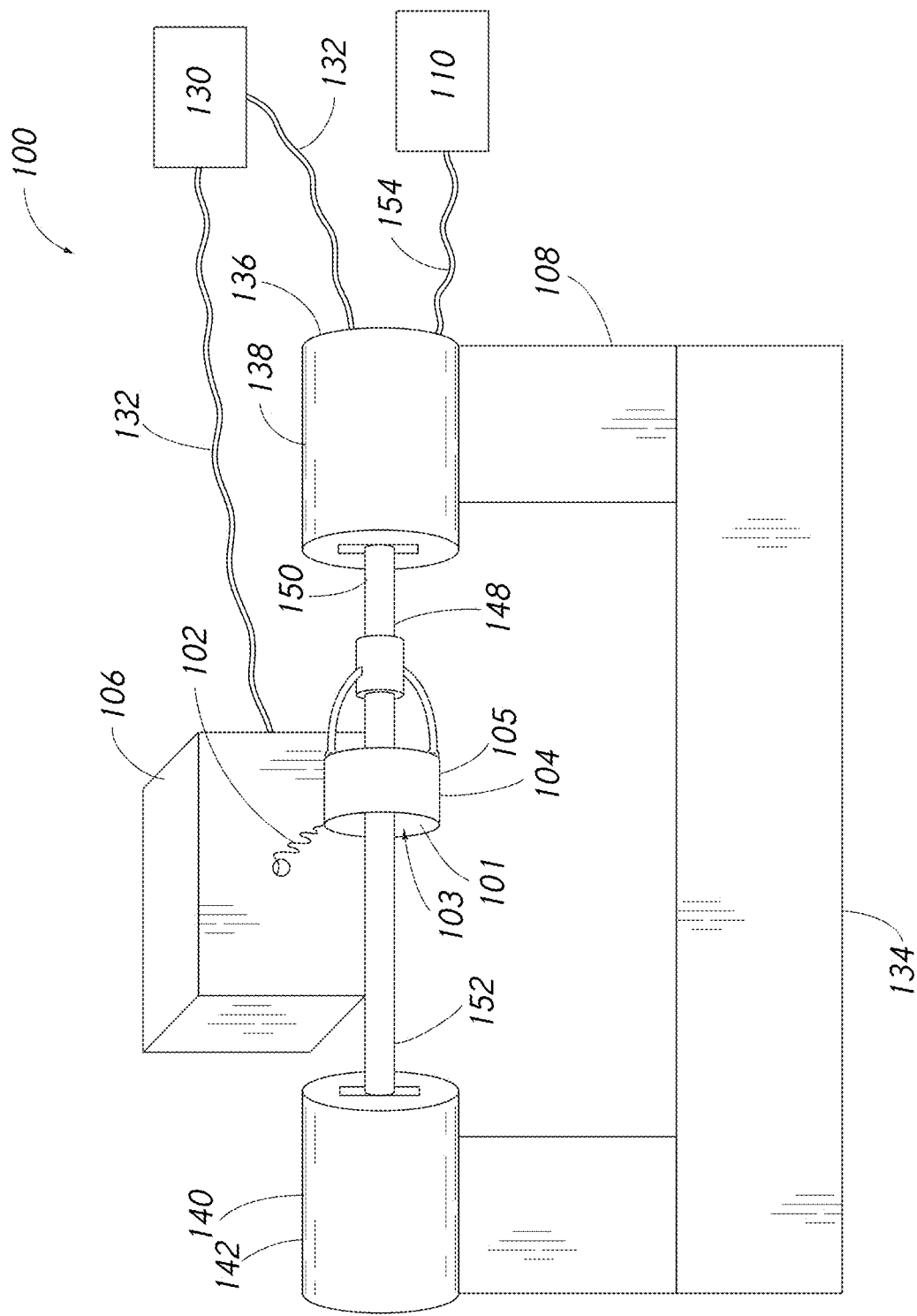
FIG. 7 shows an electrospinning system for applying fibrous material to a medical implant device component in accordance with one or more embodiments.

FIG. 7 shows a system 100 for applying an electrospinning material 102 to a stent or other medical implant device component 104. The system 100 comprises a source of electrospinning material 106, a collector 108, and a controller no. The source of electrospinning material is any suitable device, for example, a device comprising a spinneret electrically coupled to a voltage source. The source may comprise, for example, one or more syringe pumps, one or more syringes mounted on the syringe pump(s), and one or more syringe needles fluidly coupled to the syringe(s). In some embodiments, the spinneret-type syringe(s) are implemented. In some embodiments, a voltage source is electrically coupled to the syringe needle(s).

In some embodiments, the electrospinning material 102 is a solution of polyethylene terephthalate (PET). The PET solution may be created by mixing PET (e.g., at about 10% to 20% by weight) with a suitable solvent or mixture of solvents (e.g., hexafluoroisopropanol (HFIP) at about 80% to 90% by weight) and permitting the PET to dissolve fully. In a particular embedment, the PET solution is created by mixing PET at about 15% to 18% by weight with a solvent such as HFIP at about 82% to 85% by weight. Instead of or in addition to PET, another polymer may be used, either alone or in combination, such as a polymer selected from the group consisting of polytetrafluoroethylene (PTFE), polycaprolactone (PCL), polydioxanone (PDO), polyglycolic acid (PGA), and polyurethane (PU). Additionally, one or more drugs and/or biologically active ingredients may be added to the solution. Similarly, other solvents or mixtures thereof are used in other embodiments.

In some embodiments, the medical device implant 104 comprises a stent for use as part of a prosthetic heart valve, such as the Edwards Intuity® valve system disclosed in U.S. Pat. No. 8,641,757 to Pintor et al. or the Edwards SAPIEN® transcatheter heart valve. The stent 104 may be an expandable stainless-steel stent. The material, however, is not limited to stainless steel, and other materials such as cobalt-chrome alloys and nitinol may be used.

The syringe pump 106 serves as the source of the electrospinning material 102 to be applied to the stent 104. Some embodiments include a plurality of syringe pumps. In general, electrospinning uses an electrical charge to draw very fine (typically on the micro- or nanometer scale) fibers from a liquid, such as a polymer solution or a polymer melt. In some implementations, the polymer is discharged through a charged orifice toward a target, wherein the orifice and the target have opposing electrical charges. A voltage source is provided that creates a first charge at the charged orifice and an opposing charge at the target. The polymer is electrostatically charged by contact with the charged orifice. The electrostatically charged polymer is then collected at the target. Electrospinning PTFE is described in U.S. Patent Publication No. 2010/0193999, which is incorporated herein by reference for all purposes.

The syringe pump 106 may be used with a syringe, which may generally comprise a cylindrical body defining a reservoir into which an amount of the electrospinning material 102 is placed. After the reservoir is filled, the syringe may be placed on a syringe holder block of the syringe pump 106. Once the syringe pump 106 is fitted with a loaded syringe, the orifice of the syringe may be connected to a tube that that is coupled to a spinneret comprising a, e.g., stainless-steel needle. The electrospinning material 102 can be electrostatically drawn from the spinneret tip by applying a relatively high voltage or potential difference between the spinneret tip and the collector 108 using a high-voltage power supply 130 connected by wires 132 to the spinneret and the collector 108. In some embodiments, the high-voltage power supply 130 provides a direct-current (DC) power supply of about 5 kV to 50 kV.

In some implementations, fibrous material may be applied to a medical implant device using a rotary jet spinning process. For example, with respect to certain prosthetic heart valve implant devices, fibrous material may be applied to a metal stent structure, wherein the applied fibrous material may serve to reduce friction between the stent and certain anatomy (e.g., vessel/orifice) at the implantation site, to secure the implant device at the implantation site, to fill gaps through which fluid may pass, and/or to provide a surface for tissue in-growth. For certain cloth-application processes, as described in detail above, applying and suturing the cloth can be a time-consuming and laborious process. Rotary jet spinning application of fibrous material represents another example of a method of applying a fabric or fibrous material (e.g., polymeric fibrous material) to surfaces of a stent or other medical device implant component in a way that can reduce labor time and production costs. By way of illustration, rotary-jet-spun material may be applied to a medical device implant (e.g., metal stent) while the implant and a supporting holder are rotated by a rotary tool. Over time, the rotary jet spinning process can produce a layer of polymeric threads or fibers covering the outside of the target surface. Rotary jet spinning generally does not require use of any electric field, unlike electrospinning. Rotary jet spinning, as described in greater detail below, can involve conversion of a material (e.g., polymer) dissolved in a solvent into a continuous fibrous strand/fiber by centrifugal ejection of the material/solvent at a high speed, such that the ejected strand/fiber at least partially coats or is otherwise applied to a target surface. For example, the target surface may comprise a surface of a medical device component (e.g., stent/frame), which may be rotated as well to cover a varying surface area. Certain methods, devices, and systems relating to rotary jet spinning concepts that may be applicable to embodiments of the present disclosure are disclosed in U.S. Pat. No. 9,410,267, the disclosure of which is hereby incorporated by reference herein in its entirety for all purposes.

Rotary jet spinning systems and process can involve imparting rotational motion to a reservoir holding a polymer solution, the rotational motion causing the polymer to be ejected from one or more orifices in the reservoir. Such processes can further involve collecting the formed fibers on a holder having a desired shape to form micron-, submicron- or nanometer-dimensioned polymeric fibers as a covering for component(s) of a medical implant device component.

Figures 8A, 8B:
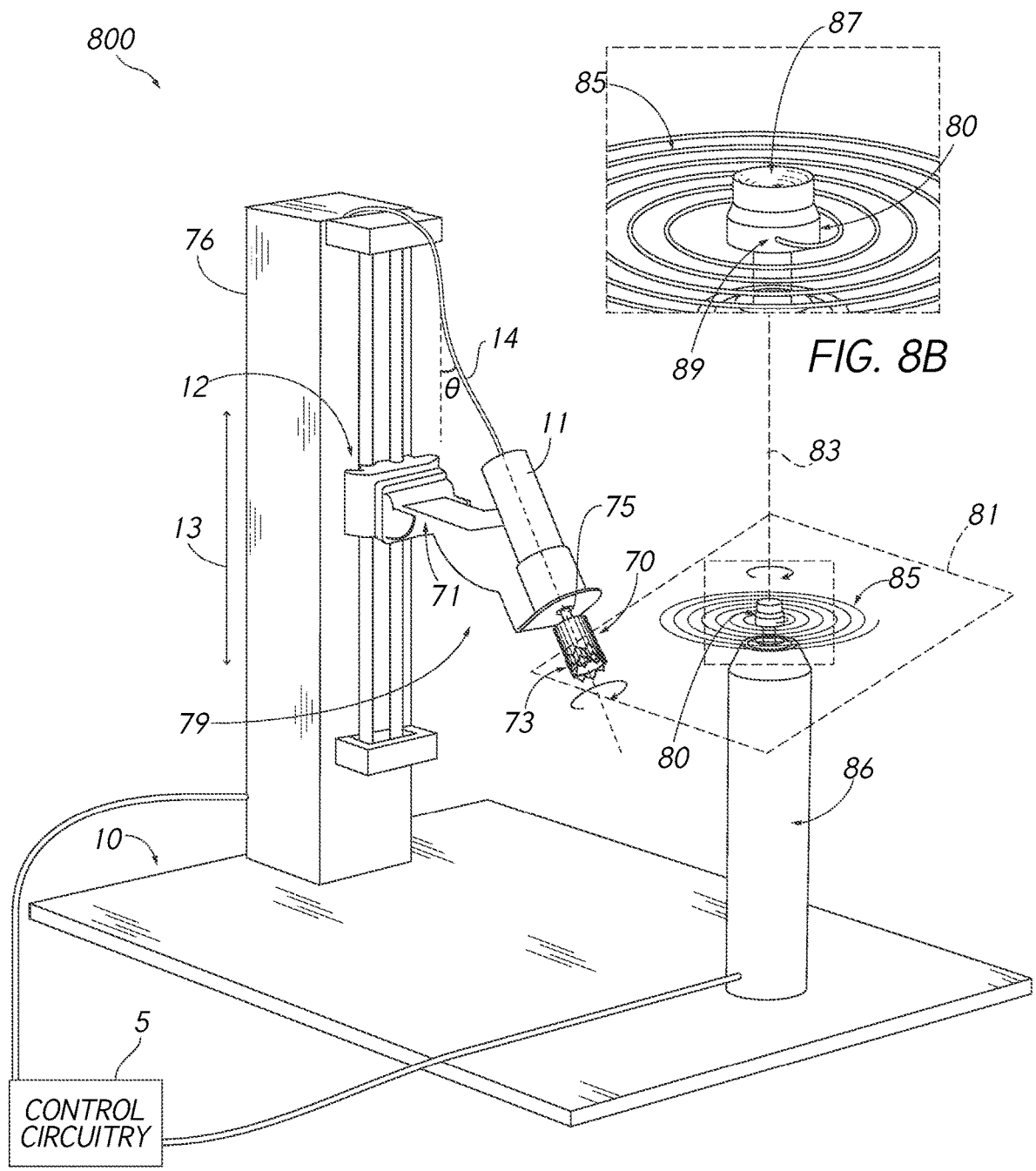
FIG. 8A shows a rotary jet spinning system for applying a fibrous material to a medical implant device component in accordance with one or more embodiments.
FIG. 8B is close-up view of a reservoir component of the system shown in FIG. 8A in accordance with one or more embodiments.

FIG. 8A shows a system 800 for applying a rotary jet spinning material 85 to a stent or other medical implant device component 73 coupled to a holder component 70 that is associated with a rotating mandrel 75. The system 800 may comprise a rotary motor (e.g., pneumatic motor) 86, which may be configured to drive the rotation of a reservoir 80. The reservoir 8o is shown in close-up in FIG. 8B. In some embodiments, the polymer solution is extruded through a small orifice 89. The extrusion of the solution can produce a plane 81 of fibers 85 into which the rotating holder 70 is translated into and out of during the collection process in a desired translation sequence.

The rotation of the mandrel 75 and holder 70 can be driven by a motor 11. Furthermore, the mandrel 75 and holder 70 may be mounted on a linear motor 12 configured to effect vertical translation of the mandrel 75 and holder 70. The motor 12 may be considered a fiber plane translation motor and may comprise, for example, a uniaxial high precision linear drive that is configured to translate the collector assembly 79 along an axis 13 parallel to the rotation axis 83 of the rotating reservoir 80, which corresponds to vertical translation with respect to the illustrated orientation of FIG. 8A. The axis 83 may be referred to as the deposition rotation axis. In some embodiments, one or more additional linear drives can be employed to translate the rotating mandrel 75 and holder 70 along one or more axes perpendicular to the rotation axis 83 of the rotating reservoir(s) (e.g., movement toward and away from the deposition rotation axis 83). In some embodiments, a multi-axial drive or a robotic arm could be employed for to provide increased flexibility in translation and/or changing an angular alignment of the holder 70.

The mandrel 75 and holder 70 can represent components of the collection assembly 79, at least part of which can be inserted into the path/plane 81 of the polymeric fibers 85. The axis 14 about which the mandrel/holder 70 is rotated may be referred to as the collection rotation axis, or mandrel/holder rotation axis. When the holder 70 is in the path/plane 81 of the polymeric fibers 85 ejected from the rotating reservoir 80, the polymeric fibers 85 can become wrapped around the holder 70 via rotation of the holder 70 about the collection rotation axis 14 as the holder 70 is translated along the axis 13.

In some embodiments, methods of depositing fibrous material on a medical implant device component involve feeding a polymer into the rotating reservoir 80 and generating rotational motion at a speed, and for a time, sufficient to form a micron-, submicron-, or nanometer-dimensioned polymeric fiber, and collecting the formed fibers on a medical implant device (not shown in detail; see FIGS. 10-40 for example embodiments of medical implant devices that may be mounted on, or otherwise secured by or held to, the holder 70) to form the micron-, submicron-, or nanometer-dimensioned polymeric fiber covering in the desired shape/configuration. In some embodiments, fibrous strands are produced by subjecting the polymer solution to a sufficient amount of pressure/stress for a time sufficient to form a fibrous covering on one or more components of a medical implant device in the desired shape and/or configuration. For example, a sufficient pressure/stress to produce fibrous strands from the polymer solution may be about 3,000 Pascals, or more.

In some embodiments, the system 800 is at least partially automated by control circuitry 5 configured to control one or more of the rotation rate of the reservoir 80, the rotation rate of the holder 70, and the linear and/or multi-dimensional translation of the holder 70 along the axis 13 parallel to the rotation axis 83 of the rotating reservoir and/or one or more other axes, through the generation and/or transmission of electrical signals to one or more components of the system 800.

Control over the rate of translation of the holder 70 along the axis 13 and/or the orientation of the collection axis 14 relative to the reservoir rotation axis 83 can provide at least partial control over the orientation of fibers deposited on the collection holder 70. For example, fibers may be collected on the holder 70 substantially parallel to the reservoir rotation axis 83, and with slow translation along the collection rotation axis 14. In some implementations, the rotation of the collection device (e.g., holder 70) may be opposite the rotation of the reservoir 80 (e.g., counter-clockwise and clockwise, respectively) or the rotation of the collection device 70 may be the same as the rotation of the reservoir 80 (e.g., both counter-clockwise). In some implementations, by slowly moving the collection device (e.g., holder 70) along the axis 13 through a path of the polymeric fibers 85 while rotating the collection device/assembly 70, completely aligned coverage of the holder and/or medical device component held thereby.

As shown in FIG. 8A, the collection rotation axis 14 may be oriented at an angle θ with respect to the deposition rotation axis 83. Such a configuration may result in fiber collection on the collection assembly 70 with crossed polymeric fibers. By increasing the speed of translation and/or rotating the holder 70 at a nonzero angle θ with respect to the deposition rotation axis 83, crossed weaves can be produced. The collection assembly 79 may be moved manually or mechanically.

In some embodiments, the system 800 includes a platform 10 for supporting the deposit of fibrous material, wherein the deposition assembly (80, 86) and the collection assembly (70, 71, 73, 76 11) are disposed vertically above the platform 10 and/or spaced from the platform 10 along the vertical axis 13. Sufficient rotational speeds and times for operating the rotating structure 80 to form a fiber may be dependent on the concentration of the material/solution and the desired features of the formed fiber. Exemplary speeds of rotation of the rotating structure may range from about 100 rpm to about 500,000 rpm, although rotational speeds are not limited to this exemplary range. Furthermore, the rotating structure 80 may be rotated to impact the liquid material for a time sufficient to form a desired fiber, such as, for example, an amount of time between about 1-100 minutes, or other intermediate times or ranges are also intended to be part of this invention. The force or energy imparted by the rotating structure 80 advantageously overcomes the surface tension of the solution and decouples a portion of the liquid material at a meniscus thereof and flings the portion away from the contact with the rotating structure and from a platform (not shown) on which the liquid is maintained, thereby forming fiber(s). The fiber(s) may be collected on the collection device 70. In some embodiments, the direction in which the liquid material is flung may be substantially the same as the tangential direction of motion of the rotating structure of the reservoir 80 that contacts the liquid material. In some embodiments, the rotating structure may impart a force to the liquid material in a substantially parallel direction to the top surface of the liquid material.

Any suitable size or geometrically-shaped reservoir 80 or collector 70 may be used for fabricating/collecting polymeric fibers. For example, the reservoir 80 may be tubular, conical, semilunar, bicuspid, round, rectangular, or oval. The holder 70 may be round, oval, rectangular, or a half-heart shape. The holder 70 may also be shaped in the form of any living organ, such as a heart, kidney, liver lobe(s), bladder, uterus, intestine, skeletal muscle, or lung shape, or portion thereof. The holder 70 may further be shaped as any hollow cavity, organ or tissue, such as a circular muscle structure, e.g., a valve, sphincter or iris.

The collection device 70 may be a holder configured in a desired shape and positioned in the path of the polymer ejected from the one or more orifices or in the path of the fibers flung from the rotating structure 80. In some embodiments, the collection device 70 may be disposed at a distance of about 2 inches (about 5 cm) to about 12 inches (about 30 cm) from the reservoir 80 from which the polymer is ejected. Certain exemplary distances may include, but are not limited to 2, 3, 4, 5, 6, 7, 8, 9, 10, 11, 12 inches (5, 7.6, 10.2, 12.7, 15.2, 17.8, 20.3, 22.9, 25.4, 27.9, 30 cm), and all intermediate numbers. This distance may be selected and/or configured to avoid formation of fibrous beads (which may occur if the collection device 70 is too close to the reservoir 80) and to achieve sufficient fibrous mass (which may not occur if the collection device is too far from the reservoir). In some implementations, formation of fibrous beads is implemented intentionally to provide desired fiber characteristics.

Figure 9:
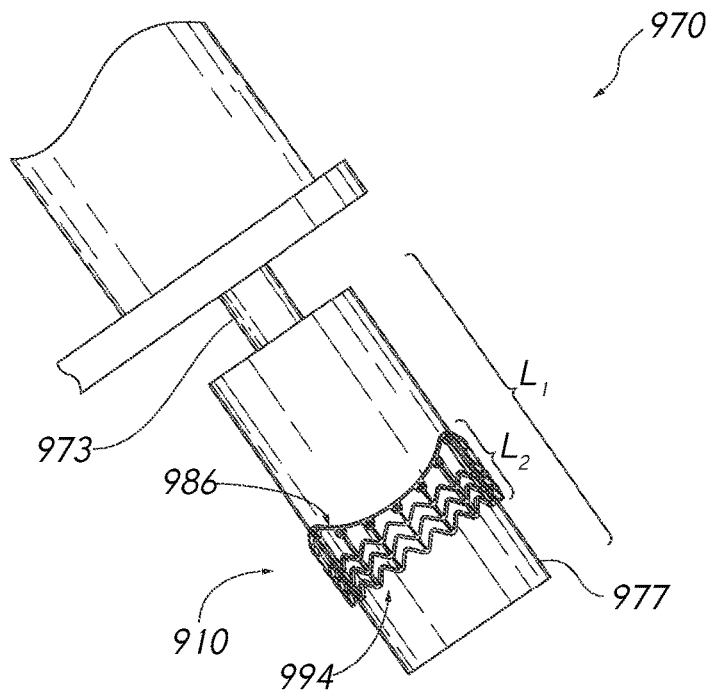
FIGS. 9 and 10 show side views of examples of collection assemblies comprising spacer-type and arm-type holders, respectively, in accordance with one or more embodiments.
Figure 10:
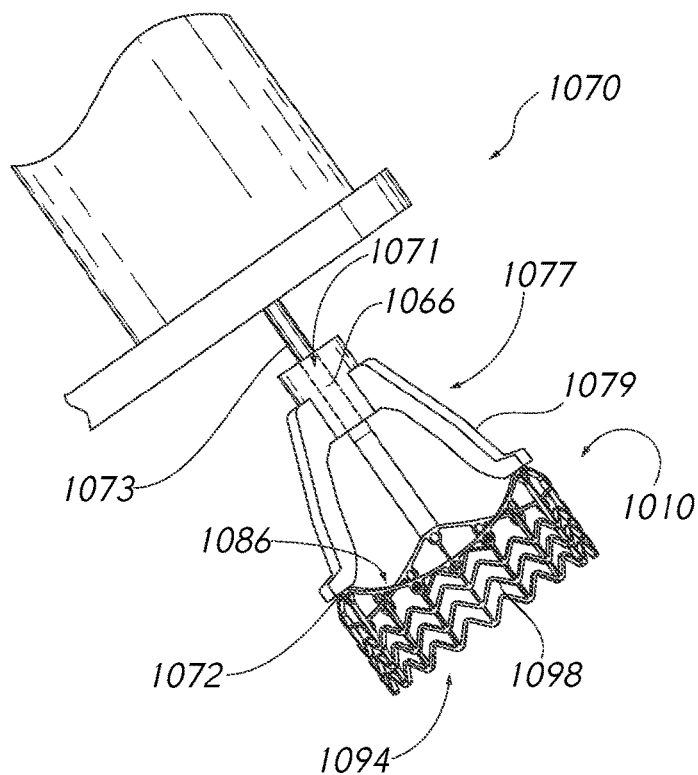

FIGS. 9 and 10 show side views of examples of collection assemblies comprising spacer-type (e.g., cylinder-form) and arm-type holders, respectively, coupled to a rotating mandrel (973, 1073) which may be coupled to one or more motion-generators for imparting rotational and/or linear motion to the mandrel and holder. Collection devices in accordance with embodiments of the present disclosure may be rotated about at speeds ranging from, for example, about 1,000 rpm to about 80,000 rpm, but are not limited to this exemplary range. For example, rotational speeds of collection devices may range from about 1,000 rpm-50,000 rpm, about 1,000 rpm to about 40,000 rpm, about 1,000 rpm to about 20,000 rpm, about 5,000 rpm to about 20,000 rpm, about 5,000 rpm to about 15,000 rpm, or about 50,000 rpm to about 400,000 rpm, and/or ranges and values intermediate to the above recited ranges and values.

An exemplary collection device, e.g., holder, may be linearly translated relative to the rotational axis 83 of the rotating reservoir 80 of the fiber formation system 800 (e.g., translated up and down along an axis 13 parallel to the rotation axis 83 of the rotating structure/reservoir 80 of the fiber formation system 800 or translated back and forth along an axis at an angle to the rotational axis of the rotating structure/reservoir) at linear speeds ranging from about 1 mm/s to about 300 mm/s. Ranges and speeds intermediate to the recited ranges and speeds are also contemplated by the present invention. In some embodiments, the rotating reservoir 80 of the fiber formation system 800 may also, or alternatively, be translated relative to the collection assembly 79 during collection of the fibers. The translation of the collection assembly 79 relative to the rotating reservoir 8o may bring the collection assembly 79 in and out of the plane 81 through which the flung or ejected fibers 85 travel (e.g., the fiber plane 81) to promote complete fiber coverage.

With further reference to FIGS. 9 and 10, example stents 910, 1010 are shown on the spacer-type (e.g., cylinder-form) 977 and arm-type 1077 holders, respectively, which may allow for application/deposition of fibrous material on the stents 910, 1010 using rotary jet spinning, as described in detail herein. In some embodiments, a stent can be formed of a biocompatible metal frame, such as stainless steel, cobalt-chrome alloy, or nitinol.

With respect to FIG. 9, the medical implant device 910 (e.g., stent) can be placed on the holder 977, which may have any suitable or desirable form or shape. In some embodiments, the device 910 is placed about a cylindrical holder having a length $L_1$ equal to or greater than an axial length $L_2$ of the implant device 910. In some embodiments, the length $L_1$ of the cylindrical holder is equal to or greater than twice the length $L_2$ of the implant device 910. Such a length of the cylindrical portion 977 may permit an invertible portion of fibrous covering (not shown) to extend beyond the implant device 910 in one or more directions by an amount sufficient to allow the excess portion of fibrous covering to be folded back onto an inner or outer surface of the implant device. That is, while the fibers are being applied to the implant device 910, the fibers may also layer over at least a portion of the holder 977 that supports the implant device 910. In some embodiments, the holder 977 and/or mandrel 973 may be shaped and configured such that at least a portion of the fibrous covering that extends axially beyond the implant device 910 forms a layer of fibrous material in the shape/form of a cylinder or cone. This cylinder/cone of polymeric material can then be used as an inner layer of material for the implant device 910 (e.g., stent) by folding or placing the material inside the stent. In some implementations, the folding/placement of the excess layer of fibrous material inside the implant device may be accomplished by moving the stent 910 with respect to the holder 977, which may at least partially invert the cylinder/cone of fibrous material and wrap it in toward the inner surface of the implant device. In this way, both the inner and outer surfaces of the implant device may be fully encased with fibrous material without the need for applying and sewing a pre-made polymeric cloth.

The holder 977 may be threaded onto the mandrel 973. For example, the holder 977 can have an internal bore (not shown) through which the mandrel 973 may be threaded. The holder 977 can comprise any suitable material, including but not limited to metal, such as stainless steel, ceramic, or polymer. In some embodiments, the holder 977 includes a 3D-printed polymer fixture or a balloon. The holder 977 advantageously has a diameter less than that of the implant device 910. For example, the holder 977 may have a cylinder form having a diameter that is greater than the diameter of the mandrel 973 and slightly less than the internal diameter of the implant device 910. In some embodiments, the holder 977 comprises a lubricious coating, which can facilitate axial movement of the implant device 910 on the holder 977.

In some implementations, the cylinder form of the holder 977 may be coated with a fibrous layer, which may be applied through rotary jet spinning, that extends beyond the implant device 910 on the cylinder by an amount sufficient to allow the excess portion of the fibrous layer to be folded back onto the outer surface of the implant device 910, producing a second layer of fibrous material covering the outer surface of the implant device 910 when implemented as described below. For example, the fibrous layer may be applied to the cylinder 977, after which the implant device 910 may be placed on the cylinder. Subsequent folding of the fibrous layer over the outer portion of the implant device 910 can result in at least a portion of both the inner portion and the outer portion of the implant device 910 being covered by fibrous material. In some embodiments, the holder 977 is integrated with the mandrel 973. For example, the holder 977 and the mandrel 973 can be embodied in a unitary form.

In FIG. 10, the holder 1077 is attached to the rotating mandrel 1073 in such a way as to translate rotation of the mandrel 1073 to rotation of the holder 1077. With respect to FIGS. 9 and 10, the mandrels 973, 1073 may comprise a stainless-steel rod. The rod may be approximately 3 mm in diameter, although mandrels of different diameters and materials may alternatively be used. The mandrels 973, 1073 advantageously have a diameter that is less than the diameter of the stents 910, 1010.

The holder 1077 can include any number of arms 1079 or other attachment members, which can be secured in any suitable or desirable way to the implant device 1010 (e.g., stent). In the illustrated embodiments of FIGS. 9 and 10, the medical implant devices 910, 1010 can comprise a stent having a first end 986, 1086 that follows a generally circular, undulating path having alternating arcuate troughs and pointed peaks that generally correspond to the undulating contour of the underside of a sewing ring (not shown) for use as part of a prosthetic heart valve. A second end 994, 1094 of the stent can substantially form a circle without undulations. A mid-section of the stent may be made up of one or more rows of expandable struts 998, 1098 extending circumferentially in a sawtooth or chevron pattern between axially-extending struts.

The holder 1077 is used to hold the implant device (e.g., stent) 1010. In some embodiments, the holder includes a central hub portion 1066, which may have a generally tubular form, and a plurality of stabilizing arms 1079 projecting axially and radially outward therefrom. In the embodiment shown, the holder 1077 has three stabilizing arms 1079, although a holder having greater or fewer stabilizing arms may be used. The central hub portion 1066 can have an internal bore 1070. The holder 1077 may be formed of a rigid polymer, such as acetal (DELRIN® polymer, DuPont), nylon, polypropylene, or the like. In some embodiments, the holder 1077 is integrated with the mandrel 1073. For example, the holder 1077 and the mandrel 1073 can be embodied in a unitary form. In some implementations, the medical implant device 910 is directly secured to the stabilizing arms 1079 of the holder 1077 using sutures or other attachment means or mechanism at commissure ends or other attachment features 1072 of the medical implant device 1010. Example attachment means or mechanisms for attaching/coupling the implant device 1010 to the holder 1077 include, but are not limited to, one or more pins, clips, clamps, tabs, adhesive elements, hooks, or other structurally- or frictionally-based attachment features.

The holder 1077 may be threaded onto the mandrel 1073 via, for example, the internal bore 1070 of the holder 1077. In some embodiments, the holder 1077 (and medical implant device 1010) may be left free to translate along an axis of the mandrel 1073. In some embodiments, the holder 1077 may be secured to the mandrel 1073, for example, mechanically or adhesively using an adhesive element, or other attachment means as described herein. Examples of suitable adhesive elements in accordance with aspects of the present disclosure can comprise epoxy, adhesive tape, and/or the like. Although a single holder device 1077 is shown in FIG. 10, other embodiments may include additional/secondary holders and/or other support frames.

Figure 11:
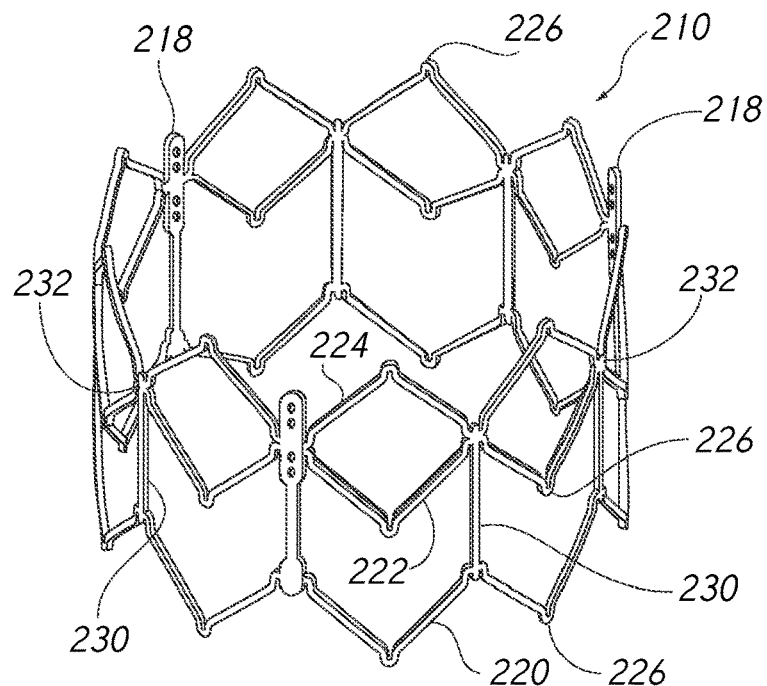
FIG. 11 illustrates an example stent that may be used in a prosthetic heart valve implant device in accordance with one or more embodiments.

Various medical device components may advantageously be at least partially covered in fibrous material, as described herein. For example, with respect to prosthetic heart valve implant devices, a fibrous sealing and/or skirt portion can be sutured to a frame of a prosthetic heart valve to help prevent blood from leaking around the outer edges or circumference of the prosthetic heart valve. FIG. 11 illustrates an example stent 210 that may be used in a prosthetic heart valve implant device in accordance with one or more embodiments of the present disclosure. The stent 210 may be made from laser-cut tubing of a plastically-expandable metal or other at least partially rigid material. In some implementations, the stent frame 210 may further be treated to be at least partially self-expanding. Although a laser-cut stent is shown, it should be understood that the fiber-application processes and devices disclosed herein apply to other types of stents as well, including stents comprising rigid rings, spirally-wound tubes, and other tubes/conduits that fit within, for example, a heart valve annulus and that define an orifice therethrough for the passage of blood.

The stent 210 may be at least partially self-expanding and/or may be mechanically expandable (e.g., balloon-expandable). For example, a self-expanding stent may be crimped or otherwise compressed into a small tube and may possess sufficient elasticity to spring outward by itself when a restraint, such as an outer sheath/catheter, is removed. In contrast, a balloon-expanding stent may comprise material that is relatively less elastic and is capable of plastic expansion from the inside-out when converting the stent from a contracted diameter/configuration to an expanded diameter/configuration. The plastic expansion may be accomplished with a balloon or other device, such as a device with mechanical fingers. With such balloon-expanding stents, the stent frame may plastically deform after the application of a deformation force, such as an inflating balloon or expanding mechanical fingers.

The stent 210 (e.g., self-expanding stent or balloon-expanding stent) may be used as part of a prosthetic heart valve having a single-stage implantation in which a surgeon secures a heart valve having a fibrous anchoring skirt and valve member to a heart valve annulus as one unit or piece. Certain stent solutions for aortic valve replacement in accordance with some embodiments of the present disclosure are disclosed in U.S. Pat. No. 8,641,757, which is incorporated herein by reference in its entirety for all purposes. In some implementations, an exemplary delivery system advances the valve implant device with the stent at the leading or distal end until it is located within the valve annulus and/or left ventricular outflow tract, at which point a balloon can inflate to expand the stent against the aortic annulus and/or ventricular tissue.

In the illustrated embodiment of Figure ii, the stent frame 210 is generally annular and/or cylindrical in shape and includes a plurality of angularly-spaced, vertically-extending, commissure attachment posts, or struts, 218. Posts 218 can be interconnected at least by a lower row of circumferentially-extending struts 220 and one or more upper rows of circumferentially extending struts 222 and 224, respectively. The struts in each row can be arranged in a zig-zag or generally saw-tooth-like pattern extending in the direction of the circumference of the frame, as shown. Adjacent struts in the same row can be interconnected to one another to form an angle between about 90-110 degrees. The angle between adjacent struts can be selected to optimize the radial strength of the frame 210 when expanded yet still permit the frame 210 to be evenly crimped and expanded.

In the illustrated embodiment, pairs of adjacent circumferential struts in the same row are connected to each other by a respective, generally U-shaped crown structure or portion 226. The crown structures 26 can each include a horizontal portion extending between and connecting the adjacent ends of the struts such that a gap is defined between the adjacent ends and the crown structure connects the adjacent ends at a location offset from the strut's natural point of intersection. The crown structures 226 can significantly reduce residual strains on the frame 210 at the location of the struts 220, 222, 224 during crimping and expanding of the frame 210. Each pair of struts 222 connected at a common crown structure 226 may generally form a cell with an adjacent pair of struts 224 in the row above. Each cell can be connected to an adjacent cell at a node 232. Each node 232 can be interconnected with the lower row of struts by a respective vertical (axial) strut 230 that is connected to, and extends between, a respective node 232 and a location on the lower row of struts 220 where two struts are connected at their ends opposite of a crown structures 226.

In certain embodiments, lower struts 220 have a greater thickness or diameter than upper struts 222, 224. In one implementation, for example, lower struts 220 have a thickness of about 0.42 mm and upper struts 222, 224 have a thickness of about 0.38 mm. In the particular embodiment of FIG. 11, because there is only one row of lower struts 220 and two rows of upper struts 222, 224, enlargement of the lower struts 220 with respect to the upper struts 222, 224 can advantageously enhance the radial strength of the frame 210 at the lower area of the frame and/or allow for more uniform expansion of the frame. Columns of the frame 210 can be defined by the adjoining pairs of struts 220, 222, 224 extending between two axially-extending struts 230. In some embodiments, the frame 210 comprises three 120-degree segments, with each segment being bounded by two posts 218. Accordingly, the frame 210 of the particular embodiment of FIG. 11 includes 9 total columns. In some embodiments, the number of columns and rows may be desirably minimized to reduce the overall crimp profile of the frame 210 and/or associated valve.

Figure 12:
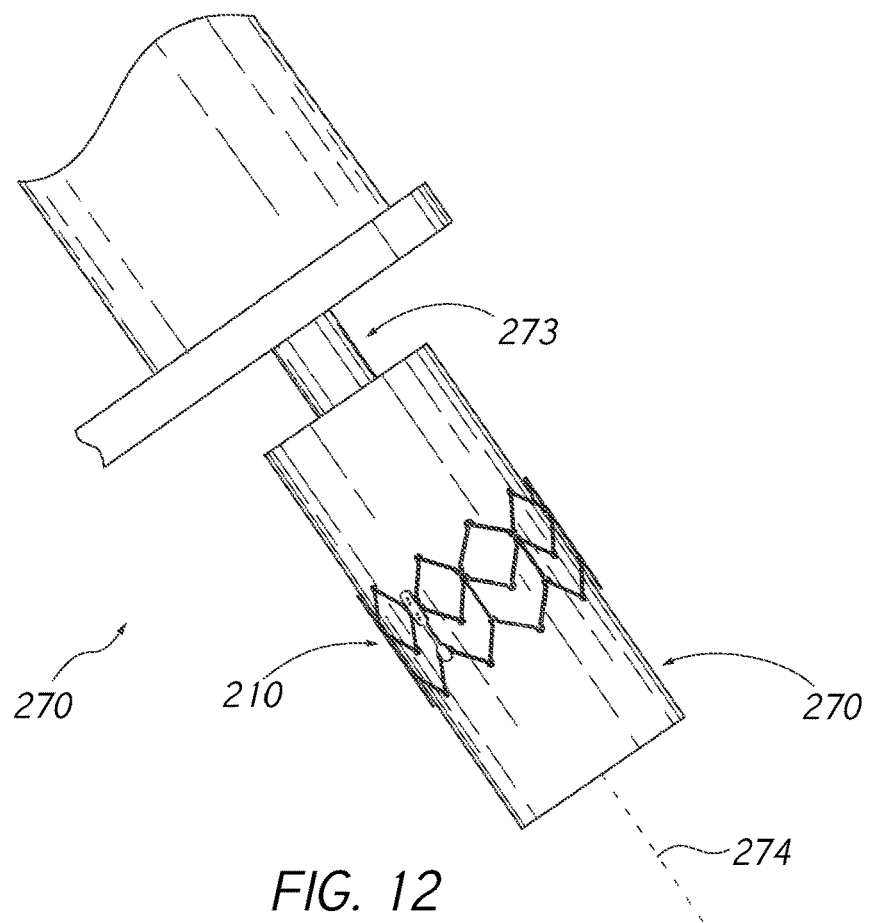
FIG. 12 shows a stent disposed about a spacer-form holder in accordance with one or more embodiments.

FIG. 12 shows the heart valve stent 210 disposed about a spacer-form holder 277, such as a cylinder-type holder as described herein. Although a spacer-form holder is shown in FIG. 12, it should be understood that any type of holder may be used to hold the stent 210, including holders having arms or other attachment features, as described herein. The mandrel 273 and holder 277 can be part of a collector assembly 270, as described in detail herein.

With the stent 210 disposed on the holder 277, the mandrel 273 and coupled holder 277 can be rotated about the axis 274 defined by the mandrel 273. For example, the collector assembly 270 can comprise a rotor motor configured to rotate the mandrel 273. The various components of the collector assembly 270 may be controlled at least in part by control circuitry of a local and/or remote controller system.

Fibrous material may be applied to the stent 210 and/or holder 277 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the outer surface of the stent 210 and to at least a portion of the holder 277 to form a layer of fibrous material 202, as shown in FIG. 13.

The application of the rotary-jet-spun fibrous material may produce a first portion 201 of the layer of fibrous material 202 on the outer surface of the stent 210 and a second portion 203 of the layer of fibrous material on the outer surface of the holder 277. In some implementations, a cone form (not shown) of the fibrous material 202 forms and extends between the proximal end 209 of the holder 277 and the mandrel 273.

After application of the fibrous material 202 to the stent 210, the stent 210 and/or additional fibrous material deposited on the holder may be withdrawn from the collection assembly 270. The removal of the surplus portion 203 of the layer of fibrous material 202 may be accomplished, for example, by cutting the layer of fibrous material at or near the mandrel 273. At least a portion of the second portion 203 of the fibrous material may be folded under the stent 210 to provide a two-sided covering of the stent 210. In some implementations, application of the surplus fibrous material can be accomplished simply by moving the stent 210 relative to the holder 277 and allowing the surplus portion to become inverted between the stent 210 and the holder 277. In some implementations, application of the surplus fibrous material to the inside of the stent 210 is performed manually and/or using one or more tools. Processes of depositing fibrous material on a medical device can be performed as many times as desired and/or for the desired amount of time in order to produce the desired thickness of fibrous material.

Figure 13:
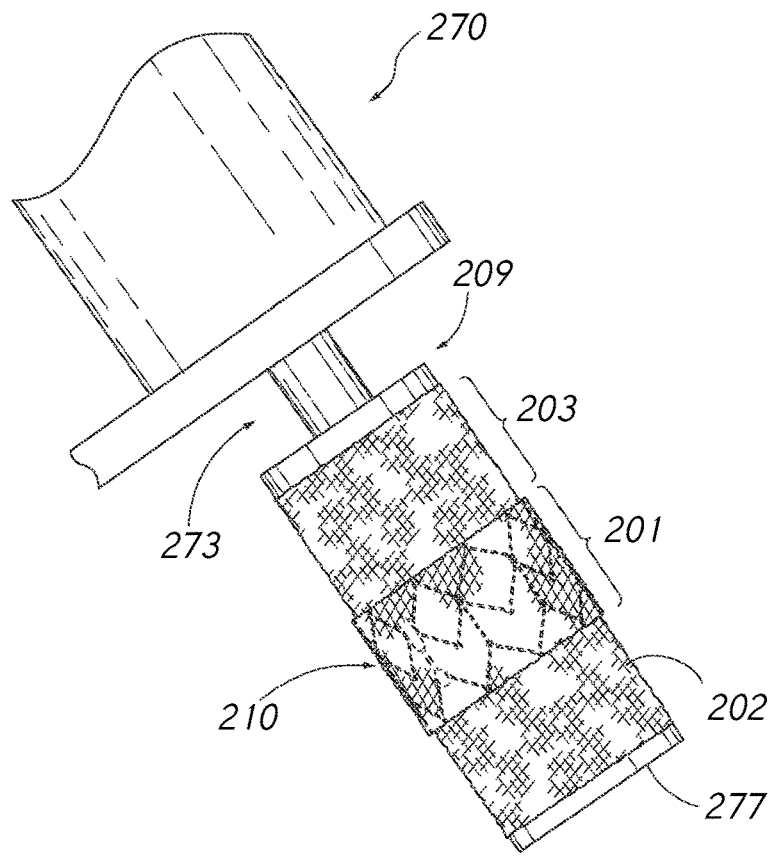
FIG. 13 shows a stent disposed about a holder and covered at least partially with fibrous material using a rotary jet spinning deposition system in accordance with one or more embodiments.
Figure 14:
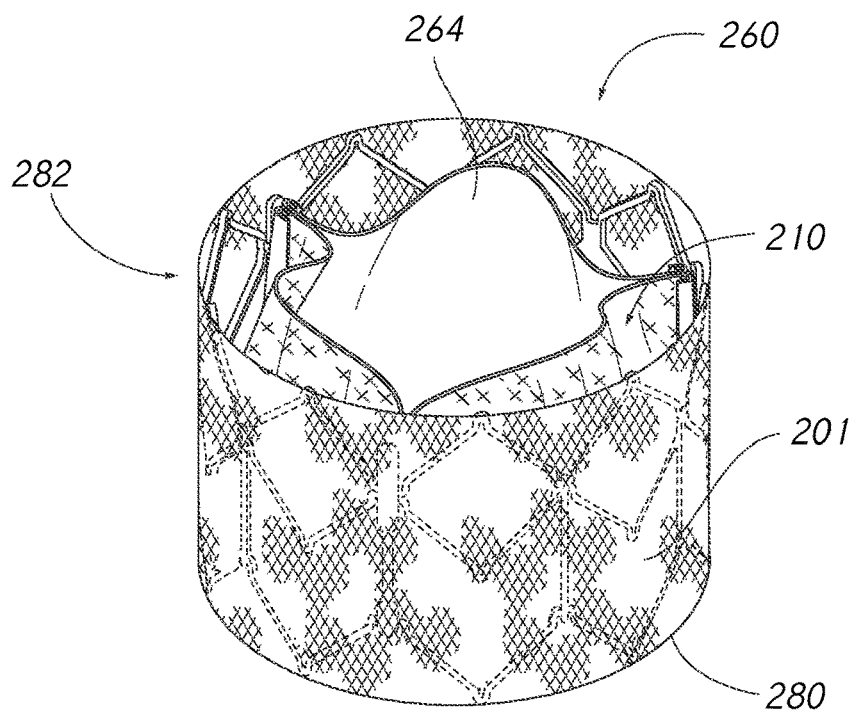
FIG. 14 illustrates a frame incorporated in an implantable prosthetic valve in accordance with one or more embodiments.

FIG. 14 illustrates the frame 210 of FIGS. 11-13 incorporated in an implantable prosthetic valve 260 in accordance with one or more embodiments. As assembled, the valve 260 in the illustrated embodiment includes a leaflet structure 264 supported by the stent frame 210, which includes a fabric skirt 201 applied to the stent frame 210 using rotary jet spinning technology as described above. The valve implant device 260 can be suitable for implantation in the annulus of a native aortic valve, for example, but also can be adapted to be implanted in other native valve annuluses of the heart or in various other ducts or orifices of the body. The valve implant device 260 has a "lower" end 280 and an "upper" end 282. In the context of the present application, the terms "lower" and "upper" are used interchangeably with the terms "inflow" and "outflow," respectively, in some contexts. Thus, for example, the lower end 280 of the valve may be considered the inflow end and the upper end 282 of the valve may be considered the outflow end.

The valve implant device 260 and stent frame 210 are configured to be radially collapsible to a collapsed or crimped state for introduction into the body within a delivery catheter and radially expandable to an expanded state for implanting the valve 260 at a desired location in the body (e.g., the native aortic valve). For example, the stent frame 210 can be made of a plastically-expandable material that permits crimping of the valve to a smaller profile for delivery and expansion of the valve using an expansion device, such as the balloon of a balloon catheter. Alternatively, the valve implant device 260 can be a self-expanding valve, wherein the frame is made of a self-expanding material such as a shape memory metal (e.g., nitinol). A self-expanding valve can be crimped to a smaller profile and held in the crimped state with a restraining device, such as a sheath covering the valve. When the valve is positioned at or near the target site, the restraining device may be removed to allow the valve to self-expand to its expanded, functional size.

Figure 15:
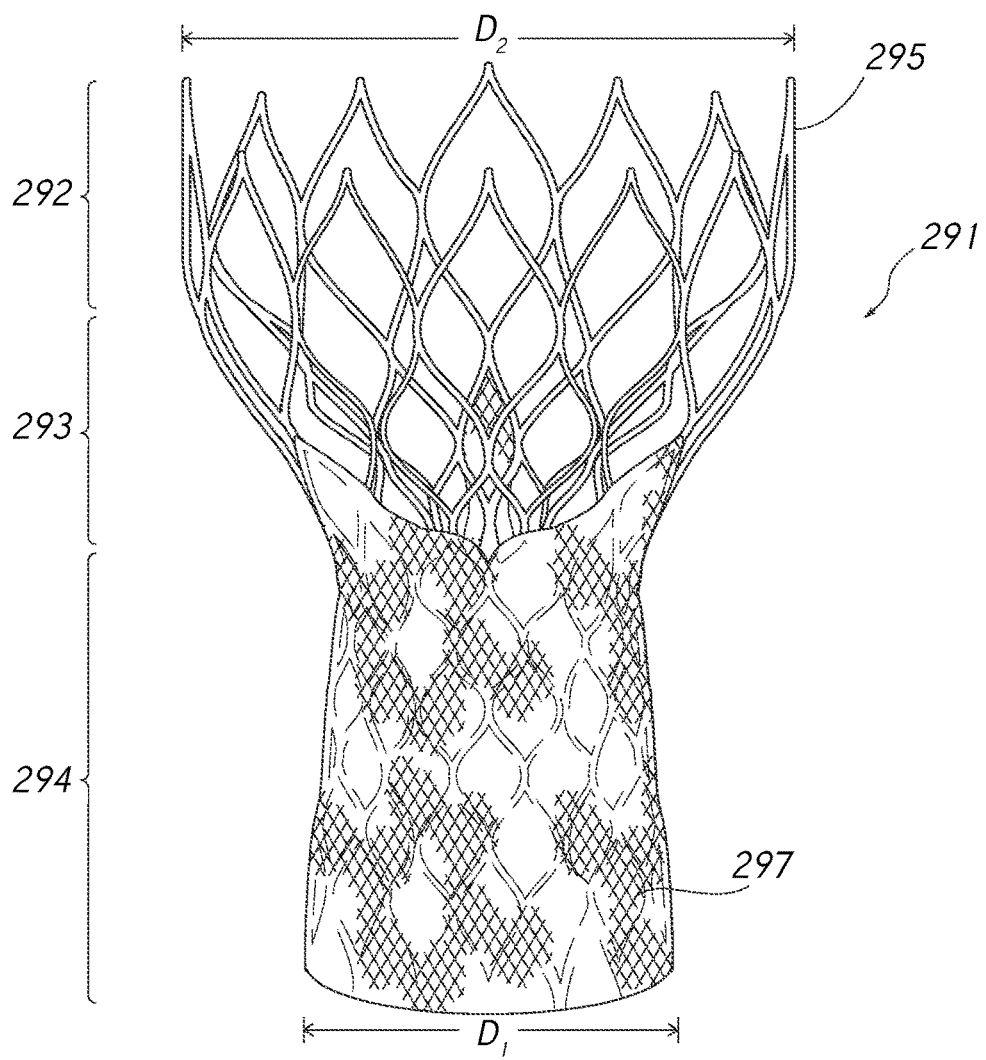
FIG. 15 shows an example heart valve implant device including a stent that has fibrous material applied to one or more portions thereof using a rotary jet spinning process in accordance with one or more embodiments.

Although FIGS. 11-14 show components for a transcatheter heart valve and associated stent having a particular form and features, it should be understood that the rotary jet spinning processes and systems described herein are suitable for application of fibrous material to stents and/or valve devices having any suitable or desirable form and/or features. FIG. 15 shows an example heart valve implant device 291 including a stent 295 that has fibrous material applied to a portion thereof using a rotary jet spinning process in accordance with embodiments of the present disclosure. Unlike the stent 210 of FIGS. 11-14, the stent 295 does not have uniform cross-sectional shape or diameter along a length thereof. For example, the stent 295 includes a lower end having a diameter D1 that is less that the diameter D2 at an upper end, as shown. In some embodiments, the stent 295 may have one or more tapered longitudinal portions 294, 293, and/or 292, as illustrated. The tapered portion(s) can bridge between smaller and larger diameters of the stent 295.

Due to the tapered (e.g., hour-glass) shape of the stent 295, the holder used to apply the fibrous material 297 to the stent 295 may advantageously be configured to accommodate such shape at least in part. For example, a holder device may be used that has non-cylindrical shape over at least a portion of the longitudinal area thereof. In some embodiments, a holder having one or more arm support members may be used, or alternatively, a spacer-type holder device may be used that has an at least partially tapered shape or portion to match or accommodate at least the portion 294 of the stent 295 that is to be covered with fibrous material. In some embodiments, an at least partially conical holder may be used for a device similar to the device 291 of FIG. 15. In some implementations, fibrous material may be applied to the stent 295 over one or more longitudinal portions thereof, whereas one or more portions (e.g., 292, 293) may be left uncovered.

Figure 16:
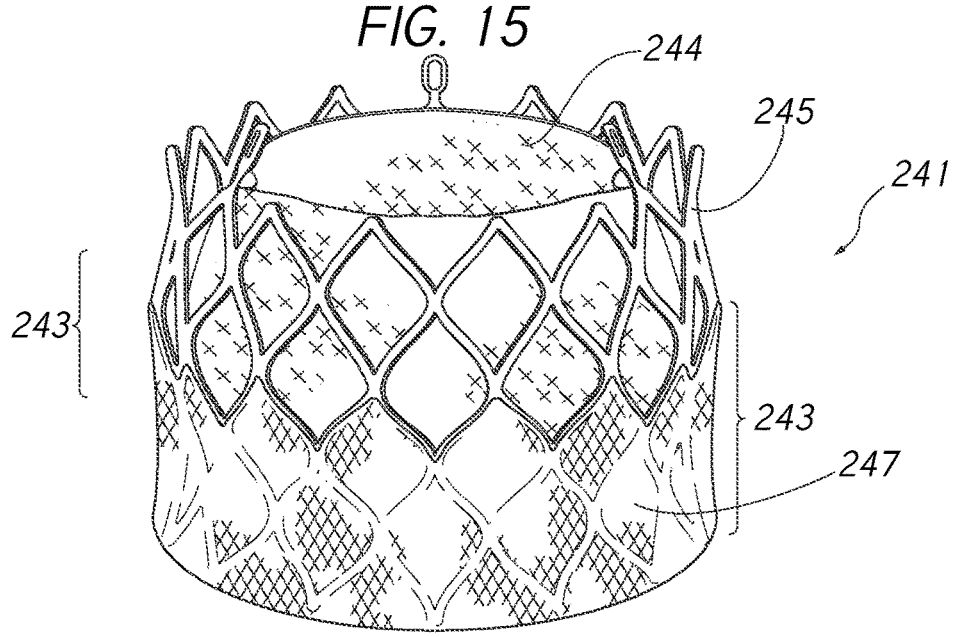
FIG. 16 shows an example of a heart valve implant device having non-uniform stent diameter that has fibrous material applied to one or more portions thereof using a rotary jet spinning process in accordance with one or more embodiments.

FIG. 16 shows another example of a heart valve implant device having non-uniform stent diameter with respect to the stent component 245. As shown, at least a portion 243 of the stent 245 may advantageously be covered with fibrous material using rotary jet spinning, as described in detail herein. In some embodiments, the stent 245 can have one or more bulge features 242, which may advantageously be configured to accommodate certain cardiac anatomy associated with a target implantation site. The valve device 241 further includes a plurality of leaflets 244. In some embodiments, the valve device 241 is a replacement aortic valve implant device.

The stent 245 may be attached to any type of holder for application of the fibrous material 247 using a rotary jet spinning system and/or process. For example, a holder having one or more arm support members may be used, or alternatively, a spacer-type holder device may be used that has an at least partially angled or tapered shape or portion to match or accommodate at least the portion 243 of the stent 245 that is to be covered with fibrous material.

Figure 17:
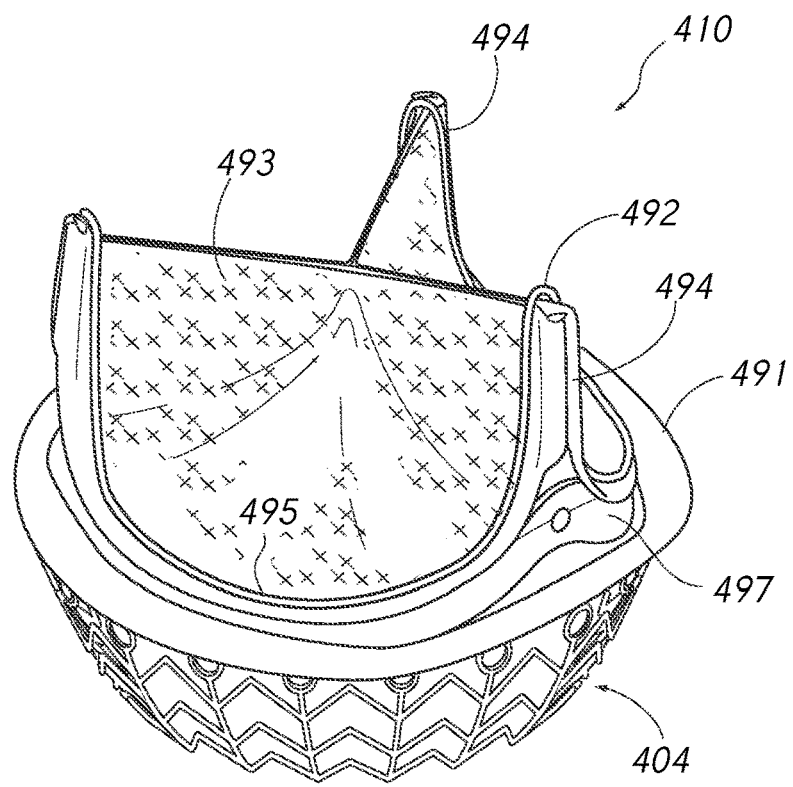
FIG. 17 is a perspective view of a prosthetic heart valve implant device in accordance with one or more embodiments.

In addition to transcatheter heart valve and stent components, other types of prosthetic heart valve implant devices can include component(s) that are desirably at least partially covered in fibrous material using rotary jet spinning processes, as described herein. For example, FIG. 17 is a perspective view of a prosthetic heart valve implant device 410 in accordance with one or more embodiments. The heart valve 410 can include a peripheral sealing ring structure 491 configured to provide support for nesting the heart valve 410 in a heart valve cavity and/or resting upon, or attaching to, an annulus or other cardiac structure/anatomy. The valve 410 further includes a frame member 492, such as a metal frame, which can provide support for a plurality of flexible leaflets 493 and defines three upstanding commissure posts 494, wherein the leaflets 493 are supported between the commissure posts 494. The heart valve 410 is illustrated in a closed position in which fluid flow through the valve is inhibited; when in an at least partially-open state, fluid (e.g., blood) can flow in one direction through an inner channel of the valve that is formed when the leaflets 493 separate.

The valve leaflets 493 can comprise three separate flaps of tissue, such as xenograft tissue (e.g., bovine pericardium), or all three leaflets can be derived from a single xenograft valve (e.g., a porcine valve). The leaflets 493 can be secured and supported both by the commissure posts 494, as well as along arcuate cusps 495 of the frame member between the commissure posts. In some embodiments, the leaflets 493 are matched for thickness and/or elasticity in order to desirably occlude fluid flow through the valve 410. The leaflets 493 extend inward from the surrounding frame 492 into a flow orifice defined thereby. In certain embodiments, the leaflets 493 curve toward the outflow direction and "coapt" in the middle of the valve orifice to facilitate one-way flow through the valve 410.

The frame member 492 can comprise an at least partially flexible wireform made of metal alloy or other metal or at least partially rigid material. In some embodiments, the frame member 492 is configured to reduce loading shock on the leaflets 493 during the cardiac cycle. The sealing ring 491 can attach around the periphery of the frame member 492 at the inflow end of the valve, with the commissure posts 494 projecting in the outflow direction. The frame member 492 can be generally rigid and/or expansion-resistant in order to substantially maintain a particular shape and diameter of the valve orifice and also to maintain the valve leaflets 493 in proper alignment in order for the valve to properly close and open. Although a substantially round embodiment is depicted in FIG. 17, other shapes are also within the scope of the invention, depending on the particular application (e.g., the particular native valve to be replaced, etc.).

The valve device 410 can further include a support structure 497 designed to fit above the sealing ring 491. In certain embodiments, the support structure 497 is made of metal and/or plastic (e.g., polyester, polyethylene terephthalate (PET), or biaxially-oriented PET, for example, MYLAR PET, DuPont Teijin Films) component(s), wherein the leaflets 493 can be sewn or otherwise attached to, for example, a plastic band component of the support structure 497. The support structure 497 can comprise a rigid stiffening band, which can be comprised of, for example, metal or other rigid material. The support structure 497 can include commissure support portions that extend vertically with respect to the illustrated orientation of FIG. 17, which can fit at least partially within the upwardly-projecting commissure regions 494 of the frame member 492.

The sealing ring 491 of the heart valve implant device 410 can be configured to at least partially stabilize the annulus and to support the functional changes that occur during the cardiac cycle, such as by maintaining coaptation and valve integrity to prevent reverse flow while permitting good hemodynamics during forward flow. The sealing ring 491 can comprise an inner at least partially rigid substrate (e.g., metal such as stainless steel or titanium, or a flexible material such as silicone rubber or PET cordage). The sealing ring 491 can be stiff or flexible, can be split or continuous, and can have a variety of shapes, including circular, D-shaped, kidney-shaped, or C-shaped. In certain embodiments, when implanted, suture fasteners (not shown) can be distributed around the sealing ring 491 that bind the sealing ring to the attachment tissue of the patient.

In some embodiments, the valve 410 further comprises a sub-annular frame 404. The frame 404 can provide improved support and/or sealing functionality when implanted in, for example, an aortic valve annulus. The frame 410 may be made from laser-cut tubing of a plastically expandable metal or other at least partially rigid material. In some implementations, the frame 410 may further be treated to be at least partially self-expanding. Although a laser-cut sub-annular frame is shown, it should be understood that the fiber-application processes and devices disclosed herein apply to other types of frames as well, including frames comprising rigid rings, spirally-wound tubes, and other tubes that fit within, for example, a heart valve annulus and that define an orifice therethrough for the passage of blood.

Figure 18:
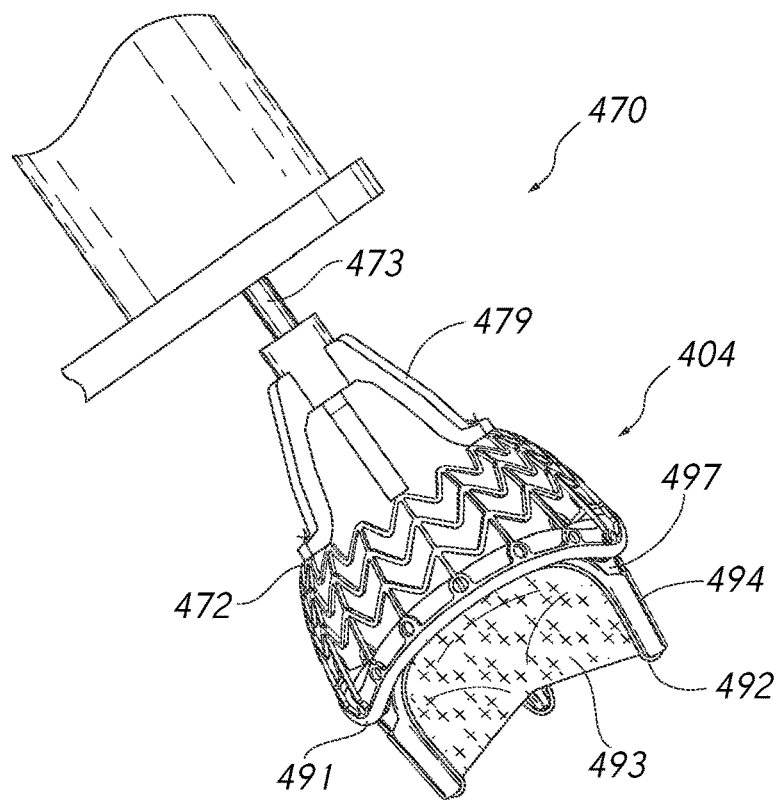
FIG. 18 shows a heart valve assembly disposed on a holder in accordance with one or more embodiments.

FIG. 18 shows the heart valve assembly 410 disposed on a holder 479, such as an arm-type holder as described herein. Although an arm holder is shown in FIG. 18, it should be understood that any type of holder may be used to hold the valve 410, including cylindrical or other-shaped spacer-type holders or other attachment features, as described herein. The mandrel 473 and holder 479 may be part of a collector assembly 470, as described in detail herein.

With the valve assembly 410 disposed on the holder 479, the mandrel 473 and coupled holder 479 can be rotated about the axis defined by the mandrel 473. For example, the collector assembly 470 can comprise a rotor motor configured to rotate the mandrel 473. The various components of the collector assembly 470 may be controlled at least in part by control circuitry of a local and/or remote controller system.

Figure 19:
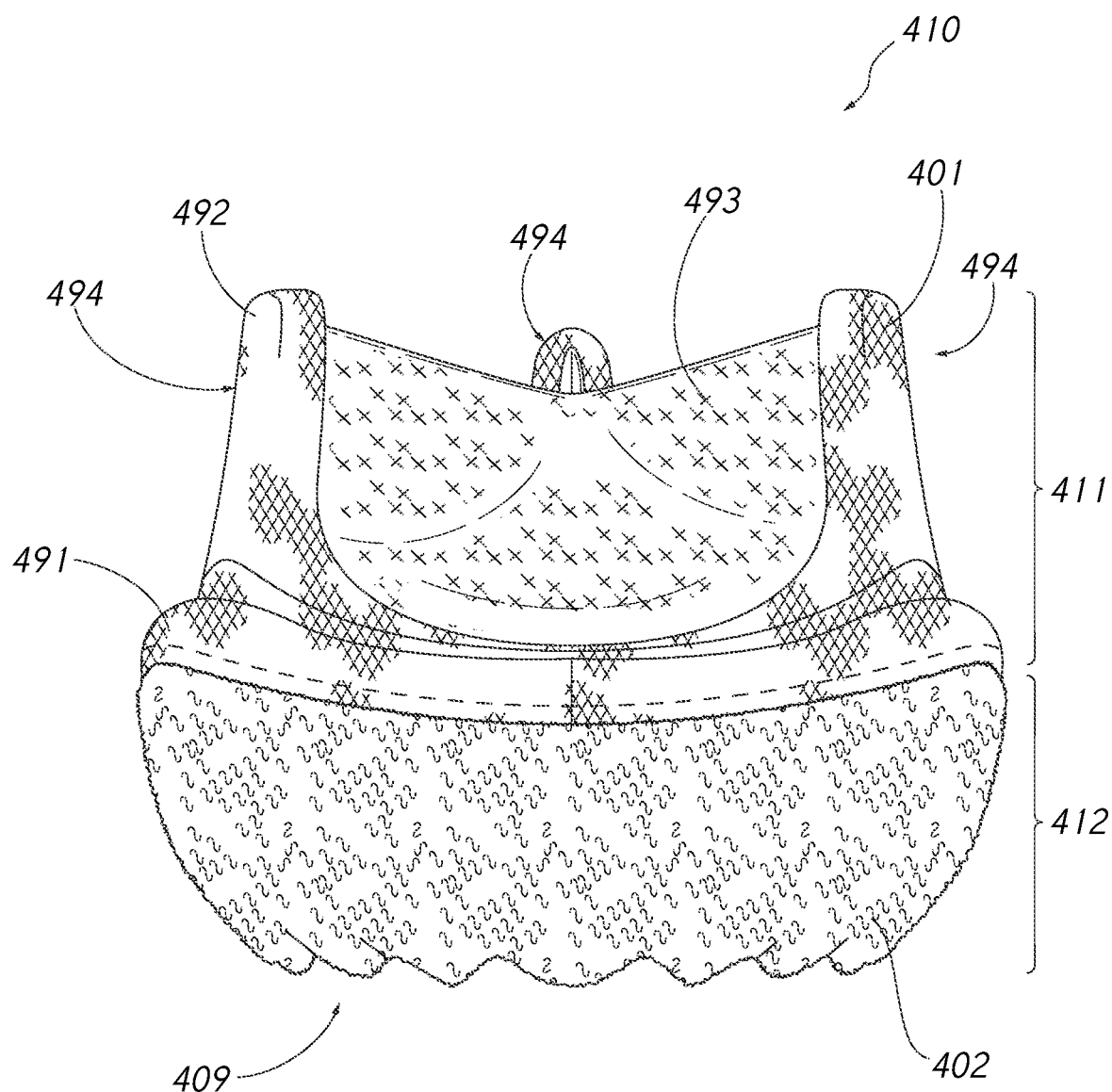
FIG. 19 shows a surgical heart valve having fibrous material applied to portions thereof using rotary jet spinning in accordance with one or more embodiments.

Fibrous material may be applied to the valve assembly 410 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the outer surface of the frame 492, sealing ring 491, and skirt frame 404 to form one or more layers of fibrous material, as shown in FIG. 19. Although FIG. 18 shows the leaflets 493 attached to the valve assembly 410, in some implementations, the fibrous material may be applied to the valve frame assembly 410 prior to application of the valve leaflets 493. In certain preferred embodiments, valve leaflets are applied/attached after the relevant rotary jet spinning process(es) for application of fibrous material. In some implementations, some and/or each component requiring fibrous material coating/application (e.g. 404, 494, 491) can be processed using rotary jet spinning for application of fibrous material thereto individually.

FIG. 19 shows a surgical heart valve having fibrous material applied to portions thereof using rotary jet spinning in accordance with one or more embodiments of the present disclosure. The fiber-covered peripheral sealing ring structure 491 can be configured to provide support for nesting the heart valve 410 in a heart valve cavity and/or resting upon, or attaching to, an annulus or other structure of the heart. The fiber-covered frame member 492 provides support for the plurality of flexible leaflets 493 and defines the upstanding commissure posts 494, wherein the leaflets 493 can be supported between the commissure posts 494. The sealing ring 491 can be attached around the periphery of the frame member 494 towards the inflow end of the valve 410, with the commissure posts 494 projecting in the outflow direction. The leaflets 493 can be formed from separate flaps of material or tissue, such as, for example, xenograft tissue (e.g., bovine pericardium), or the leaflets 493 can be derived from a single xenograft valve (e.g., a porcine valve). The leaflets 493 can be secured and supported both by the commissure posts 494, as well as along arcuate cusps of the frame member between the commissure posts.

Rotary jet spinning can be used to apply fibrous material 401 having a first set of characteristics to a first portion 411 of the valve assembly 410, such as to the commissure posts 494 and/or sealing ring 491, whereas fibrous material 402 having a second set of characteristics is applied to a second portion 412 of the valve assembly 410. For example, the fibrous material 401 may be relatively smooth, whereas the fibrous material 402 may be relatively textured to provide a secure fit in the valve annulus to aid sealing. The fibrous material 401 and/or fibrous material 402 may comprise polymetric fibrous material, as described in detail herein. Processes of depositing the fibrous material 401 and/or 402 can be performed as many times as desired and/or for the desired amount of time in order to produce the desired thickness of fibrous material.

The frame 494 can be covered with the fibrous material 401 using rotary jet spinning process(es). In some implementations, the fibrous material 401, after rotary jet spinning application thereof, can be sutured in one or more portions to secure the fibrous material 401 as a covering for the frame 492, as shown. In some implementations, one or more seams may be sutured adjacent an inflow edge that secures the fibrous material 401 about the support stent and/or in other location(s). The frame 492 and/or one or more other components of the valve implant device 410 can also have the leaflets 493 and/or other materials sutured thereto.

The anchoring skirt portion 412 is shows as being associated with the inflow end of the valve device 410. The frame 404 of the anchoring skirt 412 can be expandable, such as self-expanding, to advantageously provide for secure attachment to the valve annulus and/or other anatomy associated with the target heart valve. For example, in some embodiments, the valve frame 492 and/or sealing ring 491 are non-expandable, whereas the anchoring skirt frame 404 can expand from the contracted state shown in FIGS. 17-19 to an expanded state. The size of the anchoring skirt 412 can vary depending upon the overall size of the heart valve 410. The frame 404 of the valve 410 can comprise a generally tubular plastically-expandable structure having an undulating or scalloped lower end 409, as shown. The coarse fibrous material 402 can allow for the skirt 412 to be sutured to the adjacent heart tissue.

Figure 20:
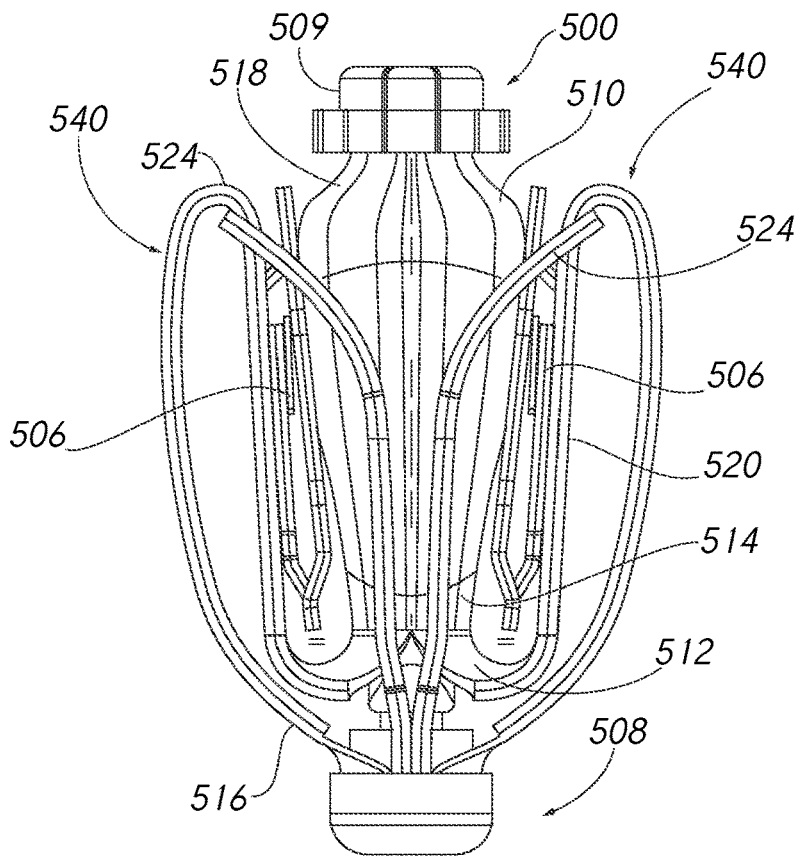
FIG. 20 is a side view of a prosthetic spacer device in accordance with one or more embodiments.

In addition to prosthetic heart valve and stent devices, other types of medical implant devices can include component(s) that are desirably at least partially covered in fibrous material using rotary jet spinning processes, as described herein. For example, FIG. 20 is a side view of a prosthetic spacer device 500 configured to reduce or prevent valvular regurgitation when attached to one or more leaflets of, for example, a native mitral valve in accordance with one or more embodiments. Alternatively, the spacer device 500 can be implanted at the aortic, tricuspid, or pulmonary valve regions of a human heart according to a suitable implantation process. The prosthetic spacer device 500 can be used to help restore and/or improve the functionality of a defective native valve. For example, in some embodiments, the prosthetic spacer device 500 can include a central or main body 510 and one or more movable elements 540 configured to capture the leaflets of the native valve between the elements 540 and the main body 510. The native leaflets can thereby form a seal against the main body 510. The main body 510, in turn, can be configured to prevent blood flow through the prosthetic device such that an acute reduction in regurgitation (e.g., functional mitral regurgitation) is achieved after implantation. This can be advantageous in patients where left ventricular function is not severely degraded. Examples of other prosthetic spacer devices are described further in U.S. Patent Publication Number 2018/0325661, which is incorporated herein by reference for all purposes.

In addition to the spacer member 510, the prosthetic spacer device 500 can comprise a plurality of anchors or paddles 540 (e.g., two in the illustrated embodiment), a plurality of clasps 506 (e.g., two in the illustrated embodiment), a first collar or hub member 508, and a second collar or hub member 509. First end portions 512 of the anchors 540 can be coupled to and extend from a first end portion 514 of the spacer member 510, and second end portions 516 of the anchors 540 can be coupled to the first collar 508. The second collar 509 can be coupled to a second end portion 518 of the spacer member 510.

Figure 21:
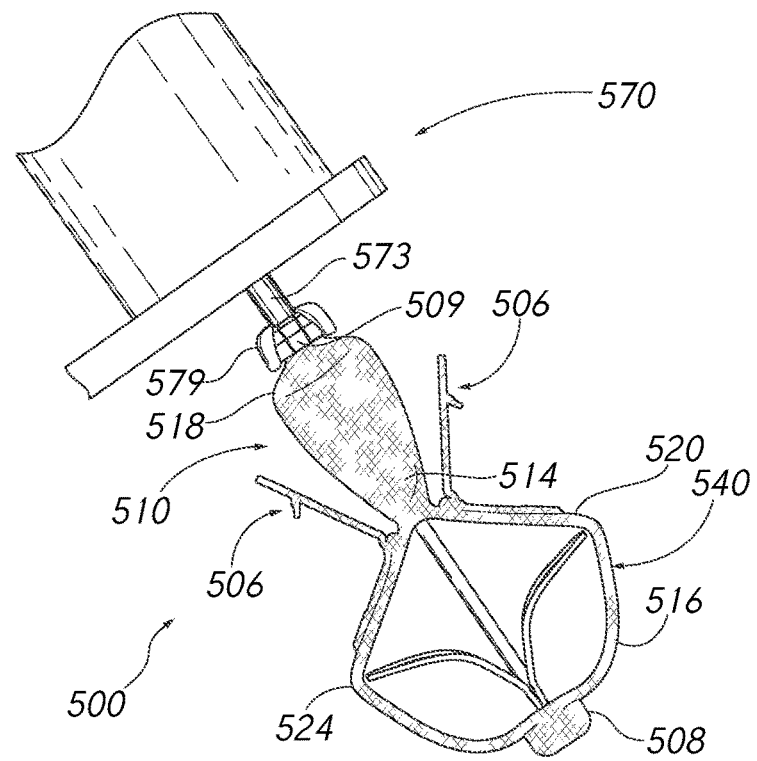
FIG. 21 shows a spacer device disposed on a holder in accordance with one or more embodiments.

FIG. 21 shows the spacer device 500 coupled to a holder 579, such as an arm- or clip-type holder as described herein. Although a clip/arm holder is shown in FIG. 21, it should be understood that any type of holder may be used to hold the spacer device 500, including cylindrical or other-shaped spacer-type holders or other attachment features, as described herein. The mandrel 573 and holder 579 may be part of a collector assembly 570, as described in detail herein.

The spacer device may be in an at least partially straightened-out configuration when fibrous material is applied thereto using rotary jet spinning. For example, in some implementations, an angle between the first portions 520 of the anchors 540 and the spacer member 510 can be approximately 180 degrees when the anchors 540 are in the straightened-out configuration, whereas the angle between the first portions 520 of the anchors 540 and the spacer member 510 can be approximately 0 degrees when the anchors 540 are in the fully folded configuration shown in FIG. 20. In some implementations, some and/or each component(s) (e.g., the space, the paddle) can be coated individually followed by assembly.

With the spacer device 500 disposed on the holder 579, the mandrel 573 and coupled holder 579 can be rotated about the axis defined by the mandrel 573. For example, the collector assembly 570 can comprise or be mechanically coupled to a rotor motor configured to rotate the mandrel 573. The various components of the collector assembly 570 may be controlled at least in part by control circuitry of a local and/or remote controller system.

Fibrous material may be applied to the spacer device 570 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the spacer member 510, clasps 520, anchors 540, and/or distal collar 508 to form one or more layers of fibrous material, as shown in FIG. 21.

Figure 22:
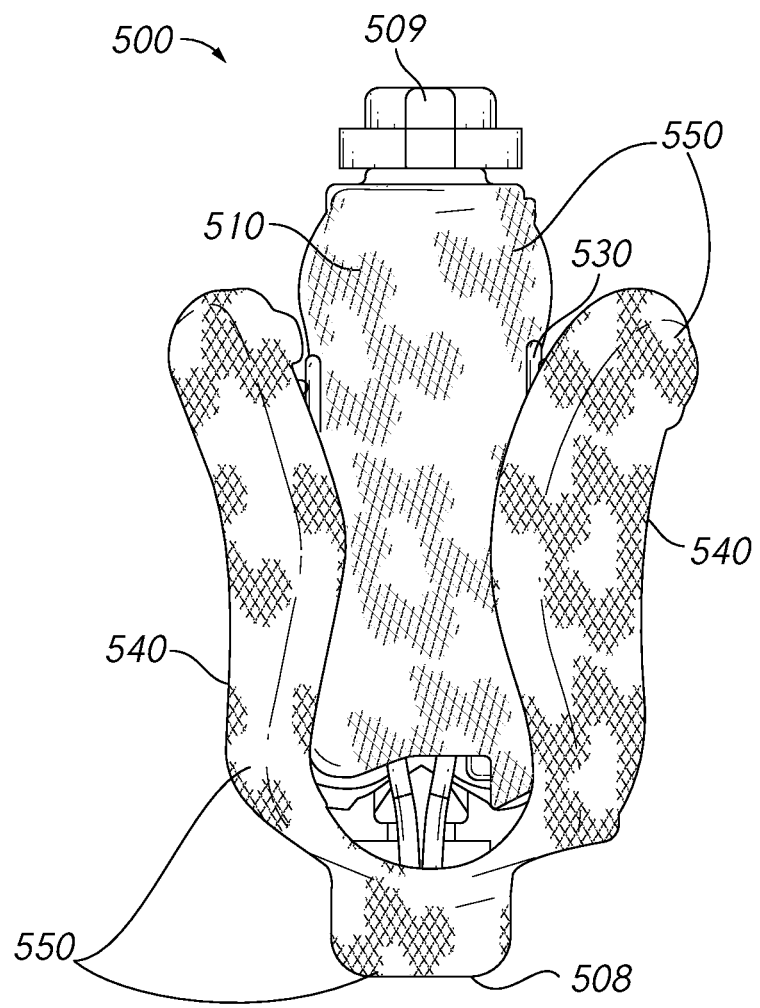
FIG. 22 shows a spacer device having fibrous material applied to portions thereof using rotary jet spinning in accordance with one or more embodiments.

FIG. 22 shows the spacer device 500 having fibrous material 550 applied to portions thereof using rotary jet spinning in accordance with one or more embodiments of the present disclosure. The spacer device 500 is shown in FIG. 22 with the fibrous material covering 550 disposed about the spacer member 510 and the anchors 540. In some examples, the fibrous material covering 550 can be porous such that the covering is at least partially permeable to blood flow. For example, the fibrous material covering 550 can be an openwork fabric or netting defining openings of any suitable or desirable dimensions. In certain examples, the fibrous material covering 550 can comprise a low-density rotary-jet-spun polymeric fibrous material having, for example, 60-120 courses per inch and/or 20-60 wales per inch. In order to produce the desired fibrous covering 550, the rate of rotation of the rotary jet spinning reservoir and/or mandrel/holder, the rate of translation of the mandrel/holder, the angle and/or change in angle of the holder assembly may be controlled to produce the desired application of fibrous material.

In some embodiments, the spacer device 500 can be configured to move between the configuration of FIG. 21 and the configuration of FIG. 22 by axially moving the first collar 508 and thus the anchors 540 relative to the spacer member 510 along a longitudinal axis extending between the first and second end portions 514, 518 of the spacer member 510. For example, the anchors 540 can be positioned in a straight configuration by moving the first collar 508 away from the spacer member 510 such that the anchors 540 become more taut/open.

From the straightened-out configuration of FIG. 21, the anchors 540 can be moved to the folded configuration of FIG. 22 by moving the first collar 508 toward the spacer member 510. Initially, as the first collar 508 moves toward the spacer member 510, the anchors 540 may bend at the joint portions 524, and the joint portions 524 move radially outwardly relative to the longitudinal axis of the spacer member 510 and axially toward the first end portion 514 of the spacer member 510, whereas as the collar 508 continues to move toward the spacer member 510, the joint portions 524 may move radially inwardly relative to the longitudinal axis of the spacer member 510 and axially toward the second end portion 518 of the spacer member 510 until the folded configuration of FIG. 22 is achieved.

Figure 23:
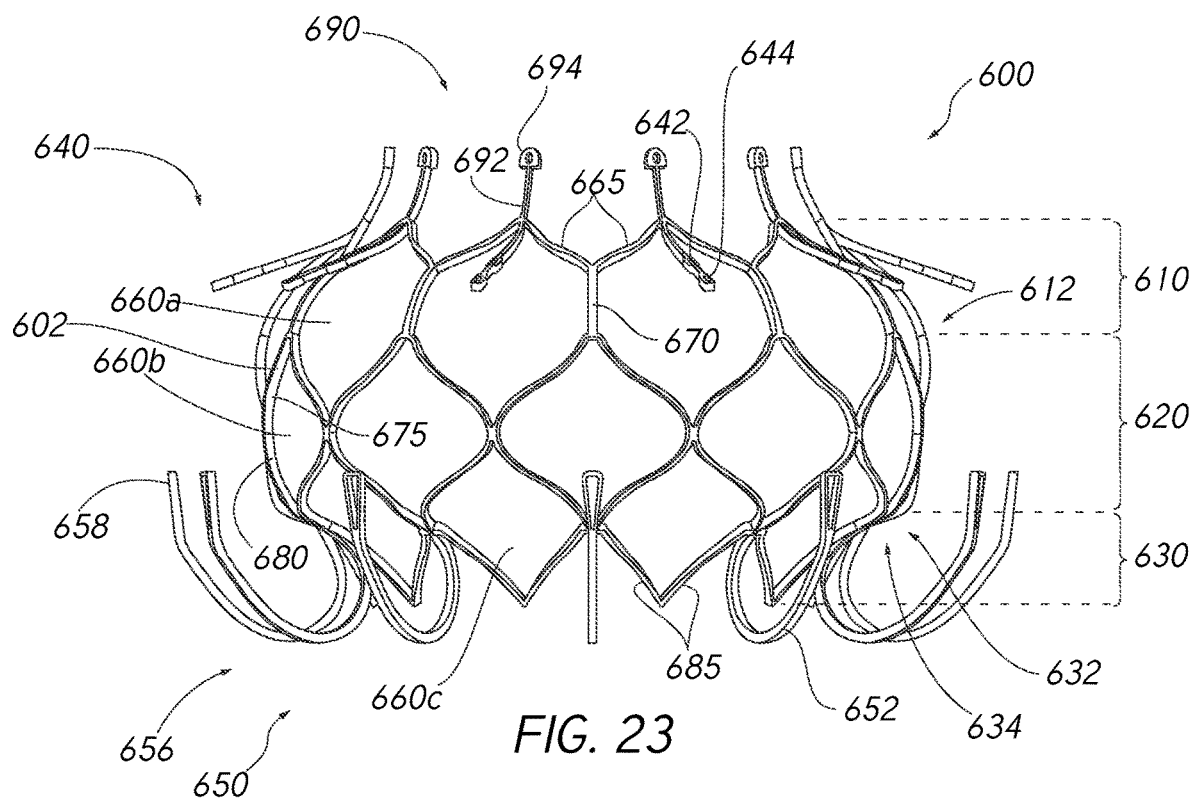
FIG. 23 shows a prosthetic heart valve device that can be covered at least in part by fibrous material using rotary jet spinning in accordance with one or more embodiments.
Figure 24:
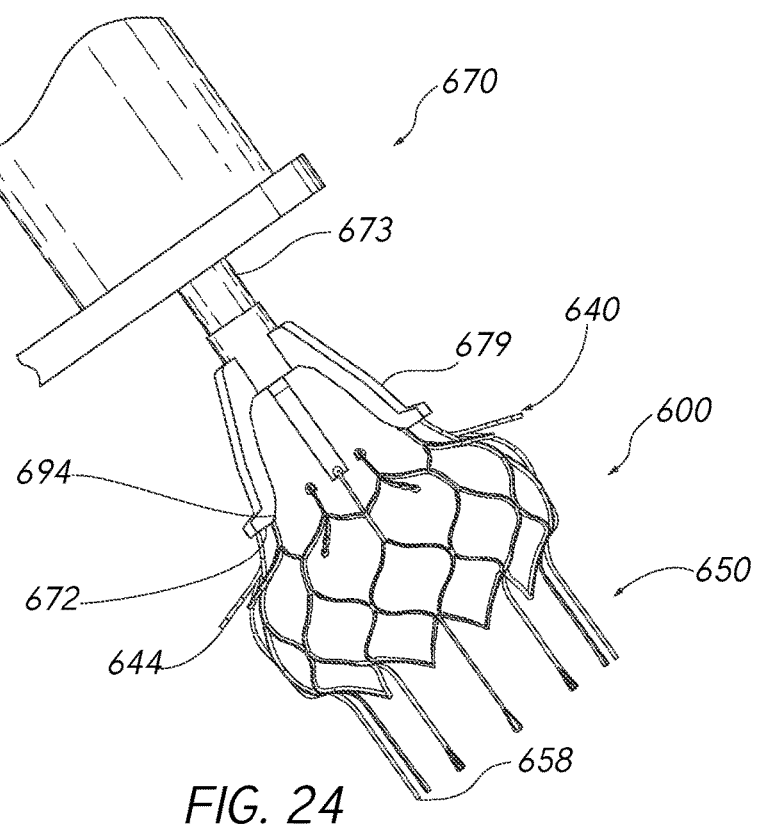
FIG. 24 shows a heart valve frame disposed on a holder in accordance with one or more embodiments.
Figure 25:
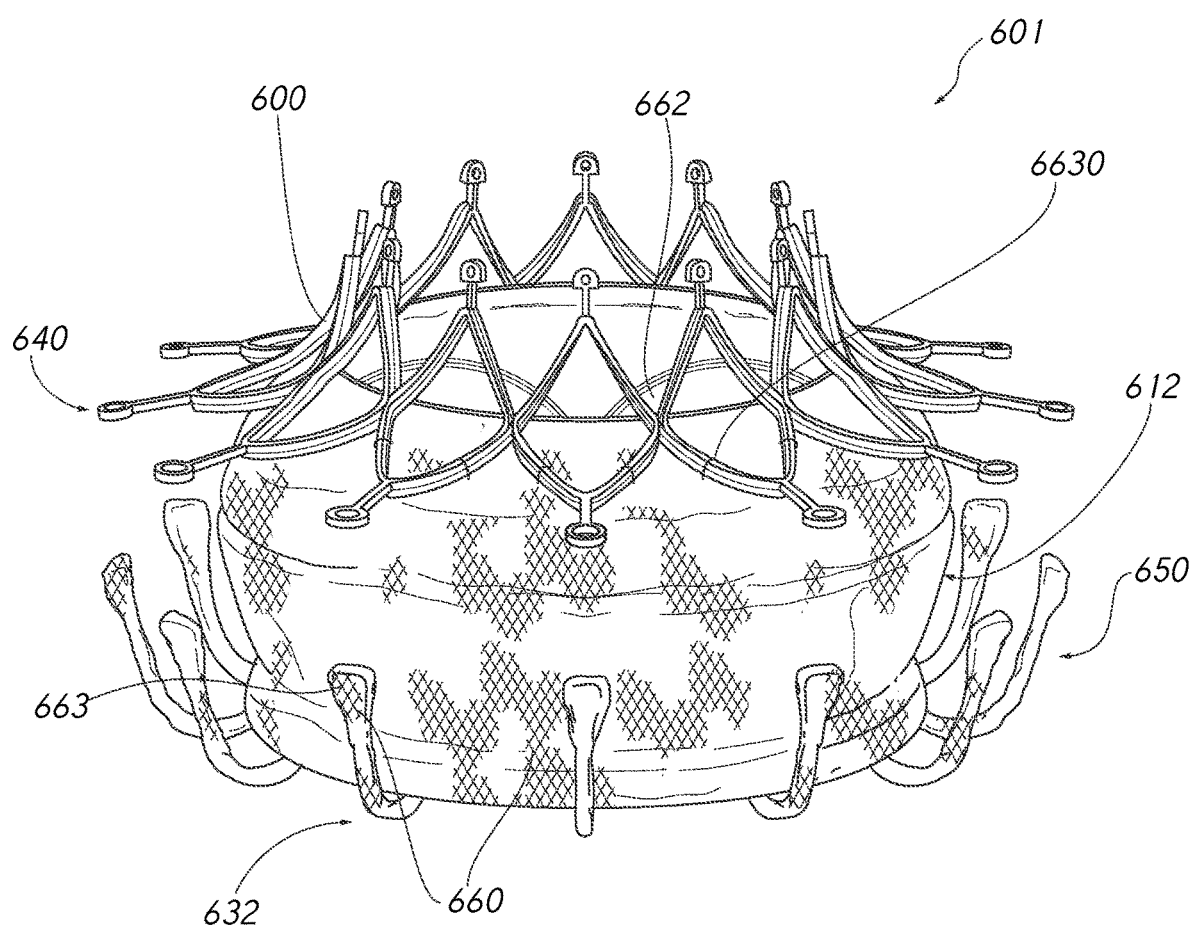
FIG. 25 shows a heart valve device having fibrous material applied to portions thereof using rotary jet spinning in accordance with one or more embodiments.

FIGS. 23-25 and the accompanying description relate to embodiments of another example type of prosthetic heart valve device that can be covered at least in part by fibrous material using rotary jet spinning solutions as described herein. In some embodiments, the heart valve device frame 600 of FIGS. 23 and 24 is a component of a heart valve device 601 (see FIG. 25) suitable for implantation as a replacement mitral valve. The frame 600 includes a frame body 602 having an upper region 610, an intermediate region 620, and a lower region 630. The frame 600 can include a first type of anchoring feature 640 and a second type of anchoring feature 650, either of which may serve as a proximal or distal anchoring feature.

One or both anchoring features 640, 650 can contact or engage a native valve annulus, such as the native mitral valve annulus, tissue beyond the native valve annulus, native leaflets, and/or other tissue at or around the implantation location. For example, when the frame 600 is used for a replacement mitral valve prosthesis, during at least the systolic phase of the cardiac cycle, the second anchoring feature 650 can be sized to contact or engage the native mitral valve annulus whereas the first anchoring feature 640 is sized to be spaced from the native mitral valve annulus.

As shown, the frame body 602 can have a bulbous or slightly-bulbous shape, with the intermediate region 620 being larger than the upper region 610 and/or the lower region 630. The bulbous shape of the frame body 602 can advantageously allow the frame body 602 to engage a native valve annulus or other body cavity, while spacing the inlet and outlet from the heart or vessel wall. This can advantageously reduce undesired contact between the prosthesis and the heart or vessel, such as the atrial and ventricular walls of the heart.

The intermediate region 620 can be generally cylindrical in shape such that a diameter of an upper end of the intermediate region 620 and/or a diameter of a lower end of the intermediate region 620 is equal or generally equal to the diameter of a middle portion of the intermediate region 620. The general uniformity of the diameter of the intermediate region 620 from the upper end to the lower end, in conjunction with the axial dimension between the upper end and the lower end (e.g., the "height" of the intermediate region 620), provides for a significantly large circumferential area upon which a native valve annulus, or other body cavity, can be engaged. This can beneficially improve securement of the frame 600 to the native valve annulus or other body cavity. This can also improve sealing between the frame 600 and the native valve annulus, or other body cavity, thereby reducing paravalvular leakage.

In some embodiments, the frame body 602, when in an expanded configuration, can have a diameter at its widest portion of between about 30 mm to about 60 mm, between about 65 mm to about 55 mm, about 40 mm, any sub-range within these ranges, or any other diameter as desired. In some embodiments, the frame body 602 in an expanded configuration has a diameter at its narrowest portion between about 20 mm to about 40 mm, any sub-range within these ranges, or any other diameter as desired. In the expanded configuration, the frame body 602 can have an axial dimension between the upper and lower ends of the frame body 602 (e.g., the "height" of the frame body 602) of between about 10 mm to about 40 mm, between about 18 mm to about 60 mm, about 20 mm, any sub-range within these ranges, or any other height as desired.

At the juncture between the intermediate region 620 and the upper region 610, the frame body 602 can include a bend 612. The bend 612 can be a radially inward bend towards the longitudinal axis of the frame 600 such that a portion of the upper region 610, extending upwardly from the beginning of bend 612 adjacent the intermediate region 62o, is inclined or curved towards the longitudinal axis of the frame 600. The inclined or curved portion of the upper region 610 can facilitate the securement of a supplemental prosthesis within the frame 600.

At the juncture between the intermediate region 620 and the lower region 630, the frame body 602 can include a bend 632 toward the longitudinal axis of the frame 600. The bend 632 can be a radially-inward bend towards the longitudinal axis of the frame 600 such that a portion of the lower region 630, extending downwardly from the beginning of bend 632 adjacent the intermediate region 620, is inclined or curved towards the longitudinal axis of the frame 600. The bend 632 can generally form an arc with an angle between about 20 degrees to about 90 degrees. The lower region 630 can include a bend 634 below the bend 632. The bend 634 can be oriented opposite that of the bend 632 such that a portion of the lower region 630, extending downwardly from the beginning of the bend 634, is inclined or curved at less of an angle towards the longitudinal axis of the frame 600 than the portion above the beginning of the bend 634, is generally parallel to the longitudinal axis, or is inclined or curved at an angle away from the longitudinal axis of the frame 600. The diameter of the upper end of the upper region 610 and the lower end of the lower region 630 may be about the same or may differ.

The frame body 602 can include a plurality of struts with at least some of the struts forming cells 660a, 660b, 660c. Any number of configurations of struts can be used, such as rings of undulating struts shown forming ellipses, ovals, rounded polygons, teardrops, chevrons, diamonds, curves, and/or various other shapes. In some embodiments, the frame body 602 can include three rows of cells 660a, 660b, 660c.

The cells 660a, 660b, 660c can have any suitable or desirable shape, and can advantageously be self-expanding or otherwise expandable. For example, the cells of any of the rows may have a hexagonal or generally-hexagonal shape, diamond shape, or the like. The circumferentially-expansible struts 665 can be inclined or curved towards a longitudinal axis of the frame 600 such that an upper portion of the struts 665 are positioned closer to the longitudinal axis of the frame 600 than the lower portion of the struts 665. The struts 670 can extend generally longitudinally and can incorporate the bend 612 such that an upper portion of the struts 670 are inclined or curved towards the longitudinal axis of the frame 600.

The lower portion of cells 660a can be formed from a set of circumferentially-expansible struts 675 having a zig-zag or undulating shape forming a repeating "V" shape. The struts 675 can form a generally-cylindrical portion of the frame 600 with the upper portion of the struts 675 having a radial dimension which is about the same as the radial dimension as the lower portion of the struts 675.

The cells 660b, 660c may provide a foreshortening portion of the frame 600. The illustrated diamond or generally-diamond shape can be formed via a combination of struts. The upper portion of cells 660b can be formed from the set of circumferentially-expansible struts 675 such that cells 660b share struts with cells 660a. The lower portion of cells 660b can be formed from a set of circumferentially-expansible struts 680. The circumferentially-expansible struts 680 can incorporate the bend 632 such that an upper portion of the struts 680 form a generally-cylindrical portion of the frame 600 and the lower portion of the struts 680 can be inclined or curved towards the longitudinal axis of the frame 600. The upper portion of cells 660c can be formed from the set of circumferentially-expansible struts 680 such that cells 660c share struts with cells 660b. The lower portion of cells 660c can be formed from a set of circumferentially-expansible struts 685. The circumferentially-expansible struts 685 can be inclined or curved towards the longitudinal axis of the frame 600.

The anchoring feature 640 can include one or more anchors. For example, as shown in the illustrated embodiment, the anchoring feature 640 can include twelve anchors. Each anchor can include one or more struts 642 extending from an upper region 610 of the frame body 602. As shown, struts 642 extend into the cells 660a. In some embodiments, the struts 642 extend from an upper intersection of two segments of the cell 660a, for example, from the uppermost corner of the cells 660a between struts 665. The struts 642 can extend generally downwardly into the cells 660a while curving outwards away from the frame body 602. The anchoring feature 640 extends radially outwardly from the frame body 602 as it extends generally downwardly towards a tip 644.

The anchoring feature 640 can include one or more eyelets that form a portion of the tip 644 of the anchoring feature 640 that can be used to attach other components of the prosthesis in which the frame 600 is used. The anchoring feature 650 can include one or more anchors. Each anchor can include one or more struts 652 extending from a lower region 630 of the frame 600.

The struts 652 may extend generally downwardly while curving inwardly towards the longitudinal axis from the frame 600. The struts 652 can incorporate a bend 654 to orient the strut 652 such that it extends radially outward away from the longitudinal axis of the frame 600. The bend 654 can be generally semi-circular or semi-elliptical which can provide a space for the distal ends of the native valve leaflets to be held/stored. The anchors may then extend in a linear segment radially outwardly and upwardly. The struts 652 can include a second bend 656 along the linear segment that can orient the strut 652 such that it extends generally parallel to the longitudinal axis of the frame 600. In some embodiments, each of the anchoring features 640, 650 are positioned or extend generally radially outwardly from the frame 600 so that the anchor tips 644, 658 are generally spaced away or radially outward from the rest of the frame body 602 and from where the base of the anchors connect to the frame body 602.

Individual anchors may extend radially outwardly from the frame at an anchor base and terminate at an anchor tip. The individual anchors can be connected to the frame at one of many different locations including apices, junctions, other parts of struts, etc. Further details that may be incorporated and/or interchanged with the features described herein are disclosed in U.S. Publication Nos. 2014/0277422, 2014/0277427, 2014/0277390, and 2015/0328000, which are incorporated by reference herein for all purposes. Although a particular embodiment of a mitral valve frame is shown in FIGS. 23-25, it should be understood that the fiber-application processes and devices disclosed herein apply to other types of frames as well, including frames comprising rigid rings, spirally-wound tubes, and other tubes that fit within, for example, a heart valve annulus and that define an orifice therethrough for the passage of blood.

FIG. 24 shows the heart valve frame 600 disposed on a holder 679, such as an arm-type holder as described herein. Although an arm holder is shown in FIG. 24, it should be understood that any type of holder may be used to hold the valve frame 600, including cylindrical or other-shaped spacer-type holders or other attachment features, as described herein. The mandrel 673 and holder 679 may be part of a collector assembly 670, as described in detail herein.

With the valve frame 600 disposed on the holder 679, the mandrel 673 and coupled holder 679 can be rotated about the axis defined by the mandrel 673. For example, the collector assembly 670 can comprise a rotor motor configured to rotate the mandrel 673. The various components of the collector assembly 670 may be controlled at least in part by control circuitry of a local and/or remote controller system.

Fibrous material may be applied to the valve frame 600 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the outer surface of the frame 600 to form one or more layers of fibrous material, as shown in FIG. 25.

Fibrous material may be applied to at least a portion of the frame 600 in order to provide covering and/or cushioning for the valve implant device. In some implementations, rotary jet spinning may be used to apply fibrous material in a manner so as to surround or partially surround or cover at least a portion of the first anchoring feature 640 and/or the second anchoring feature 650, such as the tips or ends 644 of the first anchoring feature 640 and/or the tips or ends 658 of the second anchoring feature 650 and/or the struts to which the tips or ends 644, 658 are attached.

In some implementations, one or more features of the frame 600 may be straightened-out at one or more points in the fibrous-material-application process. For example, as shown in FIG. 24, one or more anchor features, such as the anchor features 650, can be straightened-out for application of fibrous material using rotary jet spinning on a backside of the anchor features.

In some embodiments, additional cushioning may be applied to one or more features of the frame 600, such that the applied fibrous material forms a layer covering the cushioning. For example, the cushioning can be formed of a foam material, such as a polymer foam, such that the cushioning is at least somewhat compliant. In some embodiments, the cushioning can be formed as a polymer molded insert. In some embodiments, the cushioning can be loosely coupled to the anchoring feature(s). In some embodiments, all of the anchors of the second anchoring feature 650 have cushioning applied thereto.

The upper end of the strut 692 can include an enlarged head 694 feature, which may have a semi-circular or semi-elliptical shape, or any other form or shape. The end 694 and/or the strut 692 can serve as a locking tab and can include one or more eyelets at one or more locations. The locking tab features can be advantageously used with various types of delivery systems. For example, the shape of the struts 692 and the enlarged head 694 can be used to secure the frame 600 to a "slot-" based delivery system. In some implementations, the head portion (e.g., eyelet) 694 can be used to secure the frame 600 to a tether-type delivery system, which may utilize sutures, wires, or fingers to control delivery of the frame 600. Such features can advantageously facilitate recapture and repositioning of the frame 600 in situ. In addition, or as alternative, to serving as locking tab features, the strut ends 694 may be used to secure the frame 600 to the holder 679. For example, the strut heads 694 can be used to suture, clip, snap, hook, or otherwise secure the strut head(s) 694 to the arm(s) 679 or other feature(s) of the holder 679.

FIG. 25 shows a heart valve device 601 having fibrous material applied to portions thereof using rotary jet spinning in accordance with one or more embodiments of the present disclosure. The valve body preferably includes a plurality of valve leaflets 662. The plurality of valve leaflets 662 can function in a manner similar to the native mitral valve, or to any other valves in the vascular system, as desired.

Fibrous material 66o may be applied to one or more portions or components using rotary jet spinning, as described herein. For example, the fibrous material 660 can be applied to the exterior (and/or interior) of the frame 600. In some embodiments, the fibrous material 660 extends from an upper region of the frame 600 towards a lower region of the frame. In some implementations, rotary jet spinning is used to apply fibrous material to the frame 600 between the radial features 640 and the base of the frame. In some implementations, fibrous material is applied to one or more sides of anchors of the anchoring feature 650. Application of the fibrous material 660 can beneficially enhance sealing along the lower region of the frame 600. The fibrous material 660 can be applied such that a portion of the fibrous material positioned around a middle portion of the frame 600 is loose relative to an exterior of the frame. Variation in rotational and/or translational speed of the fibrous solution reservoir and/or collection assembly can be implemented to produce the desired thickness, looseness, and/or other characteristic(s) of the fibrous material applied to the frame 600. In some implementations, sutures 6630 can wrap around struts of certain anchoring features and/or struts of the frame body to couple the anchor/frame features to the fibrous material 660.

Rotary jet spinning can be used to apply fibrous material having different sets of characteristics to different portions of the frame. For example, fibrous material having a first set of characteristics may be applied to the frame body 612, whereas fibrous material having a second set of characteristics can be applied to the anchor features 650. Processes of depositing the fibrous material can be performed as many times as desired and/or for the desired amount of time in order to produce the desired thickness and/or other characteristics of fibrous material. In order to produce the desired fibrous covering 660, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 26:
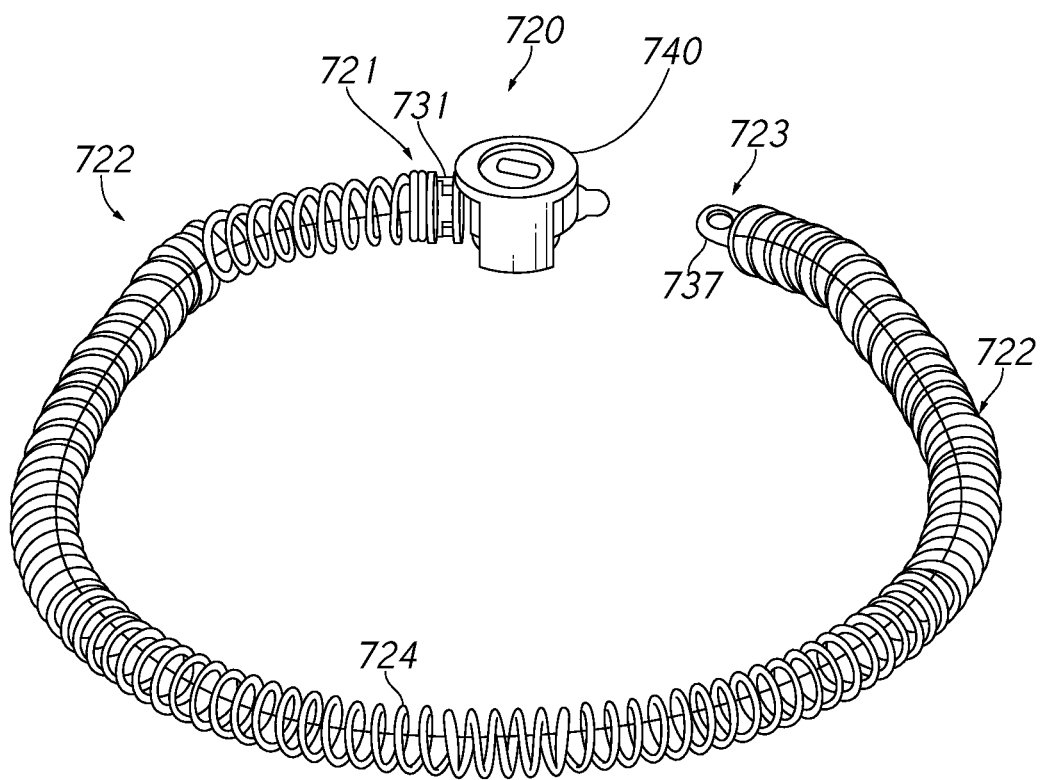
FIG. 26 is a perspective view of an annuloplasty repair device in accordance with one or more embodiments.
Figure 27:
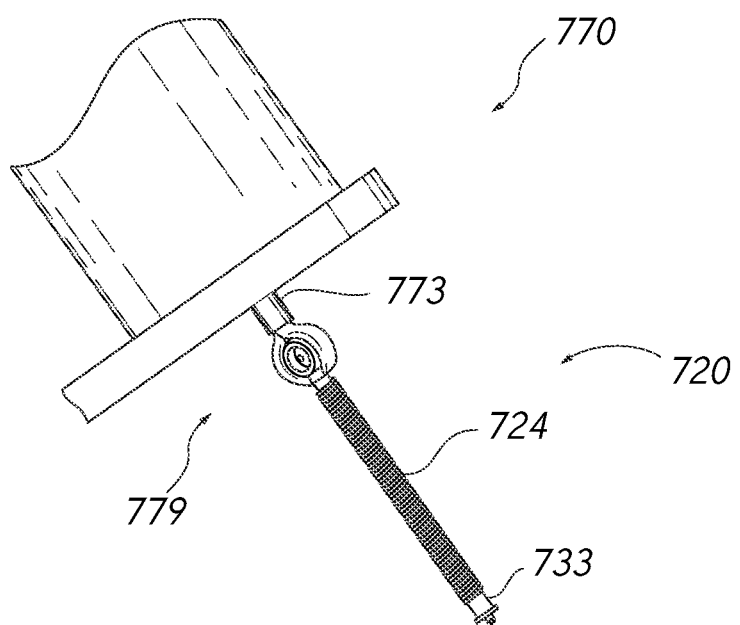
FIG. 27 shows an annuloplasty repair device disposed on a holder in accordance with one or more embodiments.
Figure 28:
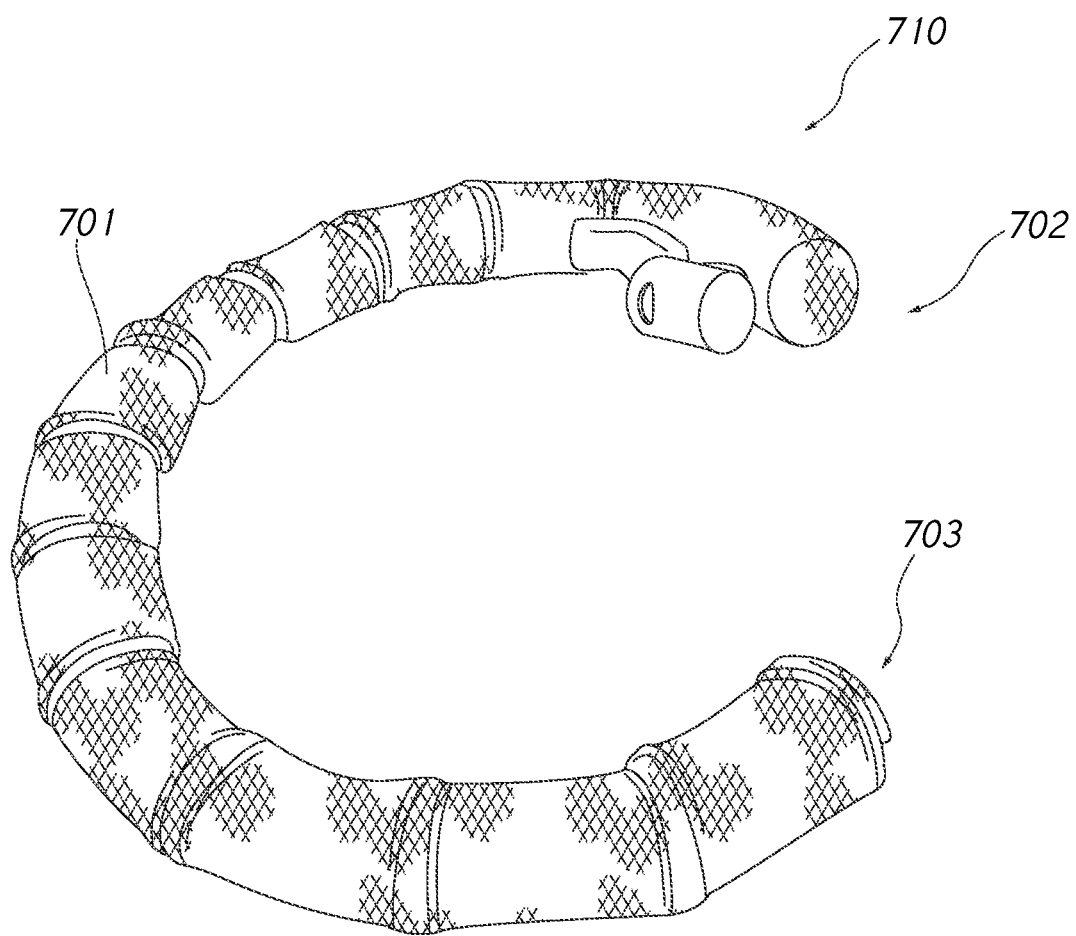
FIG. 28 shows a perspective view of an annuloplasty repair device having fibrous material applied thereto using rotary jet spinning in accordance with one or more embodiments.

FIGS. 26-28 and the accompanying description relate to embodiments of another example type of medical implant device that can be covered at least in part by fibrous material using rotary jet spinning solutions as described herein. Specifically, FIGS. 26-28 illustrate an annuloplasty repair device 700 that includes one or more components or portions that can desirably be at least partially covered in fibrous material using rotary jet spinning processes, as described herein.

FIG. 26 is a perspective view of an annuloplasty repair device 720 in accordance with one or more embodiments. The annuloplasty repair device 720 can be used to help restore and/or improve the functionality of a defective native valve. For example, the annuloplasty repair device 720 may be designed to for use with procedures to tighten or reinforce a native heart valve annulus, such as a mitral valve annulus. Generally, a heart valve annulus can widen and change from its normal shape as a result of enlargement of the heart and/or valve regurgitation conditions. Widening or malformation of the annulus can lead to failure of the valve leaflets to properly coapt. To repair a malformed or defective annulus, the annuloplasty repair device 720 can be secured to the valve annulus to reshape, reinforce, or tighten the annulus.

The example annuloplasty repair device 720 can include an annuloplasty structure 722, comprising a body portion 724, a flexible contracting longitudinal member 730 (herein referred to as "contracting member" or "flexible member"), and/or an adjusting mechanism 740. At least a portion of the body portion 724 can comprise a compressible material, such as a coiled element, as shown by way of illustration and not limitation. For example, the body portion 724 may comprise stent-like struts, or a braided mesh. The body portion 724 can define a lumen along the longitudinal axis of the annuloplasty structure 722, which advantageously houses the adjustable contracting member 730. The flexible contracting member 730 can comprise a wire, a ribbon, a rope, or a band. The flexible contracting member 730 can be coupled at a first end portion thereof to the adjusting mechanism 740 which is coupled to a first end 721 of the structure 722. A second end portion of the flexible contracting member 730 can be coupled to a second end 723 of the annuloplasty structure 722. In some embodiments, the flexible contracting member 730 has at least one free end portion. The flexible contracting member 730 together with the compressible element of the body portion 724 and the braided mesh surrounding the body portion 24 can impart flexibility to the annuloplasty structure.

The body portion 724 can comprise a relatively flexible biocompatible material, such as nitinol, stainless steel, platinum iridium, titanium, expanded polytetrafluoroethylene (ePTFE), cobalt chrome, and/or braided polyester suture (e.g., TI-CRON suture, Medtronic). In some embodiments, the body portion 724 is coated with PTFE (Polytetrafluoroethylene), or other material. In some embodiments, the body portion 724 comprises accordion-like compressible structures which facilitate proper cinching of the annulus when the annuloplasty structure 722 is contracted. The body portion 724, when compressed while implanted around a valve annulus, can enable portions of the annuloplasty structure 722 to contract and/or conform to the configuration of the annulus. Thus, the compressible features of the body portion 724 can facilitate contraction of the annulus in response to contraction of the annuloplasty structure 722.

In FIG. 26, the annuloplasty structure 722 is shown in a partially-contracted state, such that the axis of the structure 722 is at least partially non-linear. For example, in response to rotation or other actuation of the adjustment component 740, a portion of the contracting member 730 can be wrapped around a spool (not shown), or otherwise adjusted to effectively shorten the portion of the flexible member disposed within the annuloplasty structure 722. Accordingly, the second end of the flexible contracting member 730 can be pulled toward the adjustment mechanism 740, thereby pulling the second end 723 of the structure 722 toward first end 721 of the structure 722.

FIG. 27 shows the annuloplasty repair device 720 disposed on a holder 779, such as an arm- or clip-type holder as described herein. Although a clip/arm holder is shown in FIG. 27, it should be understood that any type of holder may be used to hold the annuloplasty repair device 72o, including cylindrical or other-shaped spacer-type holders or other attachment features, as described herein. The mandrel 773 and holder 779 may be part of a collector assembly 770, as described in detail herein.

The annuloplasty repair device 720 may be in an at least partially straightened-out configuration, as shown in FIG. 27 when fibrous material is applied thereto using rotary jet spinning. With the annuloplasty repair device 720 disposed on the holder 779, the mandrel 773 and coupled holder 779 can be rotated about the axis defined by the mandrel 773. For example, the collector assembly 770 can comprise or be mechanically coupled to a rotor motor configured to rotate the mandrel 773. The various components of the collector assembly 770 may be controlled at least in part by control circuitry of a local and/or remote controller system.

Fibrous material may be applied to the annuloplasty repair device 720 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the annuloplasty structure 722 (e.g., coils 724) to form one or more layers of fibrous material.

FIG. 28 shows a perspective view of an annuloplasty repair device 710 having fibrous material 701 applied thereto using rotary jet spinning in accordance with one or more embodiments of the present disclosure. In some examples, the fibrous material 701 can be porous such that the fibrous material is at least partially permeable to blood flow. For example, the fibrous material 701 can comprise openings of any suitable or desirable dimensions. In order to produce the desired fibrous covering 701, the rate of rotation of the rotary jet spinning reservoir and/or mandrel/holder, the rate of translation of the mandrel/holder, the angle and/or change in angle of the holder assembly may be controlled to produce the desired application of fibrous material.

In FIG. 28, the annuloplasty repair device is shown in an at least partially contracted/rounded state. In some embodiments, the annuloplasty repair device 710 can be configured to move between the straightened configuration of FIG. 27 and the contracted configuration of FIG. 28 by shortening an internal cable or other suture or device connected between one end 702 of the device 710 and the opposite end 702 of the device 710.

Figure 29:
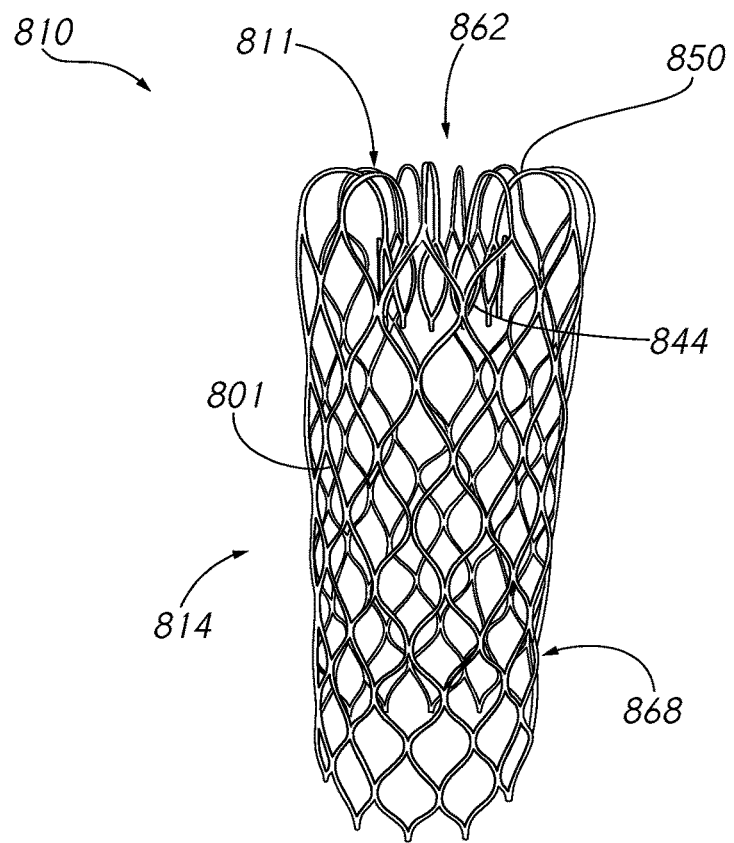
FIG. 29 is a perspective view of a frames for a docking device in accordance with one or more embodiments of the present disclosure.
Figure 30:
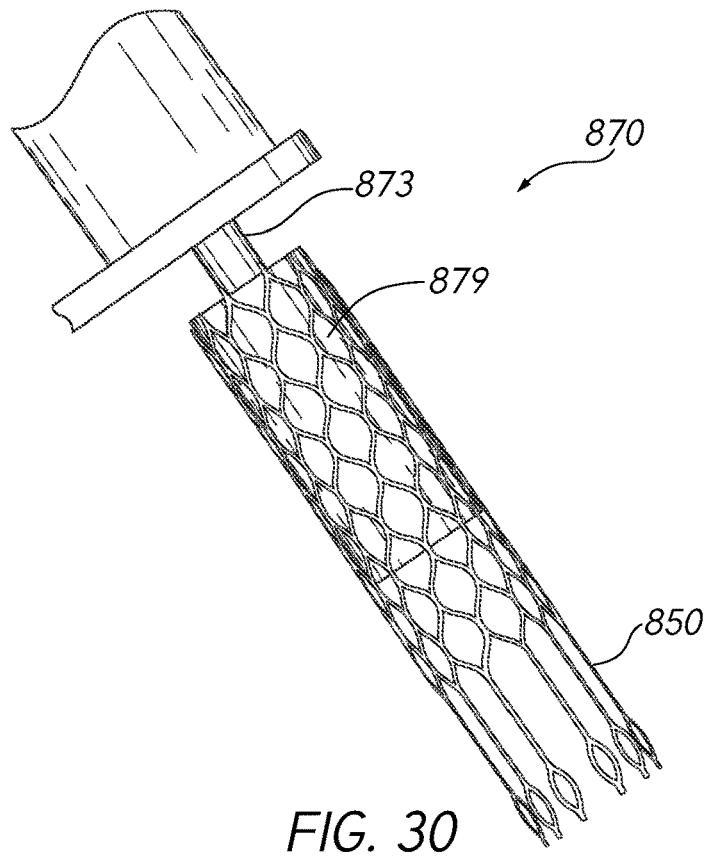
FIG. 30 shows the docking device frame disposed on a holder in accordance with one or more embodiments.
Figure 31:
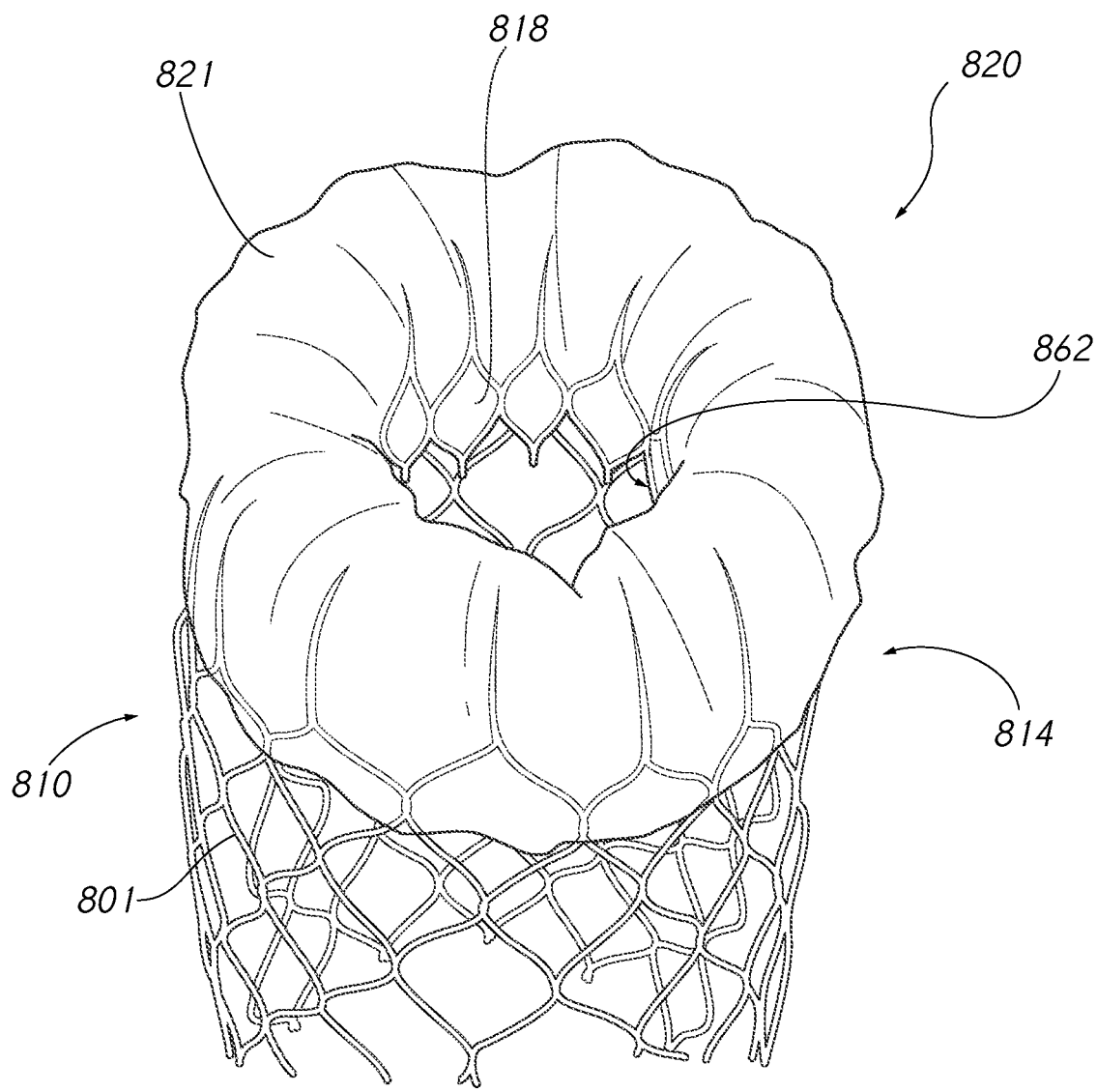
FIG. 31 shows a perspective view of a docking device having fibrous material applied to at least a portion thereof in accordance with embodiments of the present disclosure.

FIGS. 29-31 and the accompanying description relate to embodiments of another example type of medical implant device that can be covered at least in part by fibrous material using rotary jet spinning solutions as described herein. Specifically, FIGS. 29-31 illustrate a docking device 820 that includes one or more components or portions that can desirably be at least partially covered in fibrous material using rotary jet spinning processes, as described herein.

Docking devices covered in fibrous material using rotary jet spinning in accordance with embodiments of the present disclosure can be configured for implantation in the body or a circulatory vessel/chamber of the body (e.g., a heart, native heart valve, blood vessel, vasculature, artery, vein, aorta, inferior vena cava (IVC), superior vena cava (SVC), pulmonary artery, aortic valve, pulmonary valve, mitral valve, tricuspid valve, etc.). Such devices can include at least one sealing portion, frame, and/or valve seat. The docking device 820 (see FIG. 31) and its frame 810 can be configured or shaped to conform to a shape of a portion of the body in which it is to be implanted, such as to a shape of an aorta, pulmonary artery, IVC, or SVC. Further, whether the anatomy is varied or more uniform, docking devices and/or associated frames applicable to embodiments disclosed herein can be configured such that, when expanded inside the target vessel, the majority of the docking station contacts an interior surface of the vessel and distributes the pressure and force exerted by the docking device over the portion or length of the docking station in contact with the interior surface. This can be helpful, for example, in treating aortic insufficiency caused by an enlarging of the aortic valve and/or aorta.

FIG. 29 is a perspective view of a frame 810 for a docking device in accordance with one or more embodiments of the present disclosure. The frame includes legs 850 for supporting a valve seat 818 or forming a portion of a valve seat. The valve seat 818 can comprise a separate component that is attached to the legs 850 or can be integrally formed with the legs 850. In some implementations, the valve seat 818 is replaced/integrated with a valve device and the docking device 820 and valve device are configured and deployed as a single unit.

The frame 810, which is advantageously at least partially expandable, can provide the shape of a sealing portion 811, the valve seat 818, and/or the retaining portion 814. The frame 810 can take a wide variety of different forms. In some implementations, the frame 810 has an end 862 having an inside diameter defined by the valve seat 818 and an outside diameter defined by an annular or cylindrical outer wall 868 of the retaining portion 814.

The valve seat 818 can be formed by an annular wall 18 that extends downward from the inside diameter of the sealing portion 811. The frame 810 may be formed from an expandable lattice, as shown. The expandable lattice can be made in a variety of ways, such as with individual wires connected to form the lattice. In some implementations, the lattice is formed by braiding a suitable material. Alternatively, the lattice may be cut from a sheet and then rolled or otherwise formed into the shape of the expandable frame, molded, cut from a cylindrical tube, or formed in other way(s) or combination of the processes listed.

In some embodiments, the frame 810 is made from a relatively flexible metal, metal alloy, or polymer. Examples of metals and metal alloys that can be used include, but are not limited to, nitinol and other shape memory alloys, cobalt-chromium (e.g., ELGILOY alloy), and stainless steel, but other metals and resilient or compliant non-metal materials can be used to make the frame 810. These materials can allow the frame to be compressed to a small size, and then when the compression force is released, the frame can self-expand back to its pre-compressed diameter and/or the frame can be expanded by inflation of a device/balloon positioned inside the frame. The frame 850 can also be made of other materials and/or be expandable and collapsible in different ways, including but not limited to mechanically-expandable, balloon-expandable, self-expandable, or a combination of these.

The sealing portion 811 can have fibrous material applied thereto, such as using rotary jet spinning in accordance with processes disclosed herein. The sealing portion 811 can take any form that prevents or inhibits the flow of blood from flowing around the outside surface of a valve mounted to the docking device. In some embodiments, the fibrous material applied to the sealing portion 811 can extend to and/or over the valve seat 818. The fibrous material 821 can extend radially outward, covering the end 862 of the frame 810 and/or can extend longitudinally to cover at least a portion of the annular outer portion or wall 814. The sealing portion 811 can provide a seal between the docking device 820 and an interior surface of the target vessel. That is, the sealing portion 811 and the associated valve (when in a closed state) can substantially prevent or inhibit blood from flowing in the inflow direction.

The valve seat 818 can be formed from a portion of the frame 810 or can be formed separately from the frame 810. The valve seat 818 can take any form that provides a supporting surface for implanting or deploying a valve implant device in the docking device 800 when the docking device is expanded. The valve seat can optionally be reinforced with a reinforcing material (e.g., fibrous material from a rotary jet spinning system, a suture, wire, band, collar, etc. that can circumscribe the valve seat or a portion of the valve seat).

The retaining portion(s) 814 can take a variety of different forms. For example, the retaining portion(s) 814 can include any structure that sets the position of the docking device 800 in the target vessel or chamber. For example, the retaining portion(s) 814 can press against or into the inside tissue surface and/or contour/extend around anatomical structures of the target vessel(s) to set and maintain the position of the docking device Boo. The retaining portion(s) 814 can be part of or define a portion of the body and/or sealing portion of the docking station 820 or can be a separate component that is attached to the body of the docking device.

The retaining portion 814 can have an elongated form to allow a relatively small force to be applied to a large area of the target tissue, while a valve mounted to the docking device 800 can apply a relatively large force to the valve seat 818. Applying a small radially-outward force over a larger area can be sufficient to securely hold the docking station in place, which can allow the docking station to conform to the unique shape/size of the anatomy and avoid/reduce the likelihood of damaging relatively weaker native tissue. The frame 810 (e.g., the retaining portion 814) may be formed of struts 801, which can have varying thickness. For example, reduced thickness in some area can advantageously allow for bending or flexing more easily. In some embodiments, the frame 810 is configured such that, when implanted, all or most of the outer surface of the docking station or frame contacts the interior surface of the target blood vessel (even when irregular or varied in shape). This also helps avoid/reduce the likelihood of damaging relatively weaker native tissue (e.g., by having too much localized force and/or pressure in one, two, or more particular locations).

FIG. 30 shows the docking device frame 810 disposed on a holder 879, such as a cylinder-type spacer form as described herein. Although a cylinder-type holder is shown in FIG. 30, it should be understood that any type of holder may be used to hold the valve frame 810, including arm-type holders or other attachment features, as described herein. The mandrel 873 and holder 879 may be part of a collector assembly 870, as described in detail herein.

With the valve frame 810 disposed on the holder 879, the mandrel 873 and coupled holder 879 can be rotated about the axis defined by the mandrel 873. For example, the collector assembly 870 can comprise a rotor motor configured to rotate the mandrel 873. The various components of the collector assembly 870 may be controlled at least in part by control circuitry of a local and/or remote controller system.

Fibrous material may be applied to the frame 810 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the outer surface of the frame 810 to form one or more layers of fibrous material, as shown in FIG. 31.

Fibrous material may be applied to at least a portion of the frame 810 in order to provide a sealing covering for the docking device 820. In some implementations, rotary jet spinning may be used to apply fibrous material in a manner so as to cover at least a portion of the end struts 862, such as the tips or ends 844, which may serve as the valve seat when the struts 862 are bent inward, as shown in FIG. 31.

In some implementations, one or more features of the frame 810 may be straightened-out at one or more points in the fibrous-material-application process. For example, as shown in FIG. 30, the end struts 862 can be straightened-out for application of fibrous material using rotary jet spinning.

FIG. 31 shows a perspective view of a docking device 820 having fibrous material 821 applied to at least a portion thereof in accordance with embodiments of the present disclosure. The frame 810 can have rotary-jet-spun fibrous material 821 applied on an end 862 of the frame 810 to effectuate a seal between a valve and interior surface of the target blood vessel when the valve is disposed in the valve seat 818 of the frame 810 and the frame 810 is radially expanded and placed in the target blood vessel. As applied, the fibrous material 821 can form a cylinder that appears rolled over the end 862 of the frame 810.

In some implementations, after the fibrous material 821 has been applied, the fibrous material 821 can be secured to the frame 810 in some manner. For example, the fibrous material 821 can be attached to the frame 810 with sutures, adhered, tied, fused, or the like. The fibrous material 821 can be deposited onto the end 862 of the frame 810. In some embodiments, the end of the fibrous material 821 abuts the end 862 of the frame 810. The inside diameter of the fibrous material 821 can advantageously be radially inward of and adjacent to the inside diameter of the frame 810. The outside diameter the fibrous material 821 can be radially outward of and adjacent to the outside diameter of the frame 810. The proximal surface of the fibrous material 821 can extend around a portion of the retaining portions 814 of the frame 810. In some embodiments, the outside diameter of the fibrous material covering provides a secure fit and/or seal between the frame 810 and the interior tissue surface of the target blood vessel.

The fibrous material 821 can be applied using rotary jet spinning entirely around the end 862 of the frame 810. The fibrous material 821 can have contours or otherwise undulate between the struts 801 of the frame 810 or the fibrous material 821 can be flush with the end 862 of the frame 810. The valve seat 818 can be defined by the inside diameter of the frame 810 and the inside diameter of the fibrous material 821. In such a configuration, the fibrous material 821 can effectuate a continuous seal between the outside diameter of the frame 810 and the interior surface of the target blood vessel and between the inside diameter of the frame 810 and a prosthetic valve device. As mentioned above, the docking device 820 can be adapted for use at a variety of different positions in the circulatory system, such as the aorta. In order to produce the desired fibrous covering 821, the rate of rotation of the rotary jet spinning reservoir and/or mandrel/holder, the rate of translation of the mandrel/holder, the angle and/or change in angle of the holder assembly may be controlled to produce the desired application of fibrous material.

FIGS. 32-34 and the accompanying description relate to embodiments of another example type of docking device 1000 that can be covered at least in part by fibrous material using rotary jet spinning solutions as described herein. In some embodiments, the docking device frame low of FIGS. 32 and 33 is suitable for use as a dock for a prosthetic heart valve, such as a transcatheter heart valve (e.g., aortic heart valve implant).

The docking device of FIGS. 32-34 comprises a frame 1010, which may be made at least in part of self-expanding memory metal (e.g., nitinol). The assembled/fabricated docking device 1000 (see FIG. 34) can be configured to be fixed inside a target vessel or chamber of the cardiac/circulatory system, such as the aortic root, to assist in annular fixation of a medical implant device, such as a transcatheter heart valve. The docking device 1000 may advantageously combine with a stent or other component of the heart valve implant to entrap native valve leaflets associated with the target vessel/chamber. The docking device 1000 may be used to anchor self-expanding and/or balloon-expanding implant devices therein.

The docking device 1000 may be implanted in any suitable or desirable medical process, such as a median sternotomy and left ventricular puncture followed by snaring and externalization of a wire from the femoral artery, wherein the docking device 1000 and anchored heart valve can be introduced from the femoral artery and apex on the wire. Alternatively, the docking device 1000 may be implanted using a fully-percutaneous approach through the femoral arteri(es).

The docking device 1000 can be used to secure a prosthetic heart valve within a native heart valve. Although use of docking devices in accordance with the present disclosure are described as being used to secure a transcatheter heart valve in the aortic valve or the mitral valve of a heart, it should be understood that the disclosed docking devices can be configured for use with any other heart valve as well. The frame 1010 includes a plurality prongs/arms 1028 (three in the illustrated embodiment) attached to respective peaks of the strut(s) 1020 of the frame 1010.

FIG. 33 shows the docking device frame 1010 disposed on a holder 1018, such as an arm-type holder as described herein. Although an arm holder is shown in FIG. 33, it should be understood that any type of holder may be used to hold the docking device frame 1010, including cylindrical or other-shaped spacer-type holders or other attachment features, as described herein. The mandrel 1019 and holder 1018 may be part of a collector assembly 1017, as described in detail herein.

With the docking device frame 1010 disposed on the holder 1018, the mandrel 1019 and coupled holder 1018 can be rotated about the axis defined by the mandrel 673. For example, the collector assembly 1017 can comprise a rotor motor configured to rotate the mandrel 1019. The various components of the collector assembly 1017 may be controlled at least in part by control circuitry of a local and/or remote controller system.

Fibrous material may be applied to the docking device frame 1010 using a rotary jet spinning deposition system, which may be similar in certain respects to the system 800 shown in FIGS. 8A and 8B. For example, a rotating reservoir containing a solution may be rotated at sufficient speed to eject/expel a plane of fibrous strand(s), as shown in FIGS. 8A and 8B. The fibrous strand(s) can be applied to at least a portion of the outer surface of the frame 1010 to form one or more layers of fibrous material, as shown in FIG. 25.

Fibrous material may be applied to at least a portion of the frame 1010 in order to provide covering for the docking device implant moo. In some implementations, rotary jet spinning may be used to apply fibrous material in a manner so as to surround or partially surround or cover at least a portion of the struts 1020 of the frame 1010.

The retaining arms 1028 can be used to help position and deploy the docking device 1000 into its proper location relative to the native aortic valve. The retaining arms 1028 eyelets/apertures therein, as shown. The upper/proximal end/peak of one or more of the struts 1020 can attach and/or be integrated with the retaining arms 1028. The retaining arms 1028 can be advantageously used with various types of delivery systems. For example, the shape of the arms 1028, which may have an enlarged head that can be used to secure the frame 1010 to a "slot-" based delivery system. In some implementations, the head portion (e.g., eyelet) of the arms 1028 can be used to secure the frame 1010 to a tether-type delivery system, which may utilize sutures, wires, or fingers to control delivery of the frame 1010. Such features can advantageously facilitate recapture and repositioning of the frame 1010 in situ. In addition, or as an alternative, the arm features 1028 may be used to secure the frame 1010 to the holder 1018 of the collection assembly 1017 of a rotary jet spinning system. For example, the heads 1029 can be used to suture, clip, snap, hook, or otherwise secure the strut head(s) 1029 to the arm(s) or other feature(s) of the holder 1018.

FIG. 34 shows a docking device 1000 having fibrous material 1022 applied to portions thereof using rotary jet spinning in accordance with one or more embodiments of the present disclosure. Fibrous material 1022 may be applied to one or more portions or components of the device 1000 using rotary jet spinning in any suitable or desirable manner. For example, the fibrous material 1022 can be applied to the exterior (and/or interior) of the frame 1010. In some embodiments, the fibrous material 1022 extends from upper ends of the frame struts 1020 to lower ends thereof. Application of the fibrous material can beneficially enhance sealing characteristics of the device 1000. Rotary jet spinning can be used to apply fibrous material having different sets of characteristics to different portions of the frame 1010. Processes of depositing the fibrous material can be performed as many times as desired and/or for the desired amount of time in order to produce the desired thickness and/or other characteristics of fibrous material. In order to produce the desired fibrous covering 1022, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 35:
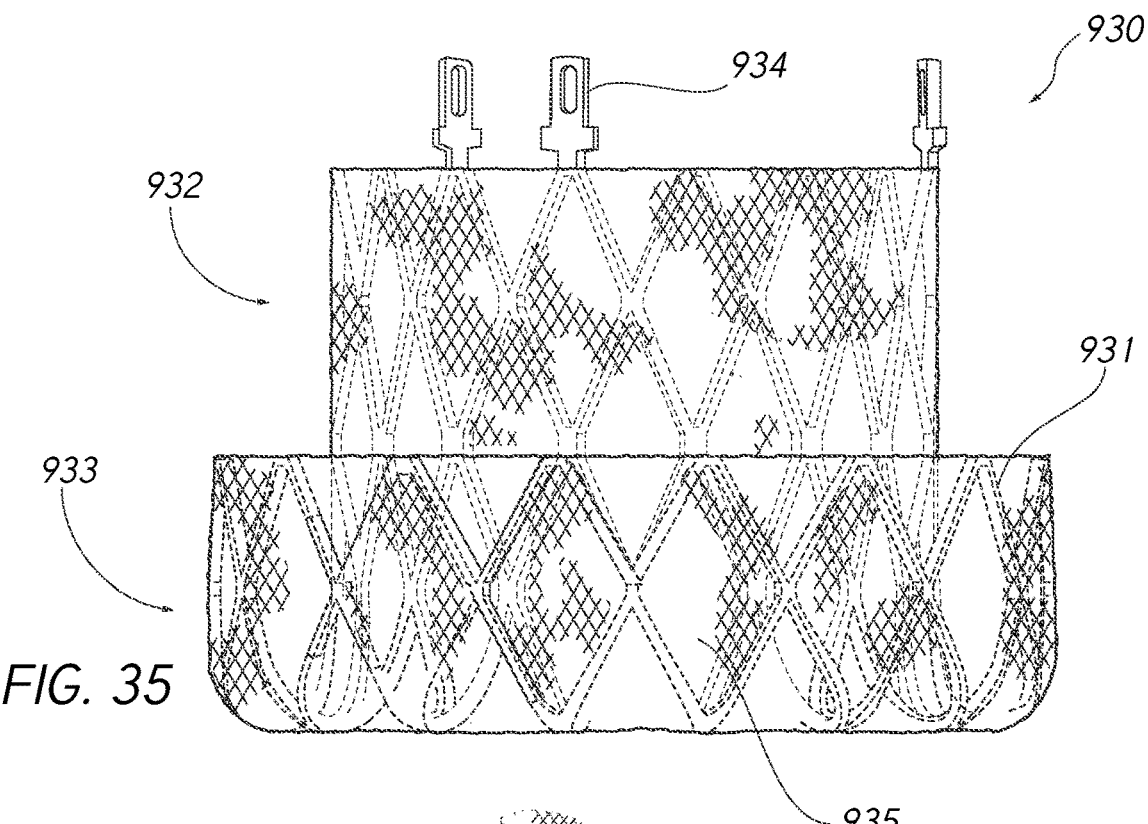
FIG. 35 shows a docking device that can be covered at least in part by fibrous material using rotary jet spinning solutions in accordance with one or more embodiments.
Figure 36:
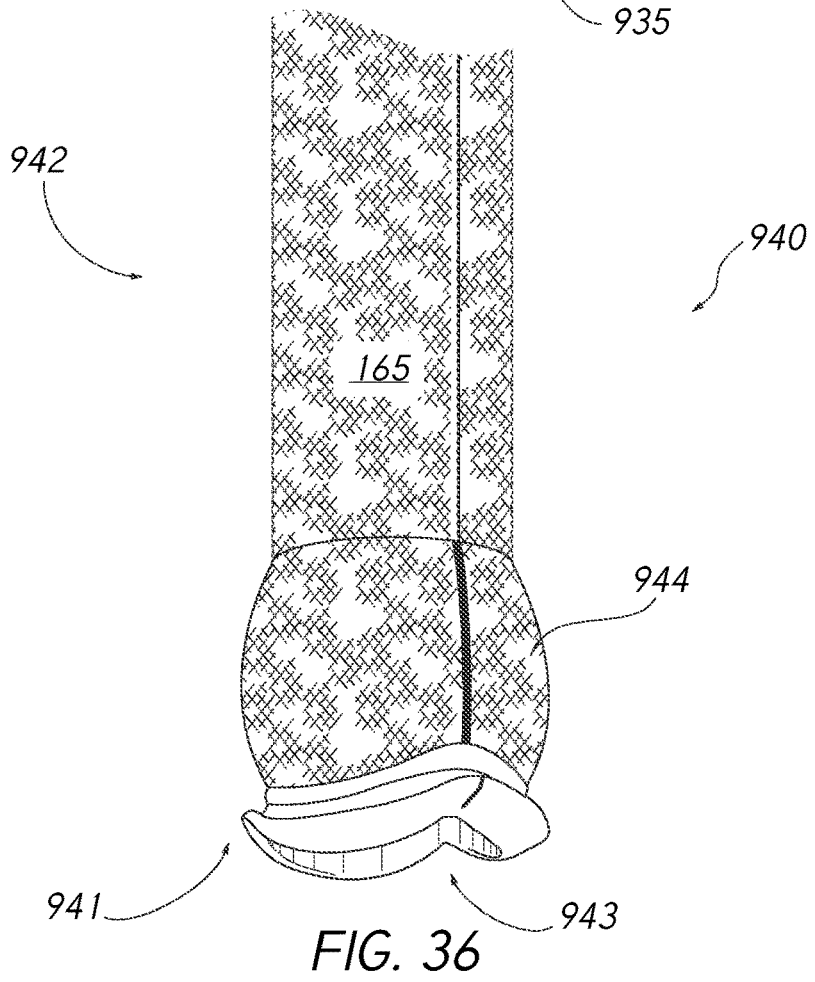
FIG. 36 shows a valved conduit assembly in accordance with one or more embodiments.

FIGS. 35 and 36 and the respective accompanying description relate to embodiments of other example types of docking devices that can be covered at least in part by fibrous material using rotary jet spinning solutions as described herein. In some embodiments, the docking devices 930, 940 of FIGS. 35 and 36 may be suitable for use as docks for prosthetic heart valves, such as a transcatheter heart valves (e.g., aortic).

The docking device 930 of FIG. 35 includes a support stent or frame 931 that can be used to help secure a heart valve implant into the interior of a native heart valve, such as an aortic valve. The frame 931 can have a generally annular or toroidal body formed from a suitable shape-memory metal or alloy, such as spring steel, cobalt-chromium (e.g., ELGILOY alloy), or nitinol. The frame 931 can be radially compressible to a smaller profile and can self-expand when deployed into its functional size and shape. In some embodiments, the frame 931 is not self-expanding.

The support frame 931 includes a generally cylindrical main body portion 932 and a rim portion 933. The frame 931 can be a lattice structure, which can be formed, for example, from multiple struts in which approximately half of the struts are angled in a first direction and approximately half of the struts are angled in a second direction, thereby creating a crisscross or diamond-shaped pattern. In the illustrated embodiment, the rim portion 933 has a greater diameter than the main body portion 932 and is formed as an extension at a bottom region of the main body portion that is folded outwardly from the main body portion and back toward a top region of the main body portion. The rim portion 933 can thus form a U-shaped rim or lip around the bottom region of the frame 910. In general, the rim portion 933 can be designed to have a diameter that is slightly larger than the walls of the aortic arch that surround the aortic valve. Thus, when the frame 910 is delivered to the aortic valve and deployed at the aorta, the rim portion 933 can expand to engage the surrounding aorta wall and frictionally secure the frame 910. At the same time, the main body portion 932 can define an interior into which an expandable heart valve implant (not shown) can be expanded and which further engages the native leaflets of, for example, the aortic valve.

The frame 931 can further include retaining arms 934 that can be used to help position and deploy the frame 910 into its proper location relative to the native valve. The retaining arms 934 can have apertures associated therewith, which may be used for various purposed, including to couple the frame 931 to a holder device for a rotary jet spinning system, as described in detail herein.

The frame 931 can have fibrous material 935 applied to portions thereof using rotary jet spinning in accordance with one or more embodiments of the present disclosure. Fibrous material 935 may be applied to one or more portions or components of the device 930 using rotary jet spinning in any suitable or desirable manner. For example, the fibrous material 935 can be applied to the exterior (and/or interior) of the frame 931. In some embodiments, the fibrous material 935 extends from upper ends of the frame struts of the body portion 932 to end of the rim portion 933. Application of the fibrous material can beneficially enhance sealing characteristics of the device 930. Rotary jet spinning can be used to apply fibrous material having different sets of characteristics to different portions of the frame 931. Processes of depositing the fibrous material 935 can be performed as many times as desired and/or for the desired amount of time in order to produce the desired thickness and/or other characteristics of fibrous material. In order to produce the desired fibrous covering 935, the rate of rotation of the rotary jet spinning reservoir and/or mandrel/holder, the rate of translation of the mandrel/holder, the angle and/or change in angle of the holder assembly may be controlled to produce the desired application of fibrous material.

FIG. 36 shows a valved conduit 940 including a conduit graft 942 that is integrated with a prosthetic valve implant device 941 (partially obscured within conduit graft 942 in FIG. 36). Together, the conduit 942 and the valve device 941 form a two-piece valved conduit assembly. The conduit graft 942 can be configured to facilitate replacement of a previously-implanted prosthetic valve implant device. That is, a heart valve 941 within a valved conduit 940 can sometimes becomes calcified and must be replaced. The combination 940 can provide for relatively easy valve removal.

In some implementations, the conduit graft 942 can be used as an aortic conduit graft, for example. As shown, the prosthetic heart valve 941 can be positioned at least partially within one end of the conduit graft 942. The valved conduit 940 can be used for replacing a native aortic valve and/or ascending aorta. However, it should be understood that certain principles disclosed herein would also apply to replacement of the pulmonary valve and the pulmonary artery.

The heart valve 941 may include a rigid or semi-rigid stent supporting a plurality of flexible leaflets (not shown) that are mounted to the peripheral stent structure and form fluid occluding surfaces within the valve orifice to form a one-way valve. The frame structure can include a plurality of generally axially extending commissures, circumferentially distributed around the valve between and in the same number as the number of leaflets, as described in detail above. The valve orifice can be oriented around an axis along an inflow-outflow direction through the valve 941. FIG. 36 shows a sewing ring component of the valve 941 exposed beyond the conduit graft 942 on the inflow end thereof, which may conform to the undulating contours of the valve cusps, or define a generally circular, planar ring.

The conduit graft 942 may define a generally tubular structure that extends from an inflow end 943 to an outflow end (not shown). In the embodiment shown, the valve 941 is associated with the conduit graft 941 in such a way that the valve leaflets control flow of blood through the conduit by permitting blood flow into the conduit (e.g., blood flow into the aorta, when the conduit is used for aortic replacement) while preventing flow of blood out of the conduit in the opposite direction (e.g., back into the left ventricle of the patient when used for aortic replacement).

The illustrated conduit graft 942 is particularly suited for attachment within the aortic annulus and ascending aorta, and as such can closely match the aortic root anatomy and include an enlarged region or bulge 944 close to the inflow end 943 that conforms to the sinuses of Valsalva just above the aortic annulus. The conduit graft 942 can have fibrous material 945 applied thereto using rotary jet spinning in accordance with embodiments of the present disclosure. In some implementations, the fibrous material 945 can be sealed with a bioresorbable medium such as gelatin or collagen. The form of at least a portion of the conduit graft 942 can include circumferentially corrugated (e.g., grooved) or pleated sidewall portion(s) that provide longitudinal flexibility and/or radial compressibility while ensuring that the graft does not unduly radially expand under the pressure of blood flowing therethrough. The enlarged region or bulge 944 may be configured with longitudinal corrugations that are more radially expandable than the circumferential pleats to allow expansion at that location into the Valsalva sinuses. The conduit graft 942 may desirably have a length of from a few centimeters to 10-12 centimeters.

The conduit graft 942 can have fibrous material 945 applied to portions thereof using rotary jet spinning in accordance with one or more embodiments of the present disclosure. Fibrous material 945 may be applied to one or more portions or components of the device 940 using rotary jet spinning in any suitable or desirable manner. For example, the fibrous material 945 can be applied to one or more portions of the exterior of the conduit graft 942. In some embodiments, the fibrous material 945 extends from the outflow end of the conduit graft 942 to the end of the bulge portion 944. Application of the fibrous material 945 can beneficially enhance sealing characteristics of the device 940. Rotary jet spinning can be used to apply fibrous material having different sets of characteristics to different portions of the conduit graft 942. Processes of depositing the fibrous material 945 can be performed as many times as desired and/or for the desired amount of time in order to produce the desired thickness and/or other characteristics of fibrous material. In order to produce the desired fibrous covering 945, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 37:
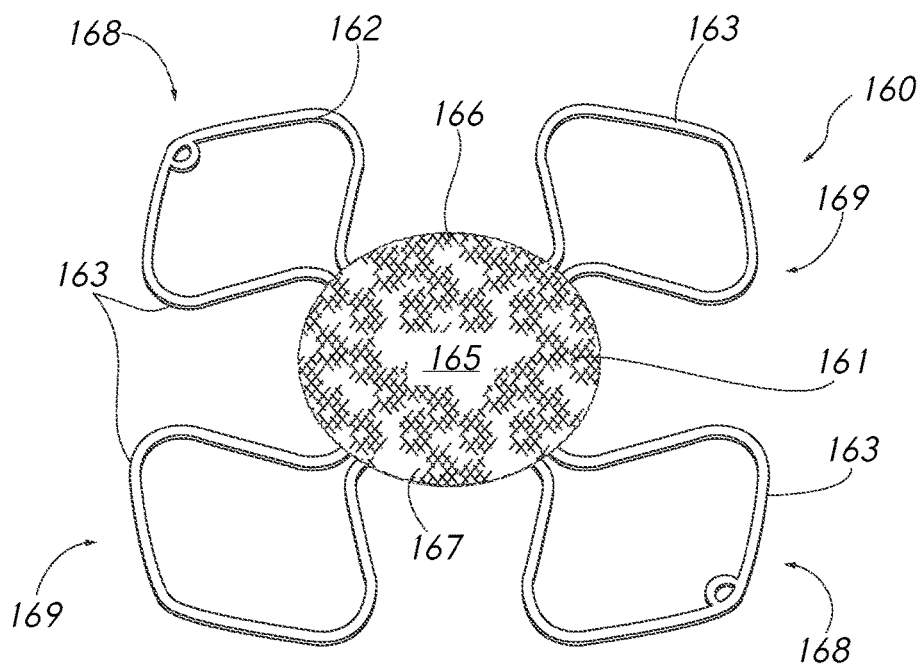
FIG. 37 illustrates a septal closure device having fibrous material applied to one or more portions thereof using rotary jet spinning in accordance with one or more embodiments.

FIG. 37 illustrates a septal closure device 160 including a blood occluding portion 161 formed at least in part of fibrous material 165 applied to a frame 162 using rotary jet spinning process(es) according to one or more embodiments of the present disclosure. The septal closure device 160 may be configured to be implanted in or to a septal wall to at least partially close a septal orifice. In some embodiments, the septal closure device 160 allows for re-entry through the septum at the same septal orifice location at a later time as other therapeutic interventions are warranted. In certain embodiments, the closure device 160 is configured to provide an access port for accessing the left side of the heart with a catheter or other medical device. In some implementations, the closure device 160 can be implanted in orifices formed in a ventricular septum, the apex or other sections of the heart, or in orifices (surgically or congenitally formed orifices) formed in other organs of the body.

The septal closure device 160 can include a frame 162 configured to support the blood-occluding fibrous material 165. The frame 162 in the illustrated configuration can comprise a generally planar body comprising a central portion 166 and a plurality of anchoring arms 163 extending radially outward from the central portion 166. For example, at least four arms can extend from the central portion 166, as shown in the illustrated embodiment, although the frame can have greater than four arms or less than four arms in other embodiments.

The four arms 163 may include a first set of opposing distal arms 168, and a second set of opposing proximal arms 169, extending from the central portion 166, as illustrated. The closure device desirably (although not necessarily) has the same number of arms in the first and second sets so that the clamping force exerted by the arms is evenly distributed against the septum when the device is implanted. In a deployed or expanded configuration, the arms 163 can extend radially outwardly from the central portion 166. The arms 163 can extend perpendicularly or substantially perpendicularly to a central axis of the device 160 (the central axis extending orthogonal to the plane of the page) such that the septum wall can be compressed or pinched between the first set of arms 168 and the second set of arms 169 when the device 160 is implanted in the atrial septum. In other words, when the device 160 is implanted, the first set of arms 168 can be on one side of the atrial septum, the second set of arms 169 can be on the other side of the atrial septum, and the central portion 166 can be disposed within an orifice or defect or offset to one side of the septum.

The frame 162 can have a relatively thin and flat profile to avoid or minimize thrombus risk. Thus, to such end, the arms 163 can be attached to the central portion 166 at angularly spaced apart locations on the central portion, with the attachment locations intersecting a common plane perpendicular to the central axis; in other words, all of the arms 163 in the illustrated embodiment can be attached to the central portion along the same circumferential path defined by the central portion 166.

Additionally, the arms 163 and the connecting frame portions 167 (covered by the fibrous material 165 in the illustrated configuration) of the illustrated frame 162 can collectively form a simple closed loop structure wherein a single continuous frame member forms each of the arms and the connecting portions. Each of the arms 163 can have a variety of shapes. For example, embodiments of the plurality of arms 163 may have a mushroom shape, a diamond shape, or a circular shape.

The central portion 166 of the frame 162 can have the fibrous material 165 applied to portions thereof using rotary jet spinning in accordance with one or more embodiments of the present disclosure. Fibrous material 165 may be applied to one or more portions or components of the device 160 using rotary jet spinning in any suitable or desirable manner. For example, the fibrous material 165 can be applied to one or both sides of the central portion 166 using rotary jet spinning. In some embodiments, the fibrous material 165 covers substantially the entire central portion 166, as shown, or may alternatively only cover one or more bands or portions thereof. Application of the fibrous material can beneficially enhance occluding characteristics of the device 160. Rotary jet spinning can be used to apply fibrous material having different sets of characteristics to different portions of the device 160. Furthermore, processes of depositing the fibrous material 165 can be performed as many times as desired and/or for the desired amount of time in order to produce the desired thickness and/or other characteristics of fibrous material. In order to produce the desired fibrous covering 165, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 38:
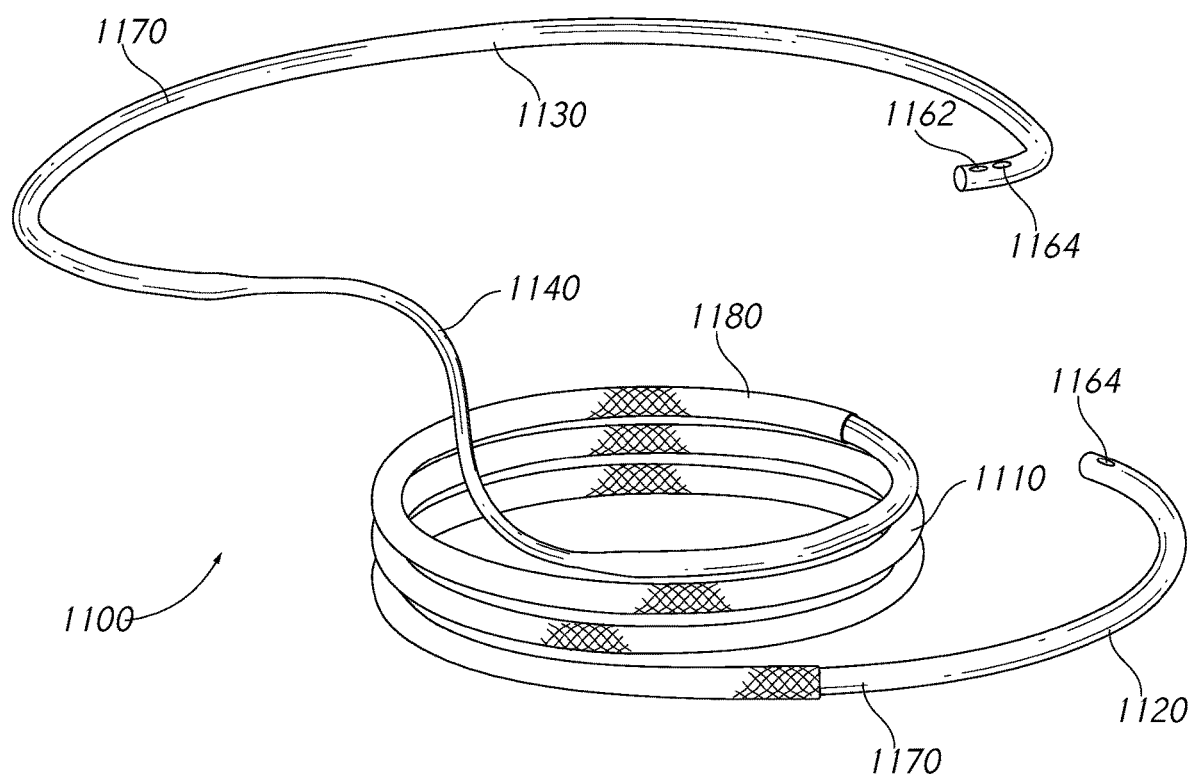
FIG. 38 illustrates a docking device having fibrous material applied to one or more portions thereof using rotary jet spinning in accordance with one or more embodiments.

FIG. 38 illustrates another embodiment of a docking device 1100 including fibrous material 1180 applied to portions thereof using rotary jet spinning in accordance with one or more embodiments. The docking device 1100 can be configured to can be used in conjunction with an expandable transcatheter heart valve at a native valve annulus (e.g., mitral or tricuspid valve annulus), in order to more securely implant and hold the prosthetic valve at the implant site. Anchoring/docking devices according to embodiments of the present disclosure can provide or form a more circular and/or stable annulus at the implant site, in which prosthetic valves having circular or cylindrically-shaped valve frames or stents can be expanded or otherwise implanted.

In addition to providing an anchoring site for a prosthetic valve, the anchoring/docking device 1100 can be sized and shaped to cinch or draw the native valve (e.g., mitral, tricuspid, etc.) anatomy radially inwards. In this manner, one of the main causes of valve regurgitation (e.g., functional mitral regurgitation), specifically enlargement of the heart (e.g., left ventricle) and/or valve annulus, and consequent stretching out of the native valve (e.g., mitral) annulus, can be at least partially offset or counteracted. Some embodiments of the anchoring or docking device 1100 further include features which, for example, are shaped and/or modified to better hold a position or shape of the docking device during and/or after expansion of a prosthetic valve therein. By providing such anchoring or docking devices, replacement valves can be more securely implanted and held at various valve annuluses, including at the mitral annulus which does not have a naturally circular cross-section.

The docking device 1100 can include a central region 1110, a lower region 1120, an upper region 1130, and an extension region 1140. In some embodiments, the lower and upper regions 1120, 1130 can form larger coil diameters than the central region 1110, and the extension region 1140 can space the upper region 1130 apart from the central region 1110 in a vertical direction.

The central coils/turns 1110 of the docking device 1100 can provide a main docking site for a prosthetic valve that is expanded therein. The central turns 1110 can generally be positioned in the left ventricle, while a small distal portion, if any, may extend through the native valve annulus and into the left atrium. The central turns 1110 can be configured to sufficient force for stably holding the expanded valve implant in the docking device 1100 and preventing the valve from dislodging from the docking device 1100, even during severe mitral pressures.

The lower region 1120 of the docking device 1100 can serve as a leading coil/turn (e.g., a ventricular encircling turn). The lower region 1120 includes the distal tip of the docking device 1100 and flares radially outwardly from the central turns 1100 in order to capture the native valve leaflets, and some or all of the chordae and/or other mitral anatomy when the docking device 1100 is advanced into the left atrium.

The upper region 1130 of the docking device 1100 can serve as the stabilization coil/turn (e.g., atrial coil/turn) that provides the docking device 1100 with a self-retention mechanism during the transition phase after the docking device 1100 is deployed at the native valve and prior to delivery of the THV. For example, the diameter of the upper region 1130 can be selected to allow the upper region 1130 to fit at an approximate desired height in the left atrium, and to prevent the upper region 1130 from sliding or dropping further towards the native mitral annulus after the desired position is achieved.

The extension region 1140 provides a vertical extension and spacing between the central region 1110 and the upper region 1130 of the docking device 1100. The location at which the docking device 1100 crosses the mitral plane is important in preserving the integrity of the native valve anatomy, and specifically the valve leaflets and commissures, to serve as an appropriate docking site for the final implantation of the valve implant. In docking devices without such an extension or ascending region 1140, more of the docking device would sit on or against the mitral plane and pinch against the native leaflets, and the relative motion or rubbing of the docking device against the native leaflets could potentially damage the native leaflets from the atrial side. Having an extension region 1140 allows the portion of the docking device 1100 that is positioned in the left atrium to ascend away and be spaced apart from the mitral plane.

The docking device 1100 can include a low friction (e.g., ePTFE) cover layer 1170 that may improve interactions between the ends of the docking device 1100 and the native heart anatomy. For example, additional friction may be more desirable on at least a portion of the central region 1110, which provides the functional coils of the docking device 1100 for docking the valve implant. Therefore, fibrous material 1180 can be applied to the central region 1110 of the docking device 1100 using rotary jet spinning process(es) in accordance with embodiments of the present disclosure. The fibrous material 1180 can provide additional friction between adjacent coils and against the native leaflets and/or valve implant device docked in the docking device 1100. The friction that is provided by the fibrous material 1180 at the interfaces between coils and between the inner surface of the central region 1110 of the docking device 1100, the native mitral leaflets, and/or the outer surface of the valve implant can create a more secure locking mechanism to more strongly anchor the valve device and the docking device 1100 to the native valve. Since the functional coils/turns or central region 1110 of the docking device 1100, that is, the region of the docking device that interacts with the valve implant device, may be the only region where a high friction fibrous material/layer is desired, the fibrous material 118o may be applied using rotary jet spinning selectively only to portion(s) of the central region 1110, such that other regions remain low-friction in order to facilitate less traumatic interactions with the native valve and other heart anatomy.

The docking device 1100 can have fibrous material 1180 applied to portions thereof using rotary jet spinning in accordance with one or more embodiments of the present disclosure. Fibrous material 1180 may be applied to one or more portions or components of the device 1100 using rotary jet spinning in any suitable or desirable manner. For example, the fibrous material 1180 can be applied to one or more portions of the exterior and/or interior of the coils 1110 and/or other portions of the docking device 1100. Rotary jet spinning can be used to apply fibrous material having different sets of characteristics to different portions of the docking device 1100. Processes of depositing the fibrous material 1180 can be performed as many times as desired and/or for the desired amount of time in order to produce the desired thickness and/or other characteristics of fibrous material. In order to produce the desired fibrous covering 1180, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 39:
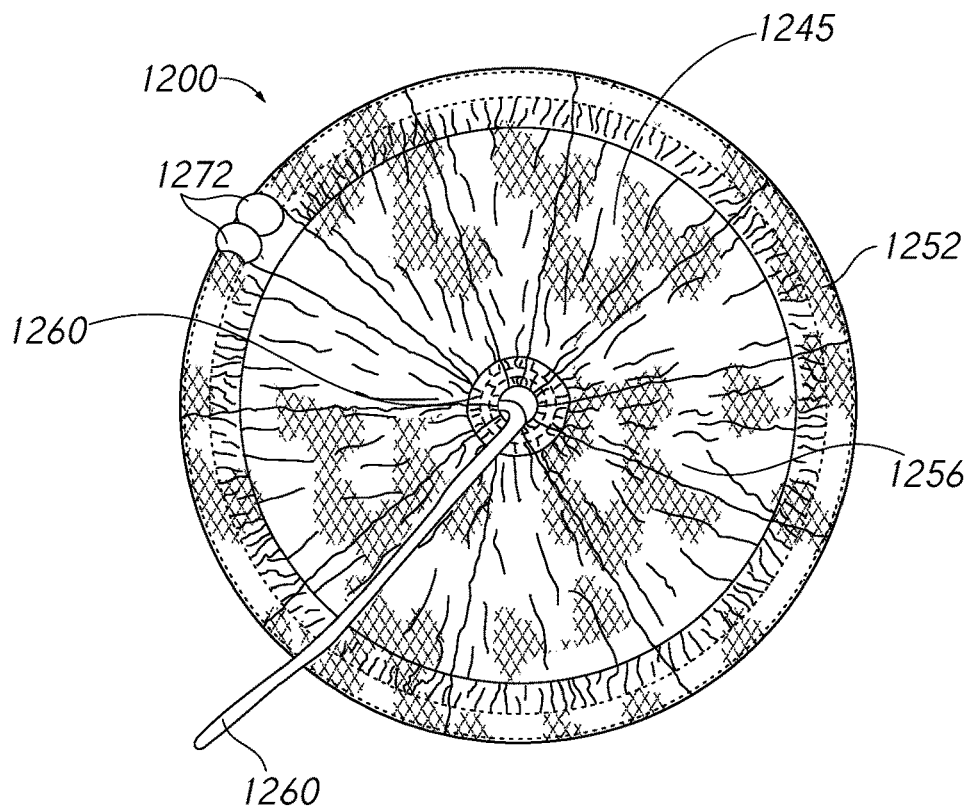
FIG. 39 illustrates a tissue anchor device having fibrous material applied to one or more portions thereof using rotary jet spinning in accordance with one or more embodiments.

FIG. 39 illustrates a tissue anchor device 1200 including fibrous material 1245 applied to portions thereof using rotary jet spinning in accordance with one or more embodiments. The device 1200 may be used for medical treatment and/or treating heart conditions, including, by way of example, treating dilation/dilatation (including a dilated left ventricle), valve incompetence (including mitral valve regurgitation), and other similar heart failure conditions. In some implementations, the device 1200 operates to assist in an apposition of heart valve leaflets so as to improve valve function. In addition, the device 1200 may either be placed in conjunction with other devices that are configured to alter the shape or geometry of the heart, locally and/or globally, and thereby further increase the heart's efficiency. That is, the device 1200 may function alone or in concert with one or more other implant devices to facilitate an increased pumping efficiency of the heart by way of an alteration in the heart's shape or geometry and concomitant reduction in stress on heart walls, and through an improvement in valve function.

In some implementations, the anchor device 1200 suitable for fixating a mitral valve splint device within the heart and/or left atrium. The anchor 1200 may be self-expandable and may comprise a ring 1252 which may peripherally support a cover portion 1256 that is covered at least in part with fibrous material 1245 using rotary jet spinning in accordance with embodiments of the present disclosure. Upon cinching a centrally disposed tension member or cord 1260, the cover 1256 can assume a circular, flattened, disc-shaped, or pie-shaped configuration, as shown, e.g., when the interior ends of the tabs 1288 are pulled toward the center, or can assume a cone shaped configuration if the ends of the tabs 1288 are pulled in a direction perpendicular to a plane aligned with the ring 1252, such as when the tension member pulls the anchor 1200 toward another anchor.

The deployed or expanded configuration (e.g., circular/disc-shaped/pie-shaped/cone-shaped configuration) of the self-expandable anchor 1200 can be suited for anchoring a tension member in a position within the heart, such as the left atrium, as well as withstanding the forces encountered during changing the shape of the heart. Generally, a larger surface area of the cover portion 1256 can help the anchor 1200 withstand higher forces. For example, a relatively large surface area of the cover 1256 coupled with a centrally-disposed tension member 1260 can provide an inherently stable configuration of the anchor 1200, thereby eliminating or reducing the risk of mechanical failures and migration into the tissue as encountered with certain other anchors. Further, where the cover 1256 has a relatively large surface area and the tension member 1260 is associated with the center of the device, as shown, the device 1200 can operate as a closure device which seals the punctures in the walls of the heart or other anatomy. In some implementations, the fibrous material 1245 is applied in a manner as to form a generally conical shape configuration when placed under tension so as to inhibit migration of the anchor during beating of the heart.

The anchor device 12100 can have fibrous material 1245 applied to portions thereof using rotary jet spinning in accordance with one or more embodiments of the present disclosure. Fibrous material 1245 may be applied to one or more portions or components of the device 1200 using rotary jet spinning in any suitable or desirable manner. For example, the fibrous material 1245 can be applied to one or more portions of the cover 1256 and/or ring 1252. Rotary jet spinning can be used to apply fibrous material having different sets of characteristics to different portions of the anchor device 1200. Processes of depositing the fibrous material 1245 can be performed as many times as desired and/or for the desired amount of time in order to produce the desired thickness and/or other characteristics of fibrous material. In order to produce the desired fibrous material 1245, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 40:
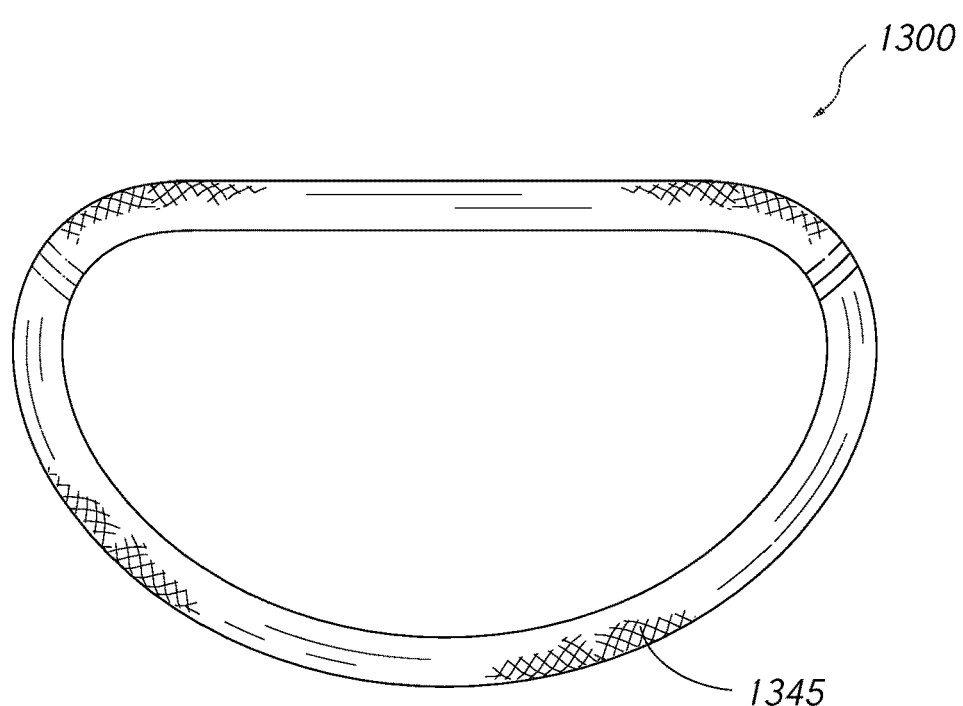
FIG. 40 illustrates an annuloplasty repair device having fibrous material applied to one or more portions thereof using rotary jet spinning in accordance with one or more embodiments.

FIG. 40 illustrates another embodiment of an annuloplasty repair device 1300 including fibrous material 1245 applied to portions thereof using rotary jet spinning in accordance with one or more embodiments. The annuloplasty repair device 1300 can be configured to restore the specific morphology and dynamic characteristics of heart valves damaged by various degenerative valvular disease to overcome some of the limitations of currently available rings is described.

The annuloplasty repair device 1300 can be a semi-rigid ring device. The device 1300 can include a relatively rigid anterior side and a gradually more flexible posterior side to provide some flexibility to the ring while preserving its annular remodeling effect. The annuloplasty repair device 1300 can have fibrous material 1345 applied to portions thereof using rotary jet spinning in accordance with one or more embodiments of the present disclosure. Fibrous material 1345 may be applied to one or more portions or components of the device 1300 using rotary jet spinning in any suitable or desirable manner. For example, the fibrous material 1345 can be applied to one or more inner or outer portions of the ring form of the device. Rotary jet spinning can be used to apply fibrous material having different sets of characteristics to different portions of the annuloplasty repair device 1300. Processes of depositing the fibrous material 1345 can be performed as many times as desired and/or for the desired amount of time in order to produce the desired thickness and/or other characteristics of fibrous material. In order to produce the desired fibrous covering 1345, the rate of rotation of the rotary jet spinning reservoir and/or mandrel/holder, the rate of translation of the mandrel/holder, the angle and/or change in angle of the holder assembly may be controlled to produce the desired application of fibrous material.

Figure 41:
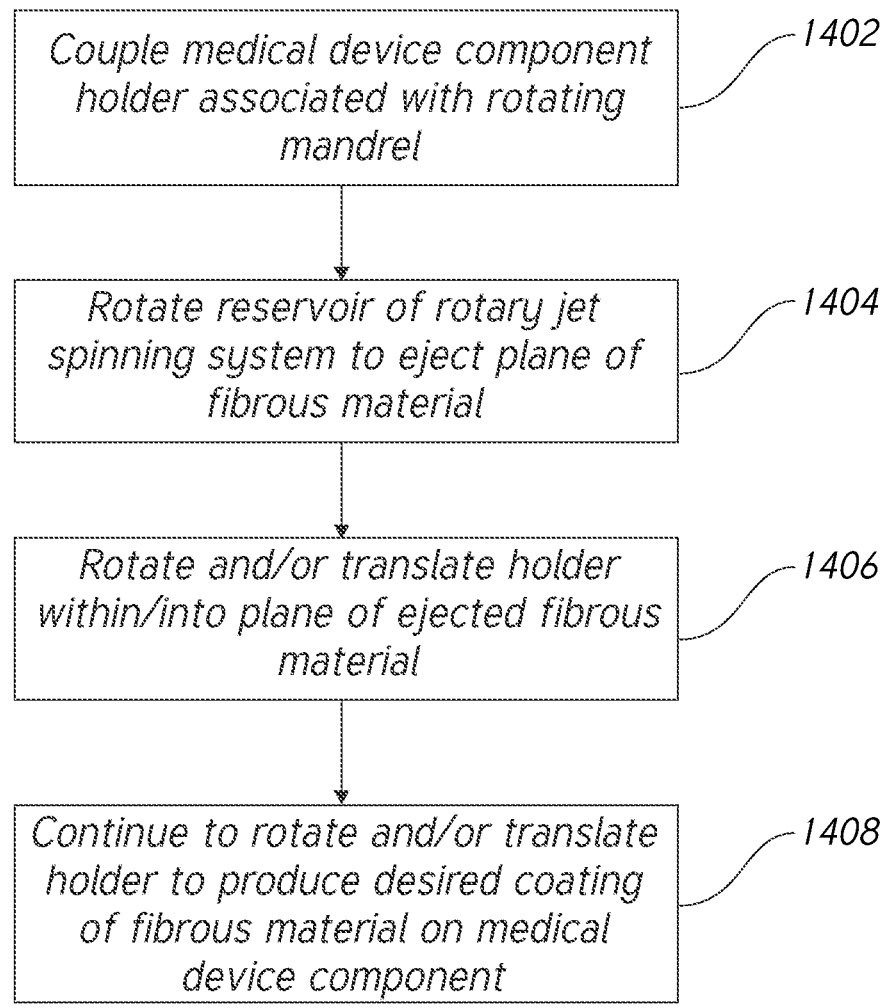
FIG. 41 is a flow diagram for a process for applying fibrous material to a medical device component in accordance with one or more embodiments.

FIG. 41 is a flow diagram for a process 1400 for applying fibrous material to a medical device component. At block 1402, the process 1400 involves coupling a medical device component to a holder associated with a rotating mandrel. The holder and/or mandrel may be part of a collection assembly, as described herein. Furthermore, the holder may be a spacer-type or arm-type holder, as described in detail herein.

At block 1404, the process 1400 involves rotating a reservoir of a rotary jet spinning system to eject a plane of fibrous material, as described herein. For example, the reservoir can comprise a volume of polymeric solution that is ejected from one or more orifices in the reservoir when the reservoir is rotated at a sufficient speed. The reservoir device can be part of a deposition assembly.

At block 1406, the process 1400 involves rotating and/or translating the holder within/into the plane of ejected fibrous material using the mandrel and/or one or more other components of the collection assembly. The holder is advantageously rotated concurrently with the rotation of the reservoir. At block 1408, the process 1400 involves continuing to rotate and/or translate the holder to produce a desired coating of fibrous material on one or more portions of the medical device component.

The process 1400 may be performed at least in part by control circuitry coupled to the collection assembly and/or the deposition assembly.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of applying fibrous material to a medical device component, the method comprising:
    coupling a surgical heart valve device to a holder device, the surgical heart valve device including:
        a non-expandable sealing ring;
        a plurality of commissure posts projecting in an outflow direction on an outflow side of the sealing ring; and
        an expandable skirt frame extending on an inflow side of the sealing ring;
    rotating a reservoir device to expel at least a portion of a first liquid polymeric solution from an orifice of the reservoir device, the expelled at least a portion of the first liquid polymeric solution forming one or more first strands of fibrous material in a first deposition plane;
    rotating the holder device at least partially within the first deposition plane to apply at least a portion of the one or more first strands of fibrous material to the sealing ring and the plurality of commissure posts of the surgical heart valve device, thereby forming a first fibrous covering having a first set of characteristics on the sealing ring and the plurality of commissure posts;
    rotating the reservoir device to expel at least a portion of a second liquid polymeric solution from the orifice of the reservoir device, the expelled at least a portion of the second liquid polymeric solution forming one or more second strands of fibrous material in a second deposition plane; and
    rotating the holder device at least partially within the second deposition plane to apply at least a portion of the one or more second strands of fibrous material to the skirt frame of the surgical heart valve device, thereby forming a second fibrous covering having a second set of characteristics on the skirt frame.

2. The method of claim 1, wherein the holder device is a component of a collection assembly further comprising:
    a rotary motor; and
    a mandrel that is mechanically coupled to the holder device and the rotary motor.

3. The method of claim 2, further comprising translating the collection assembly along a vertical axis while expelling the at least a portion of the first liquid polymeric solution.

4. The method of claim 1, wherein the holder device is an at least partially cylindrical spacer form.

5. The method of claim 4, further comprising applying an additional portion of the one or more second strands of fibrous material to a surface of the holder device, thereby forming a surplus fibrous covering portion on the surface of the holder device.

6. The method of claim 5, further comprising:
    decoupling the surgical heart valve device from the holder device; and folding the surplus fibrous covering portion over an inflow edge of the skirt frame to cover at least a portion of an inside surface of the skirt frame.

7. The method of claim 1, wherein the holder device comprises a plurality of arms configured to be coupled to the skirt frame.

8. The method of claim 7, wherein said coupling the skirt frame to the holder device comprises suturing the skirt frame to the plurality of arms of the holder device.

9. The method of claim 1, wherein rotating the reservoir device and the holder device is performed at least in part using control circuitry communicatively coupled to a collection assembly associated with the holder device and a deposition assembly associated with the reservoir device.

10. The method of claim 1, wherein the holder device comprises an at least partially cylindrical spacer form.

11. The method of claim 10, wherein the spacer form has a non-uniform longitudinal diameter.

12. A method of applying fibrous material to a medical device, the method comprising:
coupling a leaflet spacer device to a holder device, the leaflet spacer device including:
a main spacer body and;
a plurality of clip members configured to be movable to capture one or more leaflets of a heart valve between the plurality of clip members and the main spacer body;
opening the plurality of clip members to a straightened-out configuration exposing inside surfaces of the main spacer body and the plurality of clip members;
rotating a reservoir device to expel a first portion of fibrous material in a first deposition plane; and
rotating the holder device at least partially within the first deposition plane to apply the first portion of fibrous material to the inside surfaces of the main spacer body and the plurality of clip members of the leaflet spacer device, thereby forming a fibrous covering on the inside surfaces of the main spacer body and the plurality of clip members.

13. The method of claim 12, further comprising:
closing the plurality of clip members; and
covering outside surfaces of at least a portion of the plurality of clip members with a second portion of fibrous material expelled from the reservoir device when the plurality of clip members are in a closed configuration.

14. The method of claim 12, wherein:
the leaflet spacer device includes a hub member; and
coupling the leaflet spacer device to the holder device involves clipping the holder device at least partially around the hub member.

15. The method of claim 12, further comprising transitioning the leaflet spacer device from the straightened-out configuration to a folded configuration after said forming the fibrous covering on the inside surfaces of the main spacer body and the plurality of clip members.

16. A method of applying fibrous material to a medical device component, the method comprising:
coupling a holder device to a rotatable mandrel;
coupling a prosthetic heart valve to the holder device, the prosthetic heart valve including:
a sealing ring;
a first frame including a plurality of commissure posts; and
a second frame extending on an inflow side of the sealing ring;
rotating a reservoir device to expel a first portion of liquid polymeric solution in a first deposition plane;
rotating the holder device at least partially within the first deposition plane to apply the first portion of liquid polymeric solution to the sealing ring, thereby forming a first fibrous covering having a first set of characteristics on the sealing ring;
rotating the reservoir device to expel a second portion of liquid polymeric solution in a second deposition plane; and
rotating the holder device at least partially within the second deposition plane to apply the second portion of liquid polymeric solution to the second frame, thereby forming a second fibrous covering having a second set of characteristics that are different from the first set of characteristics on the second frame.

17. The method of claim 16, wherein:
the holder device comprises a plurality of arms; and
said coupling the prosthetic heart valve to the holder device involves coupling the second frame to the plurality of arms.

18. The method of claim 16, further comprising: withdrawing the prosthetic heart valve from the holder device.

19. The method of claim 16, further comprising folding a portion of the second fibrous covering over an inflow edge of the prosthetic heart valve.

20. The method of claim 16, wherein the holder device comprises a spacer form.

* * * * *